US012667484B2

(12) United States Patent
Laccetti et al.

(10) Patent No.: US 12,667,484 B2
(45) Date of Patent: Jun. 30, 2026

(54) BALLISTIC DELIVERY AND RELATED PARTICLES, COMPOSITIONS, METHODS AND SYSTEMS

(71) Applicant: CALIFORNIA INSTITUTE OF TECHNOLOGY, Pasadena, CA (US)

(72) Inventors: Benjamin J. Laccetti, Pasadena, CA (US); Julia A. Kornfield, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 1208 days.

(21) Appl. No.: 17/376,024

(22) Filed: Jul. 14, 2021

(65) Prior Publication Data

US 2022/0015943 A1 Jan. 20, 2022

Related U.S. Application Data

(60) Provisional application No. 63/051,677, filed on Jul. 14, 2020.

(51) Int. Cl.

| | |
|---|---|
| ***A61F 9/00*** | (2006.01) |
| ***A61M 5/30*** | (2006.01) |
| ***C08L 67/04*** | (2006.01) |

(52) U.S. Cl.
CPC ............. *A61F 9/0008* (2013.01); *A61M 5/30* (2013.01); *C08L 67/04* (2013.01); *A61M 2202/0241* (2013.01); *A61M 2210/0612* (2013.01)

(58) Field of Classification Search
CPC ................... A61F 9/0008; A61M 5/30; A61M 2202/0241; A61M 2210/0612; C08L 67/04
See application file for complete search history.

(56) References Cited

U.S. PATENT DOCUMENTS

| | | | |
|---|---|---|---|
| 7,892,836 B2 | 2/2011 | Groisman et al. | |
| 2005/0084537 A1* | 4/2005 | Martyn .................. | A61K 38/28 424/489 |
| 2008/0206870 A1 | 8/2008 | Groisman et al. | |
| 2009/0175949 A1 | 7/2009 | Borovkov et al. | |
| 2019/0142864 A1 | 5/2019 | Newman et al. | |
| 2021/0322462 A1 | 10/2021 | Newman et al. | |
| 2022/0281859 A1 | 9/2022 | Chakravarty et al. | |
| 2023/0173142 A1 | 6/2023 | Kornfield et al. | |

OTHER PUBLICATIONS

D.L. Tanelian, M.A. Barry, S.A . Johnston, T. Le and G. Smith. Controlled Gene Gun Delivery and Expression of DNA Within the Cornea, Biotechniques, 13: 484-488 (Sep. 1997), cited in IDS dated Apr. 18, 2024. (Year: 1997).*

D. Zhang, D. B. Das, and C. D. Rielly "Potential of microneedle-assisted micro-particle delivery by gene guns: a review," Drug Deliv, 2014; 21(8): 571-587). (Year: 2014).*

N. Zilony, A. Tzur-Balter, E. Segal, & O. Shefi, "Bombarding Cancer: Biolistic Delivery of therapeutics using Porous Si Carriers," Scientific Reports 3: 2499, p. 1-6, 2013. (Year: 2013).*

Arokoski, Jari P.A. et al."Feasibility of the use of a novel soft tissue stiffness meter", Physiological Measurement, Institute of Physics Publishing, 2005, 26, pp. 215-228.

Bassett, D.C. et al., "Dissolution of copper mineral phases in biological fluids and the controlled release of copper ions from mineralized alginate hydrogels", Biomed Mater., Dec. 29, 2014. 10(1); 015006. 24 pages. Doi: 10.1088/1748-6041/10/1/015006.

Cornu, Christophe, et al. "Stiffness of Knee Extensors in Duchenne Muscular Dystrophy", Muscle and Nerve, Short Reports, Dec. 1998, 21, pp. 1772-1774.

Gefen, A., et al., "Integration of plantar soft tissue stiffness measurements in routine MRI of the diabetic foot", Clinical Biomechanics, 16 (2001), pp. 921-925.

Gilbertson, M.W., et al., "Ergonomic control strategies for a handheld force-controlled ultrasound probe", 2012 IEEE/RSJ International Conference on Intelligent Robots and Systems, Oct. 7-12, 2012. Vilamoura, Algarve, Portugal. pp. 1284-1291.

Gilbertson, M.W., et al., "Force and Position Control System for Freehand Ultrasound", IEEE Transactions on Robotics, vol. 31, No. 4, Aug. 2015, pp. 835-849.

Abelson, M.B., et al., "Why Doesn't the Ocular Drug Work? A look at the various barriers and aids to the efficacy of ocular medications," *Review of Opthalmology*, Dec. 22, 2009. 7 pages.

Abhari, S., et al., "Anatomic studies of the miniature swine cornea," *The Anatomical Record*, 2018. 301(11): p. 1955-1967. 14 pgs.

Ahmed, I., "The noncorneal route in ocular drug delivery," in *Ophthalmic drug delivery systems*. 2003, CRC Press. p. 335-363. 31 pages.

Akers, B., et al., "Impact dynamics of a solid sphere falling into a viscoelastic micellar fluid," *Journal of Non-Newtonian Fluid Mechanics*, 2006. 135(2-3): p. 97-108. 13 pages.

Alemrayat, B., et al., "Preparation and optimization of monodisperse polymeric microparticles using modified vibrating orifice aerosol generator for controlled delivery of letrozole in breast cancer therapy," *Drug development and industrial pharmacy*, 2018. 44(12): p. 1953-1965. 16 pages.

Berglund, R.N., et al., "Generation of monodisperse aerosol standards," *Environmental Science & Technology*, Feb. 1973. 7(2): p. 147-153. 8 pages.

Bidwell, G., et al., "A corneal penetrating drug delivery system based on elastin-like polypeptide (1053.4)," The FASEB Journal, Apr. 1, 2014. 28 (1) p. 1053.4. 1 page. Abstract Only.

Blackburn, B.J., et al., "A review of structural and biomechanical changes in the cornea in aging, disease, and photochemical crosslinking," *Frontiers in bioengineering and biotechnology*, Mar. 29, 2019. 7: p. 1-16. 16 pages.

Branski, L.K., et al., "Gene therapy in wound healing: present status and future directions," *Gene Therapy*, 14, 2007. pp. 1-10. 10 pages. Website: doi.org/10.1038/sj.gt.3302837.

(Continued)

*Primary Examiner* — Michael P Cohen
(74) *Attorney, Agent, or Firm* — Steinfl + Bruno LLP

(57) ABSTRACT

Methods and systems and related particles and compositions that can be used to deliver a biologically active cargo such as a drug to a cornea of an individual, the delivery performed in a rapid, nonsurgical, and/or controllable fashion are described. Particularly, a method is described for controlled ballistic delivery of a cargo in a microparticle to the cornea of an individual, including a biologically active cargo.

18 Claims, 44 Drawing Sheets

(56) References Cited

OTHER PUBLICATIONS

Bykhovskaya, Y., et al., "Variation in the lysyl oxidase (LOX) gene is associated with keratoconus in family-based and case-control studies," *Invest Ophthalmol Vis Sci*, Jun. 2012. 53(7): p. 4152-7. 7 pages.
Campbell, L., "Under the hood: The physics of projectile ballistics," Downloaded on Dec. 9, 2021 from website: panoptesv.com/RPGs/Equipment/Weapons/Projectile_physics.php. 11 pages.
Caporossi, A., et al., "Long-term results of riboflavin ultraviolet a corneal collagen crosslinking for keratoconus in Italy: the Siena eye cross study," *Am J Ophthalmol*, 2010. 149(4): p. 585-93. 10 pages.
Chen, X.H., et al., "Direct growth of hydroxy cupric phosphate heptahydrate monocrystal with honeycomb-like porous structures on copper surface mimicking lotus leaf," *Crystal Growth and Design*, 2009. 9(6): p. 2656-2661. 7 pages.
Cifariello, F., et al., "Epi-off versus epi-on corneal collagen cross-linking in keratoconus patients: a comparative study through 2-year follow-up," *Journal of ophthalmology*, 2018. 7 pages.
Corporation, M.-S. Porous Silica. Downloaded on Dec. 9, 2021, from website: mo-sci.com/products/porous-silica/. 2021. 3 pages.
Czerner, M., et al., "Determination of Elastic Modulus of Gelatin Gels by Indentation Experiments" *Procedia Materials Science 8*. 2015. pp. 287-296. 10 pages.
Daull, P., et al., "Novasorb® Cationic Nanoemulsion and Latanoprost: The ideal combination for glaucoma management," *J Eye Dis Disord*, Jan. 26, 2017. 2 (1). 5 pages.
Dudakova, L., et al., "The impairment of lysyl oxidase in keratoconus and in keratoconus-associate disorders," *J Neural Transm* (*Vienna*), 2013. 120(6): p. 977-82. 7 pages.
Dwyer, T.J., et al., "Effects of treadmill exercise versus Flutter® on respiratory flow and sputum properties in adults with cystic fibrosis: a randomised, controlled, cross-over trial," *BMC Pulmonary Medicine*, 17:14. 2017. 8 pages.
Ehlers, N., et al., "The cornea: epithelium and stroma," *Advances in organ biology*, 2005. 10: p. 83-111. 30 pages.
Ferguson, J.E., et al., "Wireless communication with implanted medical devices using the conductive properties of the body," *Expert Rev Med Devices*, 8(4). Jul. 2011. pp. 427-433. 14 pages. doi: 10.1586/erd.11.16.
Gaudana, R., et al., "Ocular drug delivery," *The AAPS Journal*, Sep. 2010. 12(3): p. 348-360. 14 pages.
Gordon-Shaag, A., et al., "The genetic and environmental factors for keratoconus," *BioMed research international*, 2015. 795738, p. 24-32. 20 pages.
Gore, D.M., et al., "New clinical pathways for keratoconus," *Eye* (*Lond*), 2013. 27(3): p. 329-39. 12 pages.
Gouveia, S.M et al., "Human tear viscosity: an interactive role for proteins and lipids," *Biochimica et Biophysica Acta* (*BBA*)—*Proteins and Proteomics*, 2005. 1753(2): p. 155-163. 10 pages.
Guo, Q., et al., "Entanglement-based thermoplastic shape memory polymeric particles wit photothermal actuation for biomedical applications," *ACS applied materials & interfaces*, Mar. 30, 2018. 10(16): p. 13333-13341. 10 pages.
Hedbys, B.O., et al., "The thickness-hydration relationship of the cornea," *Experimental eye research*, 1966. 5(3): p. 221-228. 9 pages.
Hemmila, M.R., "Topical Nanoemulsion Therapy Reduces Bacterial Wound Infection and Inflammation Following Burn Injury," *Surgery*, vol. 148, No. 3. Sep. 2010. pp. 499-509. 12 pages.
Holsapple, J.S., et al., "Low Intensity Shockwave Treatment Modulates Macrophage Functions Beneficial to Healing Chronic Wounds," *Int. J. Mol. Sci.* 22, Jul. 22, 2021. 7844. 17 pages. Website: doi.org/10.3390/ijms22157844.
Huynh, J., "Factors governing photodynamic cross-linking of ocular coat," Thesis submitted to the California Institute of Technology. Defended May 6, 2011. 175 pages.
IUPAC Periodic Table of the Elements dated Jun. 22, 2007. Downloaded on Dec. 9, 2021, from https://old.iupac.org/reports/periodic_table/IUPAC_Periodic_Table-22Jun07b.pdf. 1 page.
Jackson, C.M., et al., "Defining and measuring biological activity: applying the principles of metrology," *Accreditation and quality assurance*, Published Online Mar. 16, 2007. 12(6): p. 283-294. 13 pages.
Jia, H.Z., et al., "Efficacy of iontophoresis-assisted epithelium-on corneal crosslinking for keratoconus," *International journal of ophthalmology*, Apr. 18, 2018. 11(4): p. 687. 9 pages.
Jussila, J., "Preparing ballistic gelatine—review and proposal for a standard method," *Forensic science international*, 2004. 141(2-3): p. 91-98. 9 pages.
Kasbekar, S.A., et al., "Corneal transplant surgery for keratoconus and the effect of surgeon experience on deep anterior lamellar keratoplasty outcomes," *Am J Ophthalmol*, 2014. 158(6): p. 1239-46. 9 pages.
Kendall, M., et al., "Intradermal ballistic delivery of microparticles into excised human skin for pharmaceutical applications," *Journal of biomechanics*, 2004. 37(11): p. 1733-1741. 10 pages.
Kendall, MAF, et al., "Transdermal ballistic delivery of microparticles: investigation into skin penetration," in *BS EMBS Int. Conf.*, Jul. 23-28, 2000. IEEE. 5 pages.
Kim, J.H., et al., "Chlorate and Antibiotic Treatment Dismantle Pseudomonas Aeruginosa Biofilm and Lead To Healing Of Chronic Wounds," *WHS Abstract Session List Key. Wound Rep Reg*, 29: A1-A53. 2021. Abstract Only. 2 pages. Website: doi.org/10.1111/wrr.12921.
King, M., "The Role of Mucus Viscoelasticity in Cough Clearance," *Biorheology*, vol. 24, No. 6, pp. 589-597, Jan. 1, 1987. DOI: 10.3233/BIR-1987-24611.12 pages.
Kwon, J., et al., "Compressive strain rate sensitivity of ballistic gelatin," *Journal of Biomechanics* 43. 2010. pp. 420-425. 6 pages.
Laccetti, B. and Kornfield J., "Ballistic delivery of compounds to inner layers of the cornea is limited by tough mechanical properties of stromal tissue," J Mech Behav Biomed Mater. Mar. 2021. 115:104246. doi: 10.1016/j.jmbbm.2020.104246. Epub Dec. 5, 2020. Abstract Only. 1 page.
Laccetti B., and Kornfield J., "Ballistic Delivery of Compounds to Inner Layers of the Cornea is Limited by Tough Mechanical Properties of Stromal Tissue," *Journal of the Mechanical Behavior of Biomedical Materials*, vol. 115, Mar. 2021, Journal Pre-Proof. 23 pages. 104246, ISSN 1751-6161.
Laccetti, B., "Therapeutic Microparticles and Biolistic Drug-Delivery to the Cornea," Dissertation (Ph.D.), California Institute of Technology. 2021. 226 pages. doi:10.7907/nf29-gy82. https://resolver.caltech.edu/CaltechTHESIS:10182020-133113205.
Last, J.A., et al., "Compliance profile of the human cornea as measured by atomic force microscopy," *Micron*, 2012. 43(12): p. 1293-1298. 7 Pages.
Lavars, N., "World's smallest single-chip system can be injected into the body," News Atlas, Published May 11, 2021. Downloaded Dec. 9, 2021, from website: newatlas.com/electronics/worlds-smallest-single-chip-system-injectable/. 10 pages.
Lindblad, N.R., et al., "Production of uniform-sized liquid droplets," *Journal of Scientific Instruments*, 1965. 42(8): p. 635. 6 pages.
Ling, Y., et al., "Tungsten carbide hollow microspheres with robust and stable electrocatalytic activity toward hydrogen evolution reaction," *ACS Omega*, Feb. 26, 2019. 4(2): p. 4185-4191. 8 pages.
Ma, X., et al., "Cryopreservation: Organ Preservation, in Comprehensive Biotechnology," (Second Edition), *Academic Press.*, 2011. p. 83-98. 17 pages.
Marchini, M., et al., "Differences in the fibril structure of corneal and tendon collagen. An electron microscopy and X-ray diffraction investigation," *Connective tissue research*, 1986. 15(4): p. 269-281. 15 pages.
Mattson, M., et al., "Mechanical measurements of sclera for screening myopia treatments," *Investigative Ophthalmology & Visual Science*, May 2005. 46(13): p. 1991-1991. 3 pages.
Mazzotta, C., et al., "Stromal haze after combined riboflavin-UVA corneal collagen crosslinking in keratoconus: in vivo confocal microscopic evaluation," *Clin Experiment Ophthalmol*, 2007. 35(6): p. 580-2. 6 pages.

(56) References Cited

OTHER PUBLICATIONS

Nickerson, C.S., et al., "A "cleat" geometry for suppressing wall slip," *Journal of Rheology*, 2005. 49(4): p. 865-874. 12 pages.
"Software estimates Chemical, Physical Properties," Chemical and Engineering News, 63(5), 1985. p. 27. 2 pages.
Olivares Jimenez, J.L., et al., "Keratoconus: age of onset and natural history," *Optom Vis Sci*, Mar. 1997. 74(3): p. 147-51. 7 pages.
Pasumarthy, R.K.A., et al., "Mechanical and optical characterization of a tissue surrogate polymer gel," Polymer Testing 55. Available online Sep. 2, 2016. 219-229. 11 pages.
Pollard, A.M., et al., "Synthesis and stabilities of the basic copper (II) chlorides atacamite, paratacamite and botallackite," *Mineralogical magazine*, Dec. 1989. 53(373): p. 557-563. 8 pages.
Rebenitsch, R.L., et al., "The lifetime economic burden of keratoconus: a decision analysis using a markov model," *AM J Ophthalmol*, 2011. 151(5): p. 768-773 e2. 9 pages.
Ribeiro, M.D.M., et al., "The effect of adding oleic acid in the production of stearic acid lipid microparticles with a hydrophilic core by a spray-cooling process," *Food Research International*, 2012. 47(1): p. 38-44. 8 pages.
Ringberg, D., et al., "Pneumatic capillary gun for ballistic delivery of microparticles," *Applied Physics Letters* 87(1), Feb. 2005. 8 pages.
Segletes, S.B., "Modeling the penetration behavior of rigid spheres into ballistic gelatin," *Army Research Lab Aberdeen Proving Ground Md.*, Mar. 2008. 37 pages.
Shariati, A., et al., "The Effects of Davidson's Fixative Solution in Preserving the Rabbit Eye," *Investigative Ophthalmology & Visual Science*, May 2008. 49(13): p. 5207-5207. 2 pages. Abstract Only.
Sharma, A., et al., "Strain-controlled criticality governs the nonlinear mechanics of fibre networks," *Nature Physics*, Jan. 25, 2016. 12(6): p. 584-587. 6 pages.
Shetty, R., et al., "Attenuation of lysyl oxidase and collagen gene expression in keratoconus patient corneal epithelium corresponds to disease severity," *Mol Vis*, Jan. 12, 2015. 21: p. 12-25. 15 pages.
Shi, C., et al., "Application of a sub-0.1-mm3 implantable mote for in vivo real-time wireless temperature sensing," *Science Advances*, 7(19). May 7, 2021. 10 pages. DOI: 10.1126/sciadv.abf6312.
Swain, M., et al., "Projectile penetration into ballistic gelatin," *Journal of the mechanical behavior of biomedical materials*, 2014. 29: p. 385-392. 9 pages.
Thomasy, S.M., et al., "Elastic modulus and collagen organization of the rabbit cornea: epithelium to endothelium," *Acta biomaterialia*, 2014. 10(2): p. 785-791. 8 pages.
Veysset, D., et al., "High-velocity micro-particle impact on gelatin and synthetic hydrogel," *Journal of the mechanical behavior of biomedical materials*, Published Online Jun. 14, 2018. 86: p. 71-76. 7 pages.
Vinciguerra, P., et al., "Refractive, topographic, tomographic, and aberrometric analysis of keratoconic eyes undergoing corneal cross-linking," *Ophthalmology*, 2009. 116(3): pp. 369-378.
Vinciguerra, R., et al., "Corneal cross-linking as a treatment for keratoconus: four-year morphologic and clinical outcomes with respect to patient age," *Ophthalmology*, 2013. 120(5): p. 908-16. 11 pages.
Warner, R.R., et al., "Electron probe analysis of human skin: determination of the water concentration profile," *Journal of Investigative Dermatology*, 1988. 90(2): p. 218-224. 8 pages.
Webb, P.A., "Volume and density determinations for particle technologists," Micromeritics Instrument Corp. Downloaded on Dec. 9, 2021 from website: www.micromeritics.com/Repository/Files/Volume_and_Density_determinations_for_Particle_Technologists.pdf, 2001: p. 1-16. 16 pages.
Wikipedia. Ballistic gelatin, Downloaded on Dec. 9, 2021 from https://web.archive.org/web/20181222100214/https://en.wikipedia.org/wiki/Ballistic_gelatin. 2018. 3 pages.
Wikipedia. Epithelium. Downloaded on Dec. 9, 2021, from website: web.archive.org/web/20190325184737/https://en.wikipedia.org/wiki/Epithelium . 2019. 11 pages.
Wikipedia. Polymer. Downloaded on Dec. 9, 2021, from: website: web.archive.org/web/20191212045342/https://en.wikipedia.org/wiki/Polymer. 2019. 14 pages.
Wikipedia. Porous glass. Downloaded on Dec. 9, 2021, from: website: web.archive.org/web/20200612145638/https://en.wikipedia.org/wiki/Porous_glass. 2020. 4 pages.
Wikipedia. Tissue (biology). Downloaded on Dec. 9, 2021 from website: web.archive.org/web/20191201005711/https://en.wikipedia.org/wiki/Tissue_(biology). 2019. 7 pages.
Xiong, C., et al., "Mass, size, and density measurements of microparticles in a quadrupole ion trap," *Analytical Chemistry*, 2019. 91(21): p. 13508-13513. 7 pages.
Zamora, K.V., et al., "Polymicrobial keratitis after a collagen cross-linking procedure with postoperative use of a contact lens: a case report," *Cornea*, May 2009. 28(4): p. 474-6. 5 pages.
Zayas, J.G., et al., "Bronchial Mucus Properties in Lung Cancer: Relationship with Site of Lesion," *Canadian respiratory journal: journal of the Canadian Thoracic Society* 6(3):246-52. 1999. 8 pages DOI:10.1155/1999/459084.
Zia, R.N., "Active and Passive Microrheology: Theory and Simulation," *Annu. Rev. Fluid Mech.* Jan. 2018. 50:371-405. 37 pages.
Zilony, N., et al., "Bombarding cancer: biolistic delivery of therapeutics using porous Si carriers," *Scientific reports*, Aug. 26, 2013. 3(1): p. 1-6. 7 pages.
Aslan, N. et al., Fabrication of porous-Ti6Al4V alloy by using hot pressing technique and Mg space holder for hard-tissue biomedical applications. Journal of Materials Science: Materials in Medicine, vol. 32, Article No. 80, (2021), 12 pages.
Mitchell, T. et al. 2003. A ballistic study of micro-particle penetration of the oral mucosa. Int. J. Impact Eng. 28, 581-599.
Mohanty, C. and S.K. Sahoo, Curcumin and its topical formulations for wound healing applications. Drug Discovery Today, Oct. 2017. 22(10): p. 1582-1592.
Mohsen, A., Khalaf, A., et al., Antibacterial, anti-biofilm activity of some non-steroidal anti-inflammatory drugs and N-acetyl cysteine against some biofilm producing uropathogens. American Journal of Epidemiology, 2015. 3(1): p. 1-9.
Moore, K., et al., Prediction and monitoring the therapeutic response of chronic dermal wounds. International wound journal, 2006. 3(2): p. 89-96.
Mo-Sci "Porous Silica", 3 pages. Retrieved from the Wayback Machine for Dec. 7, 2022. Website: mo-sci.com/products/porous-silica/.
Mudge, B.P., et al., Role of glutathione redox dysfunction in diabetic wounds. Wound Repair and Regeneration, 2002. 10(1): p. 52-58.
Mukai, K., et al., Effectiveness of Changing the Application of Japanese Honey to a Hydrocolloid Dressing in Between the Inflammatory and Proliferative Phases on Cutaneous Wound Healing in Male Mice. Wounds: a compendium of clinical research and practice, 2016. 29(1): p. 1-9.
Musalmah, M., et al., Comparative effects of palm vitamin E and a-tocopherol on healing and wound tissue antioxidant enzyme levels in diabetic rats. Lipids, Jun. 2005. 40(6): p. 575-580.
National Eye Institute, "How the Eyes Work," Updated Apr. 20, 2022. 2 pages. Website: www.nei.nih.gov/learn-about-eye-health/healthy-vision/how-eyes-work.
Nery, R.A., et al., Uric acid and tissue repair. ABCD. Arquivos Brasileiros de Cirurgia Digestiva (Sao Paulo), 2015. 28(4): p. 290-292.
NetCE, "Disorders and Injuries of the Eye and Eyelid," Released Dec. 1, 2023. 97 pages. Website: www.netce.com/coursecontent.php?courseid=2715.
Niaz, K., et al., Health benefits of manuka honey as an essential constituent for tissue regeneration. Current drug metabolism, 2017. 18(10): p. 881-892.
Nurkesh, Ayan et al. "Recent advances in the controlled release of growth factors and cytokines for improving cutaneous wound healing". Frontiers in Cell and Development Biology 8 (Jul. 2020): 638. p. 1-7.
Pailler-Mattei, C., S. Bec, and H. Zahouani. "In vivo measurements of the elastic mechanical properties of human skin by indentation tests." Medical Engineering &Pphysics, 30 (5) (2008): 599-606.

(56) References Cited

OTHER PUBLICATIONS

Panchatcharam, M., et al., Curcumin improves wound healing by modulating collagen and decreasing reactive oxygen species. Molecular and cellular biochemistry, 2006. 290(1): p. 87-96.
Papanas, N. et al. Benefit-risk assessment of becaplermin in the treatment of diabetic foot ulcers. Drug Safety: An International Journal of Medical Toxicology and Drug Experience, (2010), 33, pp. 455-461.
Park, Yoon Jeong et al. "Controlled release of platelet-derived growth factor from porous poly (L-lactide) membranes for guided tissue regeneration". Journal of Controlled Release 51 (1998): 201-211.
Patel, G.K., The role of nutrition in the management of lower extremity wounds. The international journal of lower extremity wounds, 2005. 4(1): p. 12-22.
Paterson, R.L., H.F. Galley, and N.R. Webster, The effect of N-acetylcysteine on nuclear factor-KB activation, interleukin-6, interleukin-8, and intercellular adhesion molecule-I expression in patients with sepsis. Critical care medicine, 2003. 31(11): p. 2574-2578.
Pelikan, E.W., Pharmacology Glossary. Boston University, Chobanian & Avedisian School of Medicine. 62 pages (2022).
Percival, N.J., Classification of wounds and their management. Surgery (Oxford), 2002. 20(5): p. 114-117.
Peshenko, I.V. and H. Shichi, Oxidation of active center cysteine of bovine 1-Cys peroxiredoxin to the cysteine sulfenic acid form by peroxide and peroxynitrite. Free Radical Biology and Medicine, 2001. 31(3): p. 292-303.
Petersen Shay, K., et al., Is a-lipoic acid a scavenger of reactive oxygen species in vivo? Evidence for its initiation of stress signaling pathways that promote endogenous antioxidant capacity. IUBMB life, Jun. 2008. 60(6): p. 362-367.
Phoenix Society for Burn Survivors, "Understanding the Healing Stages of a Burn Wound," Sep. 13, 2022. 11 pages. Website: www.phoenix-society.org/resources/understanding-the-healing-stages-of-a-burn-wound.
Pierce, G., et al., Platelet-derived growth factor-BB and transforming growth factor beta1 Selectively modulate glycosaminoglycans, collagen, and myofibroblasts in excisional wounds. The American journal of pathology, Mar. 1991. 138(3): p. 629-646.
Pierce, G.F., et al., Transforming growth factor beta reverses the glucocorticoid-induced wound-healing deficit in rats: possible regulation in macrophages by platelet-derived growth factor. Proceedings of the National Academy of Sciences, Apr. 1989. 86(7): p. 2229-2233.
Pugliese, Peter T. "The skin's antioxidant systems." Dermatology nursing, 10 (6)(Dec. 1998): 401-416. 24 pages.
Raftos, J.E., et al., Kinetics of uptake and deacetylation of N-acetylcysteine by human erythrocytes. The international journal of biochemistry & cell biology, 2007. 39(9): p. 1698-1706.
Rago, T. et al., Elastography: New Developments in Ultrasound for Predicting Malignancy in Thyroid Nodules. The Journal of Clinical Endocrinology & Metabolism, 92 (8); 2917-2922. Published online Jun. 5, 2007.
Ram, M., et al., Antioxidant potential of bilirubin-accelerated wound healing in streptozotocin-induced diabetic rats. Naunyn-Schmiedeberg's archives of pharmacology, Jun. 2014. 387(10): p. 955-961. 10 pages.
Ram, M., et al., Bilirubin modulated cytokines, growth factors and angiogenesis to improve cutaneous wound healing process in diabetic rats. International immunopharmacology, 2016. 30:p. 137-149.
Rasik, A.M. and A. Shukla, Antioxidant status in delayed healing type of wounds. International journal of experimental pathology, 2000. 81(4): p. 257-263.
Rojas, A.I. and T.J. Phillips, Patients with chronic leg ulcers show diminished levels of vitamins A and E, carotenes, and zinc. Dermatologic Surgery, Aug. 1999. 25(8): p. 601-604.
Rothe, M. and V. Falanga, Growth factors: their biology and promise in dermatologic diseases and tissue repair. Archives of dermatology, Oct. 1989. 125(10): p. 1390-1398.
Russell, L., Understanding physiology of wound healing and how dressings help. British journal of nursing, 2000. 9(1): p. 10-21.
Sartelli M, et al., 2018 "WSES/SIS-E consensus conference: recommendations for the management of skin and soft-tissue infections", World Journal of Emergency Surgery, (2018) 13: 58. 24 pages. Website: doi.org/10.1186/s13017-018-0219-9.
Scales, B.S. and Huffnagle, G.B., "The microbiome in wound repair and tissue fibrosis." The Journal of Pathology, 229 (2), (2013): 323-331.
Schaefer, M. and S. Werner, Oxidative stress in normal and impaired wound repair. Pharmacological research, 2008. 58(2): p. 165-171.
Schreml, S., et al., Luminescent dual sensors reveal extracellular pH-gradients and hypoxia on chronic wounds that disrupt epidermal repair. Theranostics, 2014. 4(7): p. 721-735.
Scott, R. 2011. The injured eye. Philos. Trans. R. Soc. B Biol. Sci. 366, 251-260.
Sen, C.K. and S. Roy, Redox signals in wound healing. Biochimica et Biophysica Acta (BBA)—General Subjects, Nov. 2008. 1780(11): p. 1348-1361. 23 pages.
Shakespeare, P., Burn wound healing and skin substitutes. Burns, 2001. 27(5): p. 517-522.
Shukla, A., A.M. Rasik, and G.K. Patnaik, Depletion of reduced glutathione, ascorbic acid, vitamin E and antioxidant defence enzymes in a healing cutaneous wound. Free Radical Research, 1997. 26(2): p. 93-101.
Smiell, J.M., et al., Efficacy and safety of becaplermin (recombinant human platelet-derived growth factor-BB) in patients with nonhealing, lower extremity diabetic ulcers: a combined analysis of four randomized studies. Wound Repair and Regeneration, (Sep. 1999). 7(5): p. 335-346.
Smith, Karen, et al. "One step closer to understanding the role of bacteria in diabetic foot ulcers: characterising the microbiome of ulcers." BMC Microbiology, 16 (54), (2016): 1-12.
Spiller, Kara L. et al. "A novel method for the direct fabrication of growth factor-loaded microspheres within porous nondegradable hydrogels: controlled release for cartilage tissue engineering". Journal of Controlled Release 157.1 (2012): 39-45.
Steenfos, H.H., Growth factors and wound healing. Scandinavian journal of plastic and reconstructive surgery and hand surgery, 1994. 28(2): p. 95-105.
Strodtbeck, F., Physiology of wound healing. Newborn Infants Nurs Rev, Mar. 2001. 1: p. 43-52.
Suzuki, T. and M. Yamamoto, Stress-sensing mechanisms and the physiological roles of the Keap1-Nrf2 system during cellular stress. Journal of Biological Chemistry, Aug. 2017. 292(41): p. 16817-16824.
Taeko, M., et al., "Wound Healing and Skin Regeneration", Cold Spring Harb Perspect Med 2015; 5:a023267; p. 1-12.
Tanelian, D.L., et al. Sep. 1997. Controlled gene gun delivery and expression of DNA within the cornea. Biotechniques 23, 484-488.
Taylor, R. and T. James, The role of oxidative stress in the development and persistence of pressure ulcers, in Pressure ulcer research. 2005, Springer. p. 205-232.
Taylor, T., et al., Ascorbic acid supplementation in the treatment of pressure-sores. The Lancet, Sep. 1974. 304(7880): p. 544-546.
Ten Dijke, P. and K.K. Iwata, Growth factors for wound healing. Bio/Technology, Aug. 1989. 7(8): p. 793-798.
Tenhunen, R., H.S. Marver, and R. Schmid, The enzymatic conversion of heme to bilirubin by microsomal heme oxygenase. Proceedings of the National Academy of Sciences of the United States of America, 1968. 61(2): p. 748-755.
Tsai, M.-L., et al., Topical N-acetylcysteine accelerates wound healing in vitro and in vivo via the PKC/Stat3 pathway. International journal of molecular sciences, 2014. 15(5): p. 7563-7578.
UCSF Department of Surgery, "Debridement", 2024. 5 pages. urgery.ucsf.edu/conditionsprocedures/debridement.asp.
Uruno, A., Y. Yagishita, and M. Yamamoto, The Keap1-Nrf2 system and diabetes mellitus. Archives of biochemistry and biophysics, Jan. 2015. 566: p. 76-84.

(56) References Cited

OTHER PUBLICATIONS

Vervaart, P. and K. Knight, Oxidative stress and the cell. Clinical Biochemist Reviews, Feb. 1996. 17: p. 3-16.

Veysset, D. et al. 2020. Laser-driven high-velocity microparticle launcher in atmosphere and under vacuum. Int. J. Impact Eng. 137. 8 pages.

VisionGain. Advanced wound care: world market prospects 2011-2021. Downloaded through the Wayback Machine, dated Aug. 17, 2012. 11 pages. (Website: www.visiongain.com/Report/716/Advanced-Wound-Care-World-Market-Prospects-2011-2021. Accessed Oct. 31, 2012).

Vogel, Benjamin et al. Determination of collagen content within picrosirius red stained paraffin-embedded tissue sections using fluorescence microscopy, MethodsX, (2015), 124-134.

Waasdorp, M. et al., "The Bigger Picture: Why Oral Mucosa Heals Better Than Skin", Biomolecules, (Aug. 6, 2021), 11, 1165. 22 pages. Website: doi.org/10.3390/biom11081165.

Wachter, K.C. et al., Muscle Damping Measured with a Modified Pendulum Test in Patients with Fibromyalgia, Lumbago, and Cervical Syndrome. Spine, (1996), vol. 21, No. 18, pp. 2137-2142.

Wallace, E., Feeding the wound: nutrition and wound care. British Journal of Nursing, 1994. 3(13): p. 662-667.

Wellman, P.S., Howe, R.D., Dalton, E., and Kern K.A., Breast Tissue Stiffness in Compression is Correlated to Histological Diagnosis, (1999), 15 pages.

Wieman, TJ. Clinical efficacy of becaplermin (rhPDGF-BB) gel. Becaplermin gel studies group. American Journal of Surgery 176, 74S-79S (Aug. 1998).

Wieman, TJ, et al. Efficacy and safety of a topical gel formulation of recombinant human platelet-derived growth factor-bb (becaplermin) in patients with chronic neuropathic diabetic ulcers. A phase III randomized placebo-controlled double-blind study. Diabetes Care, (May 1998), 21, pp. 822-827.

Wikipedia. Steroid. Downloaded for Nov. 11, 2022. 20 pages. Website: web.archive.org/web/20221111004859/https://en.wikipedia.org/wiki/Steroid. 2022.

Wiseman, H., Vitamin D is a membrane antioxidant. Ability to inhibit iron-dependent lipid peroxidation in liposomes compared to cholesterol, ergosterol and tamoxifen and relevance to anticancer action. FEES letters, Jul. 1993. 326(1-3): p. 285-288.

Wlaschek, M. and K. Scharffetter-Kochanek, Oxidative stress in chronic venous leg ulcers. Wound Repair and Regeneration, 2005. 13(5): p. 452-461.

Wolcott, R. et al., Microbiota is a primary cause of pathogenesis of chronic wounds. Journal of Wound Care, North American supplement, vol. 25, No. 10, Oct. 2016. S33-S43.

Wolcott, R.D., et al., Analysis of the chronic would microbiota of 2,963 patients by 16S rDNA pyrosequencing. Wound Repair and Regeneration. (2016), 24, 163-174.

Wood, Z.A., et al., Structure, mechanism and regulation of peroxiredoxins. Trends in biochemical sciences, Jan. 2003. 28(1): p. 32-40.

Yang, C., et al., Rapamycin and mTOR inhibitors probably have therapeutic effects for post-operative cognitive dysfunction. Medical hypotheses, 2013. 81(3): p. 487-488.

Yang, H., J. Chai, and Z. Guo, Effect of improved topical agents on healing time of deep second-degree burn wound. Zhongguo xiu fu chong jian wai ke za zhi= Zhongguo xiufuchongjian waike zazhi= Chinese journal of reparative and reconstructive surgery, 2001. 15(3): p. 162-164. Chinese original with English Abstract.

Yang, Zhaoyang et al. "The effect of the dosage of NT-3/chitosan carriers on the proliferation and differentiation of neural stem cells". Biomaterials 31.18 (2010): 4846-4854.

Ye, S.J. et al. "Penetration dynamics of steel spheres into a ballistic gelatin: Experiments, nondimensional analysis, and finite element modeling", International Journal of Impact Engineering, vol. 162, (2022), 104144, 10 pages. ISSN 0734-743X, Website: doi.org/10.1016/j.ijimpeng.2021.104144.

Yoshida, T., et al., The involvement of thioredoxin and thioredoxin binding protein-2 on cellular proliferation and aging process. Annals-New York Academy of Sciences, 2005. 1055: p. 1-12.

Zhang, Dongwei, Diganta B. Das, and Chris D. Rielly. "Potential of microneedle-assisted micro-particle delivery by gene guns: a review." Drug delivery 21 (8), (2014): 571-587.

Zhang, E.P. et al. 2002. Minimizing side effects of ballistic gene transfer into the murine corneal epithelium. Graefe's Arch. Clin. Exp. Ophthamol. 240, 114-119.

Zhang, W et al. 2017. Experimental investigation on ballistic stability of high-speed projectile in sand. AIP Conf. Proc. 1793. 5 pages.

Zhang, Y. et al. "Drug-induced regeneration in adult mice". Science Translational Medicine, (Jun. 2015), 7 (290), 290ra92. 11 pages. Website: doi.org/10.1126/scitranslmed.3010228.

Zhao, Hai-yang et al. "Research Advances in Tissue Engineering Materials for Sustained Release of Growth Factors" BioMed Research International, vol. 2015, Article ID 808202, 7 pages, 2015. Website: doi.org/10.1155/2015/808202.

Zheng, H., et al., Therapeutic potential of Nrf2 activators in streptozotocin-induced diabetic nephropathy. Diabetes, Nov. 2011. 60(11): p. 3055-3066.

Ziol, M. et al., Noninvasive Assessment of Liver Fibrosis by Measurement of Stiffness in Patients with Chronic Hepatitis C., Hepatology, vol. 41, No. 1, (Jan. 2005), pp. 48-54.

Adamson, B., et al., Delayed repair: the role of glutathione in a rat incisional wound model. Journal of Surgical Research, 1996. 62(2): p. 159-164.

Agren, M.S., et al., A randomized, double-blind, placebo-controlled multicenter trial evaluating topical zinc oxide for acute open wounds following pilonidal disease excision. Wound repair and regeneration, 2006. 14(5): p. 526-535.

Agren, M.S., Studies on zinc in wound healing. Acta Derm Venereal Suppl 1990. 154: p. 1-36.

Aihara, M., et al., Effects of N-acetylcysteine and ambroxol on the production of IL-12 and IL-10 in human alveolar macrophages. Respiration, 2000. 67(6): p. 662-671.

Alvarez-Suarez, J.M., et al., The composition and biological activity of honey: a focus on Manuka honey. Foods, Sep. 2014. 3(3): p. 420-432.

Amar, M. R.S., A Thesis: "Estimation of Mechanical Properties of Soft Tissue Subjected to Dynamic Impart", Dec. 2010, Presented to the Faculty of The Graduate College at the University of Nebraska. 67 pages.

Armstrong, S. and C. Ruckley, Use of a fibrous dressing in exuding leg ulcers. Journal of Wound Care, 1997. 6(7): p. 322-324.

Bao, P., et al., The role of vascular endothelial growth factor in wound healing. Journal of Surgical Research, 2009. 153(2): p. 347-358.

Baranano, D.E., et al., Biliverdin reductase: a major physiologic cytoprotectant. Proceedings of the national academy of sciences, Dec. 10, 2002. 99 (25): p. 16093-16098.

Baumann, L.S. and J.S. Md, The effects of topical vitamin E on the cosmetic appearance of scars. Dermatologic Surgery, 1999. 25(4): p. 311-315.

Beck, L.S., et al., One systemic administration of transforming growth factor-beta 1 reverses age-or glucocorticoid-impaired wound healing. The Journal of clinical investigation, 1993. 92(6): p. 2841-2849.

Bernard, G., et al., Effect of N-acetylcysteine on the pulmonary response to endotoxin in the awake sheep and upon in vitro granulocyte function. The Journal of clinical investigation, Jun. 1984. 73(6): p. 1772-1784.

Biagio Manna, Phillip Nahirniak, Christopher A. Morrison, *Wound Debridement*,. StatPearls Publishing. Retrieved through the Wayback Machine for Dec. 7, 2022. Website: web.archive.org/web/20221207131130/https://www.ncbi.nlm.nih.gov/books/NBK507882/.

Boateng J., et al., "Advanced Therapeutic Dressings For Effective Wound Healing," Journal of Pharmaceutical Sciences. 2015. 80 pages. DOI: 10.1002/JPS.24610.

(56) References Cited

OTHER PUBLICATIONS

Boateng, J.S., et al., Wound healing dressings and drug delivery systems: a review. Journal of pharmaceutical sciences, Aug. 2008. 97(8): p. 2892-2923.
Bolton, L. and L. Van Rijswijk, Wound dressings: meeting clinical and biological needs. Dermatology nursing, 1991. 3(3): p. 146-161.
Brown, GL, et al. "Enhancement of wound healing by topical treatment with epidermal growth factor". The New England Journal of Medicine, (Jul. 1989), 321, pp. 76-79.
Calabrese, V., et al., Curcumin and the cellular stress response in free radical-related diseases. Molecular nutrition & food research, 2008. 52(9): p. 1062-1073.
Camodeca, A. et al. Last Updated: Apr. 17, 2023. Corneal foreign body. StatPearls 2024. 7 pages.
Cano Sanchez, M., et al., Targeting oxidative stress and mitochondrial dysfunction in the treatment of impaired wound healing: a systematic review. Antioxidants, Jul. 2018. 7(8): p. 98. 14 pages.
Chedid, M., et al., Glucocorticoids inhibit keratinocyte growth factor production in primary dermal fibroblasts. Endocrinology, 1996. 137(6): p. 2232-2237.
Chen, J. et al. "Biomechanics of oral mucosa", J. R. Soc. Interface, (2015), 12: Mar. 25, 2015. 20 pages. Website: dx.doi.org/10/1098/rsif.20115.0325.
Chen, W.J., A.A. Rogers, and M.J. Lydon, Characterization of biologic properties of wound fluid collected during early stages of wound healing. Journal of Investigative Dermatology, 1992. 99(5): p. 559-564.
Chigurupati, S., et al., A synthetic uric acid analog accelerates cutaneous wound healing in mice. PLoS One, Apr. 2010. 5(4): p. e10044. pp. 1-10.
Choi, S.M., et al., Development of stabilized growth factor-loaded hyaluronate-collagen dressing (HCD) matrix for impaired wound healing. Biomaterials Research, 2016. 20(9): p. 1-7.
Choi, S.M., et al., Effects of structurally stabilized EGF and bFGF on wound healing in type I and type II diabetic mice. Acta biomaterialia, 2018. 66: p. 325-334.
Cooper, DM., Wound healing: New understandings. Nurs Pract Forum, 1999. 10: p. 74-86.
Cotgreave, I., P. Moldeus, and I. Schuppe, The metabolism of N-acetylcysteine by human endothelial cells. Biochemical pharmacology, 1991. 42(1): p. 13-16.
Da Rocha, R.P., et al., Effects of a vitamin pool (vitamins A, E, and C) on the tissue necrosis process: experimental study on rats. Aesthetic plastic surgery, 2002. 26(3): p. 197-202.
Dowd, Scot E., et al. "Polymicrobial nature of chronic diabetic foot ulcer biofilm infections determined using bacterial tag encoded FLX amplicon pyrosequencing (bTEFAP)." PloS one, vol. 3, Issue 10 (Oct. 2008): e3326. 7 pages.
Dowd, Scot E., et al. "Survey of bacterial diversity in chronic wounds using pyrosequencing, DGGE, and full ribosome shotgun sequencing." BMC microbiology 8 (43), (Mar. 2008): 1-15.
Eaglstein, W.H., et al., Optimal use of an occlusive dressing to enhance healing: Effect of delayed application and early removal on wound healing. Archives of dermatology, Mar. 1988. 124(3): p. 392-395.
Ehrlich, H.P., H. Tarver, and T.K. Hunt, Effects of vitamin A and glucocorticoids upon inflammation and collagen synthesis. Annals of surgery, 1973. 177(2): p. 222-227.
Elcin, Y.M., V. Dixit, and G. Gitnick, Extensive in vivo angiogenesis following controlled release of human vascular endothelial cell growth factor: implications for tissue engineering and wound healing. Artificial organs, 2001. 25(7): p. 558-565.
Evans, N.D et al., "Epithelial mechanobiology, skin wound healing, and the stem cell niche", Journal of the Mechanical Behavior of Biomedical Materials, 28 (2013) pp. 397-409. Website: www.sciencedirect.com/science/article/pii/S1751616113001550.
Fang, R.C. and R.D. Galiano, A review of becaplermin gel in the treatment of diabetic neuropathic foot ulcers. Biologics: targets & therapy, 2008. 2(1): p. 1-12.
Feng, X. et. al., "In vivo stiffness measurement of epidermis, dermis, and hypodermis using broadband Rayleigh-wave optical coherence elastography," Acta Biomater. Available online Apr. 2022 1:146:295-305. doi: 10.1016/j.actbio.2022.04.030.
Ferguson, MW et al. Prophylactic administration of avotermin for improvement of skin scarring: three double-blind, placebo-controlled, phase I/II studies. Lancet, (2009), 373, pp. 1264-1274.
Ferreira, M.C., et al., Complex wounds. Clinics, 2006. 61(6): p. 571-578.
Fitzmaurice, S., R.K. Sivamani, and R.R. Isseroff, Antioxidant therapies for wound healing: a clinical guide to currently commercially available products. Skin pharmacology and physiology, 2011. 24(3): p. 113-126.
Flanigan, K.H., Nutritional aspects of wound healing. Advances in wound care: the journal for prevention and healing, 1997. 10(3): p. 48-52.
Gabriel, Allen, MD. "Wound Healing and Growth Factors". Overview, Types of Would Healing, Phases of Wound Healing. Medscape, Aug. 27, 2021, http://emedicine.medscape.com/article/1298196-overview#a3.
Garcia-Orue, I., et al., Novel nanofibrous dressings containing rhEGF and Aloe vera for wound healing applications. International journal of pharmaceutics, 2017. 523(2): p. 556-566.
Gardner, Sue E., Stephen L. Hillis, Kris Heilmann, Julia A. Segre, Elizabeth A. Grice; The Neuropathic Diabetic Foot Ulcer Microbiome Is Associated With Clinical Factors. Diabetes, Mar. 2013; 62 (3): 923-930. Website: doi.org/10.2337/db12-0771.
Gilliland, E.L., et al., Bacterial colonisation of leg ulcers and its effect on the success rate of skin grafting. Annals of the Royal College of Surgeons of England, 1988. 70(2): p. 105-108.
Gjodsbol, Kristine, et al. "Multiple bacterial species reside in chronic wounds: a longitudinal study." International Wound Journal, vol. 3. No. 3 (2006): 225-231.
Gjodsbol, Kristine, et al. "No need for biopsies: comparison of three sample techniques for wound microbiota determination." International Wound Journal 9 (3) (2012): 295-302.
Godoy-Gallardo M, Portolés-Gil N, López-Periago AM, Domingo C, Hosta-Rigau L. Immobilization of BMP-2 and VEGF within Multilayered Polydopamine-Coated Scaffolds and the Resulting Osteogenic and Angiogenic Synergy of Co-Cultured Human Mesenchymal Stem Cells and Human Endothelial Progenitor Cells. International Journal of Molecular Sciences. 2020; 21(17):6418. https://doi.org/10.3390/ijms21176418.
Gomes, F., et al., Farnesol in combination with N-acetylcysteine against *Staphylococcus epidermidis* planktonic and biofilm cells. Brazilian Journal of Microbiology, 2012. 43(1): p. 235-242.
Gontcharova, Viktoria, et al. "A comparison of bacterial composition in diabetic ulcers and contralateral intact skin." The Open Microbiology Journal, 4 (2010): 8-19.
Grandjean, E.M., et al., Efficacy of oral long-term N-acetylcysteine in chronic bronchopulmonary disease: a meta-analysis of published double-blind, placebo-controlled clinical trials. Clinical therapeutics, 2000. 22(2): p. 209-221.
Greenhalgh, D.G., et al., PDGF and FGF stimulate wound healing in the genetically diabetic mouse. The American journal of pathology, 1990. 136(6): p. 1235-1246.
Greenhalgh, D.G., The role of growth factors in wound healing. Journal of Trauma and Acute Care Surgery, 1996. 41(1): p. 159-167. 32 pages.
Gu, D.-1., et al., Adenovirus encoding human platelet-derived growth factor-B delivered in collagen exhibits safety, biodistribution, and immunogenicity profiles favorable for clinical use. Molecular therapy, 2004. 9(5): p. 699-711.
Gumus, K. et al. 2007. Corneal injury form a metallic foreign body: an occupational hazard. Eye Contact Lens 33, 259-260.
Hanschmann, E.-M., et al., Thioredoxins, glutaredoxins, and peroxiredoxins-molecular mechanisms and health significance: from cofactors to antioxidants to redox signaling. Antioxidants & redox signaling, 2013. 19(13): p. 1539-1605.
Harding, K., H. Morris, and G. Patel, Clinical review Healing chronic wounds. Br Med J, 2002. 324: p. 160-163.
Hareendran, A., et al., Measuring the impact of venous leg ulcers on quality of life. Journal of Wound Care, 2005. 14(2): p. 53-57.

(56) References Cited

OTHER PUBLICATIONS

Hart, A., et al., Sensory neuroprotection, mitochondrial preservation, and therapeutic potential of N-acetyl-cysteine after nerve injury. Neuroscience, 2004. 125(1): p. 91-101.
Hemilii, H. and R.M. Douglas, Vitamin C and acute respiratory infections. The international journal of tuberculosis and lung disease, 1999. 3(9): p. 756-761.
Hofmann, B., H.-J. Hecht, and L. Flohe, Peroxiredoxins. Biological chemistry, 2002. 383(3-4): p. 347-364.
Hori, Kunilo et al. "Controlled-release of epidermal growth factor form cationized gelatin hydrogel enhances corneal epithelial wound healing". Journal of Controlled Release 118 (2007): 169-176.
Hussain, Z., et al., Exploring recent developments to improve antioxidant, anti-inflammatory and antimicrobial efficacy of curcumin: A review of new trends and future perspectives. Materials science and engineering C, 2017. 77: p. 1316-1326.
Jagetia, G.C. and G. Rajanikant, Role of curcumin, a naturally occurring phenolic compound of turmeric in accelerating the repair of excision wound, in mice whole-body exposed to various doses of y-radiation. Journal of Surgical Research, 2004. 120(1): p. 127-138.
James, Garth A., et al. "Biofilms in chronic wounds." Wound Repair and regeneration 16 (1) (2008): 37-44.
Jeon, Oju et al. "Affinity-based growth factor delivery using biodegradable, photocrosslinked heparin-alginate hydrogels". Journal of Controlled Release 154 (2011): 258-266.
Jeon, Oju et al. "Photocrosslinked alginate hydrogels with tunable biodegradation rates and mechanical properties". Biomaterials 30 (2009): 2724-2734.
Jiang, T., et al., Nrf2 suppresses lupus nephritis through inhibition of oxidative injury and the NF-KB-mediated inflammatory response. Kidney international, Feb. 2014. 85(2): p. 333-343. 19 pages.
Jimi, S. et al. "Sequential Delivery of Cryogel Released Growth Factors and Cytokines Accelerates Wound Healing and Improved Tissue Regeneration" Frontiers in Bioengineering and Biotechnology, Apr. 2020, vol. 8, Article 345, 14 pages. Website: www.frontiersin.org.
Judith, R., et al., Application of a PDGF-containing novel gel for cutaneous wound healing. Life sciences, 2010. 87(1-2): p. 1-8.
Jull, A.B., et al., Honey as a topical treatment for wounds. Cochrane Database of Systematic Reviews, 2015 (3): p. Art. No. CD005083. 98 pages.
Khan, R.U., S. Naz, and A.M. Abudabos, Towards a better understanding of the therapeutic applications and corresponding mechanisms of action of honey. Environmental Science and Pollution Research, 2017. 24(36): p. 27755-27766.
Kietzmann, M. and M. Braun, Effects of the zinc oxide and cod liver oil containing ointment Zincojecol in an animal model of wound healing. DTW. Deutsche tierarztliche Wochenschrift, 2006. 113(9): p. 331-334. German Original with English Summary.
Klaesner, J.W. et al., Plantar Tissue Stiffness in Patients with Diabetes Mellitus and Peripheral Neuropathy. Arch Plys Med Rehabil, vol. 83, Dec. 2002, pp. 1796-1801.
Komarcevic, A., The modern approach to wound treatment. Medicinski pregled, 2000. 53(7-8): p. 363-368. Abstract Only.
Krasner, D., et al., The ABCs of wound care dressings. Wound management, 1993. pp. 66, 68-69, 72.
Kruger-Genge A et al., "Vascular Endothelial Cell Biology: An Update." *Int J Mol Sci*. Sep. 7, 2019; 20(18):4411. doi: 10.3390/ijms20184411. PMID: 31500313; PMCID: PMC6769656. 22 pages.
Kumin, A., et al., Peroxiredoxin 6 is a potent cytoprotective enzyme in the epidermis. The American journal of pathology, 2006. 169(4): p. 1194-1205.
Kundukad, B., et al., Mechanistic action of weak acid drugs on biofilms. Scientific reports, Jul. 2017. 7(1): p. 1-12.
Lansdown, A.B., Metallothioneins: potential therapeutic aids for wound healing in the skin. Wound repair and regeneration, 2002. 10(3): p. 130-132.
Lazarus, G.S., et al., Definitions and guidelines for assessment of wounds and evaluation of healing. Arch Dermatol, 1994. 130(4): p. 489-493.
Lee, A.-R.C., et al., Reversal of silver sulfadiazine-impaired wound healing by epidermal growth factor. Biomaterials, 2005. 26(22): p. 4670-4676.
Lin, Y.-J., et al., Stimulation of wound healing by PU/hydrogel composites containing fibroblast growth factor-2. Journal of Materials Chemistry B, 2015. 3(9): p. 1931-1941.
Lindberg, T., et al., A systematic review and meta-analysis of dressings used for wound healing: the efficiency of honey compared to silver on burns. Contemporary nurse, 2015. 51(2-3): p. 121-134.
Long, D.W., et al., Controlled delivery of platelet-derived proteins enhances porcine wound healing. Journal of Controlled Release, 2017. 253: p. 73-81.
Long, M., et al., An essential role of NRF2 in diabetic wound healing. Diabetes, Mar. 2016. 65(3): p. 780-793.
Loo, A.E.K., et al., Effects of hydrogen peroxide on wound healing in mice in relation to oxidative damage. PloS One, 2012. 7(11): p. e49215. 13 pages.
Lord, M.S., et al., Perlecan and vascular endothelial growth factor-encoding DNA-loaded chitosan scaffolds promote angiogenesis and wound healing. Journal of Controlled Release, 2017. 250: p. 48-61.
Lu, J. and A. Holmgren, The thioredoxin antioxidant system. Free Radical Biology and Medicine, 2014. 66: p. 75-87.
Lu, WN et al. 2003. Gene transfer into corneal endothelial cells by Helios gene gun. Nihon. Ganka Gakkai Zasshi 107, 189-195. Abstract only.
Mahmoud, M., et al., "Porous Glass Microspheres from Alkali-Activated Fiber Glass Waste." *Materials* 2022, 15, 1043. 9 pages. doi.org/10.3390/ma15031043.
Mandla, S., L. Davenport Huyer, and M. Radisic, Multimodal bioactive material approaches for wound healing. APL bioengineering, 2018. 2(2): p. 021503. 13 pages.
Mann, A., et al. Granulocyte-macrophage colony-stimulating factor is essential for normal wound healing. in Journal of Investigative Dermatology Symposium Proceedings. 2006. Elsevier. p. 87-92.
Marchese, A., et al., Effect of fosfomycin alone and in combination with N-acetylcysteine on *E. coli* biofilms. International journal of antimicrobial agents, 2003. 22: p. S95-S 100.
Marczin, N., et al., Antioxidants in myocardial ischemia-reperfusion injury: therapeutic potential and basic mechanisms. Archives of Biochemistry and Biophysics, 2003. 420(2): p. 222-236.
Martin, P., Wound healing—aiming for perfect skin regeneration. Science, 1997. 276(5309): p. 75-81.
Martins-Green, Chapter 2: Role of oxidants and antioxidants in diabetic wound healing. Wound Healing, Tissue Repair, and Regeneration in Diabetes. (2020), pp. 13-38. Abstract Only. Website: doi.org/10.1016/B978-0-12-816413-6.00002-2.
Mayet, N., et al., A comprehensive review of advanced biopolymeric wound healing systems. Journal of pharmaceutical sciences, 2014. 103(8): p. 2211-2230.
McKee, S. Renovo stock demolished by Justiva trial failure. PharmaTimes online, Feb. 15, 2011. 6 pages. Website: pharmatimes.com/news/renovo_stock_demolished_by_justiva_trial_failure_979597/.
Merediz, S.A.K et al. 2000. Ballistic transfer of minimalistic immunologically defined expression constructs for IL4 and CTLA4 into the corneal epithelium in mice after orthotopic corneal allograft transplantation. Graef's Arch. Clin. Exp. Ophthalmol. 238, 701-707.
Miller, M.S., Use of topical recombinant human platelet-derived growth factor-BB (becaplermin) in healing of chronic mixed arteriovenous lower extremity diabetic ulcers. The Journal of foot and ankle surgery, 1999. 38(3): p. 227-231.
"Types of Burns", 2018, from website: rnspeak.com/wp-content/uploads/2018/05/burn-classification-of-injuries.jpg.
Martins-Green, Chapter 2: Role of oxidants and antioxidants in diabetic wound healing. Wound Healing, Tissue Repair, and Regeneration in Diabetes. (2020), pp. 13-38. Website: doi.org/10.1016/B978-0-12-816413-6.00002-2.
Ter Riet, G., A.G. Kessels, and P.G. Knipschild, Randomized clinical trial of ascorbic acid in the treatment of pressure ulcers. Journal of clinical epidemiology, 1995. 48(12): p. 1453-1460.
"Wound Healing: Biochemical and Clinical Aspects by Cohen, I.K., Diegelman, R.F. and Lindblad, W.J. 656 pp. Philadelphia: W.B.

(56) References Cited

OTHER PUBLICATIONS

Saunders, 1992", Reviewed by Adzick, N. Scott in Annals of Surgery, Nov. 1992; vol. 216, No. 5; p. 613.
Zhai, Liang et al. "An Integrated Indenter-ARFI Imaging System for Tissue Stiffness Quantification", Ultrason Imaging, Apr. 2008, 30(2), pp. 95-111. 24 pages.
Non-Final Office Action for U.S. Appl. No. 18/061,997, filed Dec. 5, 2022 on behalf of California Institute of Technology. Mailed on Oct. 1, 2025. 33 pages.
Restriction Requirement for U.S. Appl. No. 18/061,997, filed Dec. 5, 2022 on behalf of California Institute of Technology. Mailed on Jun. 10, 2025. 8 pages.

* cited by examiner

GELATIN DATA:

BALLISTIC DELIVERY AND RELATED PARTICLES, COMPOSITIONS, METHODS AND SYSTEMS

CROSS-REFERENCE TO RELATED APPLICATIONS

This application claims priority to U.S. Provisional Application Ser. No. 63/051,677 entitled "Ballistic Delivery of Ocular Therapy" filed on Jul. 14, 2020 the contents of which is incorporated herein by reference in its entirety.

FIELD

The present disclosure generally relates to delivery of particles and related particles, compositions, methods and systems. In particular, the present disclosure relates to ballistic delivery of microparticles to a target organ of an individual for placing a cargo such as a drug or an implant in the tissue in controllable fashion.

BACKGROUND

Delivery of compounds to a target organ is at the center of various medical and research activities, often focused to delivery of drugs or implants to a tissue of an organ for a therapeutic goal.

Successful delivery of a cargo however is highly dependent on the features of the target tissue as will be understood by a skilled person and certain organs and related tissues, such as the eye and the corneal tissues have biophysical properties related to layered heterogeneity that complicate the uptake and controlled administration of drug species through traditional administration approaches to topical administration.

As a consequence, delivery of a drug to the eye and in particular to the cornea or other tissue with a layered heterogeneity remains challenging as will be understood by a skilled person.

SUMMARY

Provided herein, are methods and systems and related particles and compositions that can be used to deliver a biologically active cargo such as a drug to a cornea of an individual, the delivery performed in a rapid, nonsurgical, and/or controllable fashion.

According to first aspect, a method is described for controlled ballistic delivery of a cargo and in particular, a biologically active cargo to the cornea of an individual, the cornea comprising the cornea epithelium, the Stroma of the cornea and an interface between the epithelium and the stroma, possibly comprising a Bowman's layer as will be understood by a skilled person.

The method comprises contacting the epithelium of the cornea with a convex microparticle comprising the cargo optionally in combination with a carrier material, the convex microparticle having an average dimension from 5 to 30 μm and an average density $\rho_p$ from 1 g/cc up to less than 20 g/cc, the contacting performed at particle velocity of at least 100 m/s and preferably from 200 to 500 m/s, to ballistically delivering the convex microparticle to a target region of the cornea located in the epithelium of the cornea, the stroma of the cornea, or the interface between the epithelium and the stroma of the cornea.

In some embodiments the microparticle has a density from 1.0 g/cc to 2.5 g/cc and the set target region is a target region within the epithelium of the cornea at a depth of half to one diameter of the particle.

In some embodiments the microparticle has an average density from 2.5 g/cc to 7.8 g/cc and the set target region is a target region located in the epithelium, in the stroma and/or the interface between the epithelium and the stroma (including the Bowman's layer if any) as will be understood by a skilled person upon reading of the present disclosure.

In some embodiments the microparticle has an average density from 7.8 g/cc to less than 20 g/cc and will be placed at the set target region in the interface between the epithelium of the cornea and/or in the stroma layer of the cornea, as will be understood by a skilled person upon reading of the present disclosure.

According to second aspect, a system is described for controlled ballistic delivery of a cargo and in particular a biologically active cargo to the cornea of an individual, the cornea comprising a cornea epithelium a Stroma of the cornea and an interface between the cornea epithelium and the stroma of the cornea.

The system comprises a convex microparticle having an average dimension from 5 to 30 um and a density from 1 g/cc up to less than 20 g/cc, the convex microparticle comprising the biologically active cargo optionally in combination with a carrier material. The system further comprises a device configured to ballistically deliver to the cornea the convex microparticle. The convex microparticle and the device can be used for controlled ballistic delivery of a biologically active cargo to the cornea of an individual according to methods herein described.

According to third aspect, a system is described for controlled ballistic delivery of a biologically active cargo to the cornea of an individual, the cornea comprising a cornea epithelium and a stroma of the cornea and an interface between the epithelium and the cornea.

The system comprises one or more cargo for preparation of a convex microparticle in the sense of the disclosure having an average dimension from 5 to 30 um and a density from 1 g/cc up to less than 20 g/cc, the convex microparticle comprising the biologically active cargo optionally in combination with a carrier material. The system a device configured to ballistically deliver to the cornea the convex microparticle. The convex microparticle and the device can be used for controlled ballistic delivery of a biologically active cargo to the cornea of an individual according to methods herein described. In some embodiments, the system can further comprise one or more carrier material Methods and systems herein described and related particles and compositions, in several embodiments can be used to deliver a biologically active cargo such as drugs and implants to controlled target regions of the corneal tissues and in particular to deliver microparticles to the epithelium, the stroma and/or the interface between epithelium and stroma of the cornea (including a Bowman's layer if any) with controlled spatial distribution.

Methods and systems herein described and related particles and compositions, in several embodiments can be used to deliver a biologically active cargo such as drugs and implants to inner layers of the corneal tissues, and in particular within the epithelium the interface between epithelium and stroma (encompassing a Bowman's layer if any), and the upper layers of the corneal stroma without the need of surgery.

Methods and systems herein described and related particles and compositions, in several embodiments where the carrier material is dissolvable, can be used to embed a biologically active cargo such as drugs and implants, in controlled target region of the cornea, wherein following dissolution of the carrier material the biologically active cargo stays in place.

Accordingly, methods and systems herein described and related particles and compositions, in several embodiments can be used to efficiently deliver a controlled amount of a biologically active cargo such as drugs to controlled target regions within the corneal tissues.

In particular in embodiments of methods and systems herein described and related particles and compositions applied to corneal tissue, the methods and systems of the present disclosure can thus overcome the biological barrier to mass-transfer that limits existing methods such as administration of solutions and other topical preparations for drug delivery to the cornea are washed away within just 15-30 s after instillation. [1]

, Accordingly methods and systems herein described and related particles and compositions, in several embodiments can also be used to obtain a sustained action of the biologically active cargo over a period of time (e.g. several days) which requires patient compliance to apply the topical formulation on a precise schedule. This effect would particularly be advantageous for patient populations, such as children and elderly patients, who may have difficulty complying with topical administration schedules.

Methods and systems herein described and related particles and compositions, in several embodiments can thus be used to increase bioavailability of a biologically active drug delivered to the corneal tissues compared to existing methods and preparations such as suspension, emulsions, ointments, gels and polymeric inserts used to deliver drugs to the eye.

Methods and systems herein described and related particles and compositions, in several embodiments can also be used to control spatial distribution of a drug by using a ballistic microparticle mass transfer modality. In particular, with precision microparticle technology, particles can be delivered in rings or in other patterns to affect tissues disproportionally in 2D space.

The methods and systems herein described and related compositions can be used in connection with various applications wherein controlled delivery of a biologically active cargo to the corneal tissue of the eye. For example, methods and systems herein described and related composition can be used in application to that are useful in ophthalmology, with particular reference to medical and research applications such as therapeutic treatments of the cornea and other soft tissues. Additional exemplary applications include medical (e.g. therapeutic, prophylactic and/or diagnostic) and research field as well as in additional fields identifiable by a skilled person upon reading of the present disclosure.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the present disclosure and, together with the detailed description and example sections, serve to explain the principles and implementations of the disclosure. Exemplary embodiments of the present disclosure will become more fully understood from the detailed description and the accompanying drawings, wherein:

FIG. 8 Panel B shows droplets from an aerosol excited at 60 kHz, outside of the monodisperse regime. Water was used as opposed to ethanol, which is used in later sections.

DETAILED DESCRIPTION

Figure 1A:
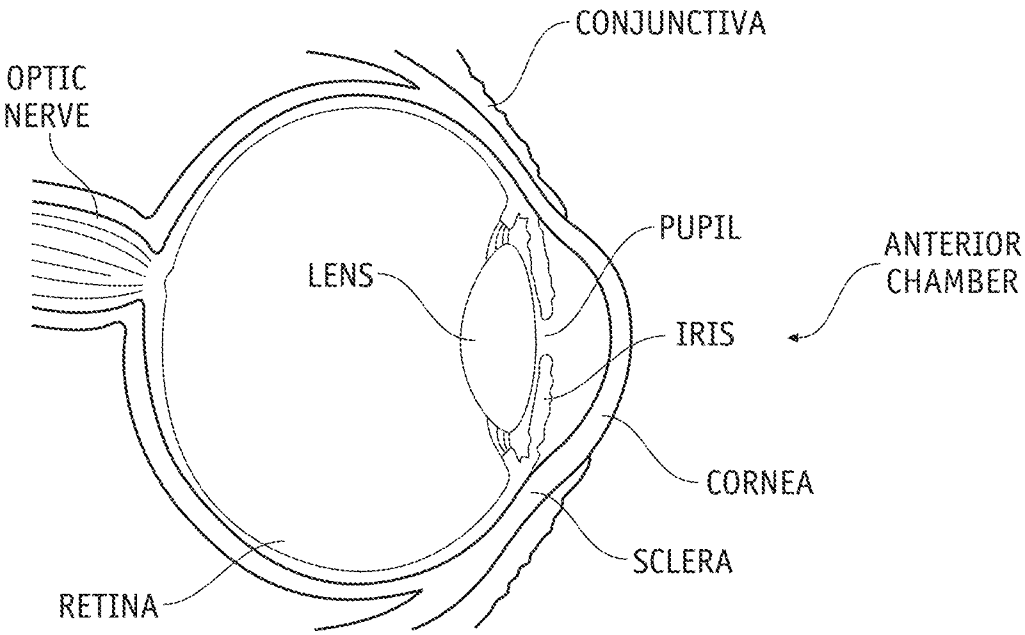
FIG. 1A shows a schematic representation of the anatomy of the eye and positioning of basic optical elements. Reproduced from the National Eye Institute. National Institutes of Health.

Provided herein, are methods and systems and related particles and compositions that can be used to deliver a cargo and in particular a biologically active cargo such as a drug to a target tissue having a layered heterogeneity, such as the cornea of an individual.

The term "biologically active" is used herein indicate capability to have an effect on or respond to living matter such as an effect on a plant, animal or another microorganism which changes the living matter physiology. In particular, biologically active molecular entities are capable to have an effect on the living matter following contact with the living matter. Compounds capable of interact with the living matter and microscopic devices that respond to living matter in which they are embedded (e.g. to release a compound and/or transmit information that is needed to appropriately care for the living matter) are examples of biological activity as will be understood by a skilled person. Biological activity is a result of the combined effect of location and concentration of a referenced item as will also be understood by a skilled person. Accordingly a biologically active molecular entity is capable to achieve a defined biological effect of on living matter [4]. And the related biological activity can be is measured in terms of potency or the concentration of the molecular entity needed to produce the effect [5].

The term "cargo" as used herein indicates a load of materials being transported by a carrier for delivery to a target organ or tissue of an individual. A cargo in the sense of the disclosure comprise any materials that can be configured for delivery in microparticles in the sense of the disclosure and comprise compounds, in which atoms are linked by covalent bonds ionic bonds and/or metallic bonds, as well as material that can be implanted to replace a missing biological structure, support a damaged biological structure, or enhance an existing biological structure. Cargos in the sense of the disclosure can be hydropilic or hydrophobic, can be electrically charged in all or portions therefore, or have no electrical charge. Cargos in the sense of the disclosure are typically solid at room temperature Exemplary cargo compounds for molecular delivery comprise drugs and genetic material inclusive in this context not only of DNA exogenous to the individual (such as transgenes) but also RNA and/or proteins and additional compounds identifiable by a skilled person. Additional exemplary cargos comprise implants which can interact with the surrounding tissue to provide a detectable effect in the tissue.

The term "drug" as used herein indicated is any substance that causes a change in an organism's physiology (intended as functions and mechanisms in the organism as a living system when contacted with the organism. Accordingly, a drug is a chemical substance, typically of known structure, which, when administered to a living organism, produces a biological effect and is used to treat, cure, prevent, or diagnose a condition or to promote well-being. Pharmaceutical drugs are often classified into drug classes—groups of related drugs that have similar chemical structures, the same mechanism of action (binding to the same biological target), a related mode of action, and that are used to treat the same disease. Exemplary drugs comprise, antibiotic, steroid, antifungal antimicrobials.

The term. "implant" as used herein indicates medical implants manufactured to replace a missing biological structure, support a damaged biological structure, or enhance an existing biological structure. An exemplary biologically active microscopic device can transduce chemical changes in the living matter, such as changes in the concentrations of dissolved gases such as oxygen or carbon dioxide, changes in concentrations of metabolites such as glucose or lactic acid. and/or a change in concentrations biological signals such as a hormone or a cytokine. Additionally, exemplary biologically active implants, comprise microscopic devices that can transduce physical and/or chemical changes in the living matter. In particular physical changes comprise changes in temperature or pH or osmolarity as will be understood by a skilled person. For example, a biologically active microscopic device can wirelessly transmit information to a monitoring system that guides appropriate action to care for the living matter. A biologically active microscopic device can autonomously respond to take a desired action based on the change in conditions of the living matter. In some cases, the spatial arrangement of a plurality of microscopic devices can provide important details regarding changes in the living matter as will be understood by a skilled person.

In methods and systems of the disclosure biologically active cargos can be combined with a carrier material to form a convex microparticle.

The term "carrier material" as used herein indicates any material that can be combined with a biologically active cargo in the sense of the disclosure to improve the selectivity, effectiveness, and/or safety of the cargo administration to an individual. Suitable carrier materials comprise polymers, glass, metal and alloys as well as additional material identifiable by a skilled person.

The terma "polymer" as used herein indicates molecule whose structure is composed of multiple repeating units. Polymers in the sense of the disclosure can be organic or inorganic, synthetic or naturally occurring as will be understood by a skilled person. Exemplary polymers comprise synthetic plastics such as polystyrene to natural biopolymers such as polysaccharide and proteins. Polymers, both natural and synthetic, are created via polymerization of many small molecules, known as monomers. Their consequently large molecular mass, relative to small molecule compounds, produces unique physical properties including toughness, high elasticity, viscoelasticity, and a tendency to form amorphous and semicrystalline structures rather than crystal as will be understood by a skilled person [6]

The term "glass" refers to a any non-crystalline (amorphous) solid that has a density of at least 1 g/cc and that exhibits a glass transition at a temperature of at least 100° C. when heated towards the liquid state. Although the atomic-scale structure of glass shares characteristics of the structure of a supercooled liquid, glass exhibits all the mechanical properties of a solid. As in other amorphous solids, the atomic structure of a glass lacks the long-range periodicity observed in crystalline solids. Due to chemical bonding constraints, glasses do possess a high degree of short-range order with respect to local atomic polyhedra. Glass can be formed by rapid cooling (quenching) of the molten form. Exemplary glass includes soda-lime glass, borosilicate glass, and barium titanate glass. Glass can be made porous to provide cavities for holding a drug as described herein. Porous glasses having an average pore size (diameter) of 40 to 200 Å can be generated by an acidic extraction of phase separated alkaliborosilica glasses, or by a sol-gel-process. By regulating the manufacturing parameters, it is possible to produce a porous glass with a pore size of between 0.4 and 1000 nm in a very narrow pore size distribution. [7]

The wording "carrier metal" as used herein refers to a any solid metal in the periodic table that is substantially stable in water under ambient or physiological conditions. The term "Periodic Table" refers to the version of IUPAC Periodic Table of the Elements dated Jun. 22, 2007, and the numbering scheme for the Periodic Table Groups is as described in Chemical and Engineering News, 63(5), 27 (1985).

As used herein, the term "alloy" refers to a metal alloy and in particular to any solid metallic particle comprising at least two metal elements in the periodic table that is substantially stable in water under ambient or physiological conditions.

In some embodiments, the biologically active cargo can be delivered in absence of any carrier materials. In those embodiments, the cargo has a density higher than the density of the target region where the cargo is to be delivered with methods and systems of the disclosure (e.g. about 1 g/cc if the target region is within any layer of the cornea) as will be understood by a skilled person upon reading of the present disclosure.

In some embodiments where the cargo has a density lower than the target layer where the cargo is to be delivered with methods and systems of the disclosure, the active cargo can be delivered in combination with any carrier materials, as will also be understood by a skilled person.

In some embodiments, the cargo can be formulated with a polymer carrier to form the microparticles. In general, carrier polymer for the microparticle as described herein are pharmaceutically acceptable and/or biodegradable.

In some embodiments, the carrier polymer for the microparticle as described can be represented by Formula (I):

$$[B_1\text{-co-}(B_2)_{b2} \ldots \text{co-}(B_m)_{bm}][X_1]_{r1} \ldots [X_p]_{rp} \quad \text{(I)}$$

in which $B_1$ to $B_m$ each refers to a block polymer moiety which are copolymerized to form copolymer $B_1$-co-$B_2$ . . . co-$B_m$, wherein m ranges from 1 to 9, b2 to bm each refers to a molar fractional number of block polymer moiety B2 to Bm relative to B1, wherein b2 to bm are each equal to or less than 1 and a sum of b2 to bm is equal to or less than 5, $X_1$ to $X_p$ each refers to a cross-linker moiety, each of which cross-links at least two polymer moieties, r1 to rp each refers a molar fractional number of cross-linker $L_1$ to $L_p$ per block copolymer $[B_1\text{-co-}(B_2)_{b2} \ldots \text{co-}(B_m)_{bm}]$, wherein a sum of r1 to rp is equal to or less than 0.5, wherein the molecular weight of the carrier particle ranges from 5000 Daltons to 5,000,000 Daltons.

In some embodiments, a polymer of Formula (I) comprises poly-N-2-dimethylamino ethyl-methacrylamide (PDMAEMAm), poly-N-2-dimethylamino ethyl-acrylamide (PDMAEAAm), poly-N-2-dimethylamino ethyl-methacrylate (PDMAEMA), poly-N-2-dimethylamino ethyl-acrylate (PDMAEA), poly methacrylamide (PMAAm), poly N,N-dimethyl methacrylamide (PDMMAAm), polymethyl methacrylate (PMMA), polyacrylamide (PAAm), polyacrylic acid (PAA), poly dimethylaminoethylmethacrylate (PDEAEMA), polyisopropylacrylamide (PNIPAAm), poly(N-isopropyl-3-butenamide) (PNIPBAm), alpha-aminoomega-methyl-poly ethylene glycol (AMPEG), poly(epsilon-caprolactone-co-lactide-polyethylene glycol) copolymer, cross-linked copolymers of polyethyleneglycol and methyacrylic acid, block copolymer poly(methacrylic acid-coethylene glycol), block copolymer poly(2-hydroxythyl methacrylate-co-N,N-dimethylaminoethyl methacrylate), poly(hydroxyethyl methacrylamide) (poly-HEMAm), copolymer poly(HEMA-co-DMAEMA) poly(hydroxylethyl methacrylate-co-N,N-dimethylaminoethylmethacrylate), copolymer of gelatin and PVA (polyvinyl alcohol), copolymer of poly-PNIPA and poly-PNIPA-Co-AA (poly N-isopropyl acrylamide and poly N-isopropyl acrylamide-co-acrylic acid), poly organophosphazene with a-amino omegamethylpolyethylene glycol, polyepsilon caprolactone-co-lactide-polyethylene glycol, poly(NIPAAm-co-AAm) (N-isopropylacryalmide-co-acryalmide), poly(methacrylamide-co-N-vinyl-2-pyrrolidone-co-itaconic acid), poly(2-(N-ethylperfluorooctanesulfonamido)ethylacrylate), a cross-linked polymer thereof or a cross-linked any combination of polymers thereof.

In some embodiments, when the carrier polymer of Formula (I) does not contain copolymer moiety and crosslinker moiety, the carrier polymer of Formula (I) as described herein can be reduced to a homopolymer and can be represented by Formula (II):

$$—[M]_n— \quad (II)$$

wherein M is a monomeric moiety, n is the degree of polymerization ranging from 50 to 500,000, M is a monomeric moiety formed by a polymerized monomer.

In some embodiments, a polymer of Formula (II) includes poly(N-vinylpyrrolidone), poly(acrylic acid), poly(methacrylic acid), poly(-hydroxyethyl methacrylate), poly(2-hydroxyethyl methacrylic acid), poly(2-hydroxypropyl methacrylate), poly(-ethyl-2-oxazoline), polymethacrylamide, polyacrylamide, poly(N-iso-propylacrylamide), poly(2-vinylpyridine), poly(2-vinylpyridine N-oxide), poly(4-vinylpyridine), poly(4-vinylpyridine N-oxide), poly(2-vinyl-1-methylpyridinium bromide), poly(ethylene oxide), poly (propylene oxide), poly(styrenesulfonic acid), poly (styrenesulfonate sodium), poly(vinylsulfonic acid), poly (vinylsulfonate sodium), poly(vinyl phosphoric acid), poly (vinyl phosphorate sodium), poly(vinyl alcohol), poly(allyl amine), poly(2-methacryloxyethyltrimethylammonium bromide), poly(N-vinylpyrrolidone), poly(vinyl acetate) or any one of combinations thereof.

In some embodiments, the monomeric moiety M contains a chemical bond that is hydrolysable under biological environment and thus the polymer is biodegradable. In such biodegradable polymer, the monomeric moiety contains an amide bond (—CO—NH—), carboxylic ester bond (—CO—O—), or an ether or a glycosidic bond (—O—).

In some embodiments, the carrier polymer is selected from the group consisting of poly(ethylene glycol) (PEG), poly(D-lactic acid) (PDLA), poly(L-lactic acid) (PLLA), poly(D-lactic acid-co-L-lactic acid) (PDLLA) and poly(ethylene glycol), polyglycolic acid (PGA) or any combination thereof.

In some embodiments, the carrier polymer comprises poly(D-lactic acid-co-L-lactic acid) (PDLLA) wherein the molar ratio of D-lactic acid to L-lactic acid moieties ranges from 10:1 to 1:10.

In some embodiments, the carrier polymer comprises poly(L-lactic acid) (PLLA) and/or poly(D-lactic acid) (PDLA/PLLA).

In some embodiments, the carrier polymer comprises poly(L-lactic acid) (PLLA) and poly(D-lactic acid) (PDLA) wherein the poly(L-lactic acid) (PLLA) and poly(D-lactic acid) (PDLA) has a weight ratio of 10:1 to 1:10.

In some embodiments, the carrier polymer comprises poly(L-lactide-co-caprolactone) of Formula (IXa), wherein m and n each ranges from 50 to 50,000, optionally the ratio of m to n ranges from 10:1 to 1:10.

Formula (IXa)

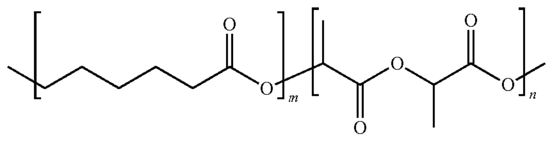

In some embodiments, the carrier polymer comprises poly(D-lactide-co-caprolactone) of Formula (IXb), wherein m and n each ranges from 50 to 50,000, optionally the ratio of m to n ranges from 10:1 to 1:10.

Formula (IXb)

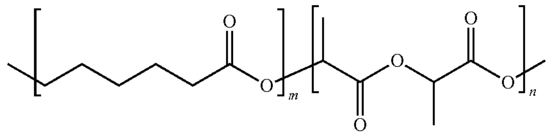

In some embodiments, the microparticle as described herein further comprise additive, wherein the additive facilitates crosslinking of collagen fibrils.

In some embodiments, the microparticle as described herein further comprise additive, wherein the additive comprises copper (II) ion.

The term "monoscaccharide" refers to a carbohydrate unit that is not decomposable into simpler carbohydrate units by hydrolysis, is classed as either an aldose or ketose, and contains one or more hydroxyl groups per molecule. Exemplary monosaccharides comprise glucose, fructose, or ribose. Additionally, exemplary amino monosaccharide includes but is not limited to N-acetylglucosamine, sialic acids such as neuraminic acid, D-galactosamine. Monosaccharides can occur naturally or be chemically synthesized. Monosaccharide monomers can be bound one to another by glycosidic bond which can be an alpha or a beta glycosidic bond. For example, cellobiose, Formula (Xa), consists of two glucose moieties linked by a beta (1-4) glycosidic bond.

Formula (Xa)

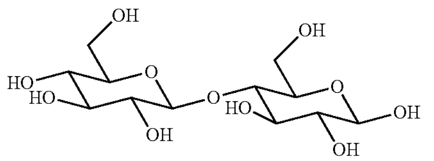

In another example, alpha-maltose, Formula (Xb) consists of two glucose moieties linked by an alpha (1→4) glycosidic bond.

Formula (Xb)

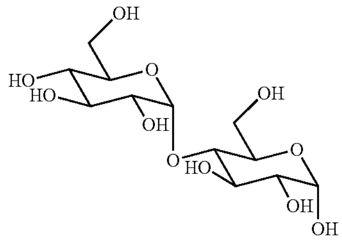

In some embodiments, a polymer includes at least two monosaccharide moieties linked by at least one glycosidic bond. Exemplary neutral monosaccharide includes but is not limited to D-glucose, D-mannose, D-galactose, D-xylose, D-apiose, L-rhamnose, D-galactose, D-fructose, L-fucose, D-ribose, and L-arabinose. Exemplary carboxylic acid monosaccharide includes but is not limited to L-iduronic acid, 2-O-sulfo-L-iduronic acid (IdoA2S), D-glucopyranuronic acid, D-galacturonic acid.

In some embodiments, biodegradable polysaccharides for the microparticle composition includes agarose, amylose, chitin, chitosan, any of the derivative thereof, or any of the combinations thereof.

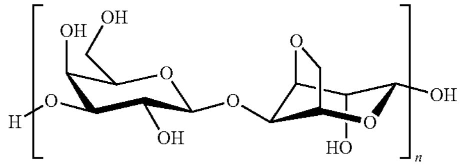

Agarose

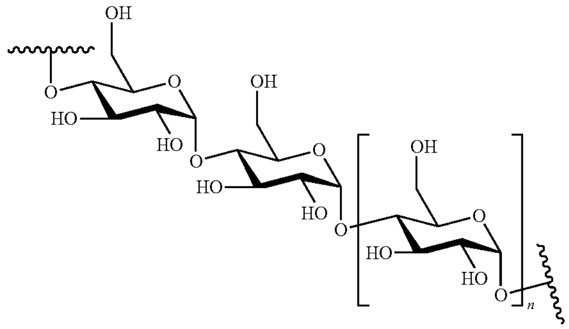

Amylose

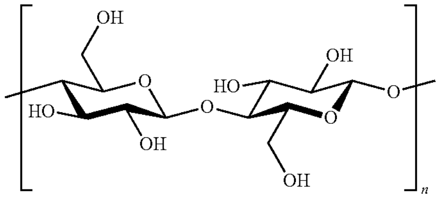

Cellulose

-continued

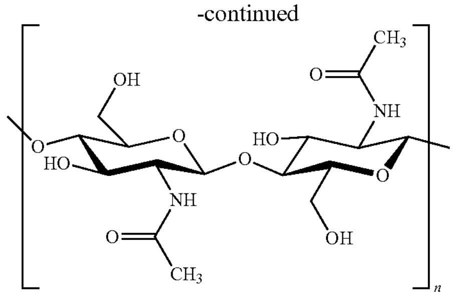

Chitin

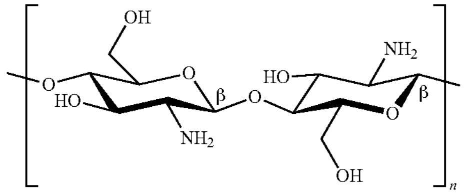

Chitosan

In embodiments where the carrier material comprises a polymer carrier material, a microparticle can be formed by mixing the cargo with the carrier in a suspension or a solution of a solvent. The mixture can be aerosolized to form small droplets, for example, through a pinhole of a vibrating orifice aerosol generator. Evaporation of solvent provides the microparticle with the cargo.

In some embodiments, the carrier material can comprise a glass carrier be prepared in microparticle form. . . . In particular suitable glass carrier comprise silicate glasses based on the chemical compound silica (silicon dioxide, or quartz), such as borosilicate glasses, and silica-free glasses as will be understood by a skilled person. Suitable glasses can be porous glass includes pores, usually in the nanometre- or micrometre-range, Exemplary glasses can comprise SiO2 and/or B2O3, Soda-Lime glass and barium titanate glass.

In embodiments wherein the carrier material comprises a glass carrier, a cargo can be dissolved in a suitable solvent. The drug cargo solution can then be mixed with a porous glass of 5 to 30 mm and fills the cavity of the porous glass with the solution. Evaporation of the solvent leaves the drug in the cavity having an average pore size (diameter) of 40 to 200 Å and provides a glass microparticle comprising a cargo. Additional methods to prepare a microparticle identifiable by a skilled person.

In some embodiment, a carrier glass can comprise any one of soda-lime glass, borosilicate glass, aluminosilicate glass. In some embodiment, the carrier glass can have a spherical shape having a diameter of 5 to 30 μm. In some embodiments, the carrier glass can be porous having an average pore size (diameter) of 40 to 200 Å, preferably 80 to 150 Å. The porosity of the glass can be used in connection with the loading of the cargo and in particular to increase loading of one or more cargos loaded on a particle.

In particular in some embodiment, a glass microsphere can be formed using $SiO_2$ and $B_2O_3$ that can contain up to 45% porosity. The porosity makes these material suitable to include cargos and accordingly these “thirsty glass” materials can be made to carry drug solutions of interest. Due to the density of SiO2 (2.65 g/$cm^3$), these carriers can be considered particles of interest for ballistic drug delivery applications [8]. Aspherical porous silica has already been demonstrated as a highly effective ballistic drug delivery carrier. [9]

In some embodiments, the carrier material can comprise a carrier metal. In particular, in some embodiments, a carrier metal can be a transition metal including Group 3 to Group 12 elements. In some embodiments, a carrier metal can be a main group metal including metal elements in Group 13 to Group 14.

In some embodiments, a metal elemental can be made porous, for example, by space-holder method. In these methods, a metal microparticle is made to contain a filler material in the powder form. Ammonium bicarbonate particles for example can be used as the space holders. The ammonium bicarbonate particles can be removed by decomposition at a temperature below 200° C. to produce a porous metal microparticle.

In some embodiments, porous metal microparticles having an average pore size (diameter) of 40 to 200 Å can be generated by space-holder method.

In embodiments wherein the microparticle comprise a carrier metal, a cargo as described in can dissolved in a suitable solvent. The cargo solution is then mixed with a porous metal microparticle of 5 to 30 μm in diameter and fills the cavity of the porous glass with the solution. Evaporation of the solvent leaves the drug in the cavity having an average pore size (diameter) of 40 to 200 Å and provides a metal microparticle comprising a drug cargo.

In some embodiment, a carrier metal can comprise to any one of metal titanium, iron, copper, silver, gold, tungsten. In some embodiment, the carrier metal can have a spherical shape having a diameter of 5 to 30 μm. In some embodiments, the carrier metal can be porous having an average pore size (diameter) of 40 to 200 Å, preferably 80 to 150 Å. Similarly, to what indicated for glass carriers the porosity of the metal can be used in connection with the loading of the cargo and in particular to increase loading of one or more cargos loaded on a particle according to the disclosure.

In some embodiment, a metal carrier can be or comprise a metal oxide which can comprise iron oxide Fe3O4. In some embodiment, the carrier metal oxide can have a spherical shape having a diameter of 5 to 30 μm. In some embodiments, the carrier metal oxide can be porous having an average pore size (diameter) of 40 to 200 Å, preferably 80 to 150 Å. The porosity of the metal oxide can be used to provide particles with a set density and loading amount of a desired cargo.

In some embodiment, a metal carrier can be or comprise tungsten and tungsten carbide microspheres can be prepared with hollow or porous morphologies, and can be used as a carrier material in connection with providing microparticles with high densities (over 7.8 g/cc). [10]

In some embodiments the carrier material can comprise a carrier alloy. In particular in some embodiments, a carrier metal alloy comprises at least a transition metal including Group 3 to Group 12 elements. In some embodiments, a carrier metal alloy comprises at least a main group metal including metal elements in Group 1, Group 2, Group 13 or Group 14. In some embodiments, a carrier metal alloy comprises at least a transition metal including Group 3 to Group 12 elements and at least one main group metal element in Group 1, Group 2, Group 13 or Group 14.

In some embodiments, metal alloy microparticles can be made porous, for example, by space-holder method. In these methods, a metal alloy microparticle is made to contain a filler material in the powder form. Ammonium bicarbonate particles for example can be used as the space holders. The ammonium bicarbonate particles can be removed by decomposition at a temperature below 200° C. to produce a porous metal alloy microparticle.

In some embodiments, porous metal alloy microparticles having an average pore size (diameter) of 40 to 200 Å can be generated by space-holder method.

In some embodiments, a cargo as described in can dissolved in a suitable solvent. The cargo solution is then mixed with a porous metal alloy microparticle of 5 to 30 μm in diameter and fills the cavity of the porous metal alloy microparticle with the solution. Evaporation of the solvent leaves the drug in the cavity having an average pore size (diameter) of 40 to 200 Å and provides a metal alloy microparticle comprising a drug cargo.

In some embodiment, a carrier alloy can comprise to any one of metal alloys comprising titanium, iron, copper, silver, gold, or tungsten. In some embodiment, the carrier alloy can have a spherical shape having a diameter of 5 to 30 μm. In some embodiments, the carrier metal alloy can be porous having an average pore size (diameter) of 40 to 200 Å, preferably 80 to 150 Å. The porosity of the metal alloy helps can be used in connection with the loading of the cargo and in particular to increase loading of one or more cargos loaded on a particle in accordance with the disclosure.

In some embodiments, porous steel or other alloys can be prepared using mechanical pulverization and sieving and additional method identifiable by a skilled reader.

In some embodiments, the biologically active cargo as described herein comprises an active pharmaceutical ingredient. An active pharmaceutical ingredient refers to any substance or mixture of substances intended to be used in the manufacture of a drug product and that, when used in the production of a drug, becomes an active ingredient in the drug product.

In some embodiments, the microparticle as described herein comprises an ophthalmic medicine selected from the group consisting of prostaglandin analog, α-adrenoreceptor agonist, β-adrenoreceptor antagonist, carbonic anhydrase inhibitor, and parasympathomimetic agents or any combination thereof.

In some embodiments, ophthalmic prostaglandin analog as described herein attenuates intraocular pressure (TOP) by improving the outflow of aqueous humor. Prostaglandin analogs exhibit agonistic activity on FP prostanoid receptors, which promotes uveoscleral outflow. Medications within this class include latanoprost, travoprost, bimatoprost, tafluprost, and unoprostone isopropyl.

In some embodiments, ophthalmic α-adrenoreceptor agonists as described herein can decrease production of aqueous humor. Ophthalmic α2 agonists include brimonidine and apraclonidine. By activating α2 receptors in the ciliary epithelium, adenylyl cyclase becomes inhibited and cyclic adenosine monophosphate (cAMP) is no longer formed. This hinders ion transport and, thus, fluid production. Over time, these medications can improve fluid outflow as well.

In some embodiments, ophthalmic β-adrenoreceptor antagonist as described herein can reduce intraocular pressure (TOP) by decreasing aqueous humor production. Beta-blockers antagonize the effects of sympathetic neurotransmitters by inhibiting β1 and β2 receptors. Exemplary ophthalmic β-adrenoreceptor antagonist include timolol, betaxolol, carteolol, and levobunolol.

In some embodiments, ophthalmic carbonic anhydrase inhibitors (CAIs) as described herein works by decreasing production of aqueous humor. Carbonic anhydrase is an enzyme that catalyzes the formation of bicarbonate from carbon dioxide and water (and vice-versa), with the most active isoform being carbonic anhydrase II. Inhibition of this isoenzyme within the ciliary epithelium slows the formation of bicarbonate ions; decreasing the extracellular transport of water necessary for aqueous humor production. Exemplary ophthalmic carbonic anhydrase inhibitors (CAIs) includes dorzolamide, brinzolamide and acetazolamide.

In some embodiments, ophthalmic parasympathomimetic agents as described herein are cholinergic agonists that reduce IOP by improving fluid outflow through the trabecular meshwork. Activation of muscarinic (M3) receptors allows for contraction of ciliary muscle fibers, which expands the pores of the trabecular meshwork to enhance outflow. Ophthalmic agents within this class include carbachol and pilocarpine.

In some embodiment, the ophthalmic medicine includes anti-inflammatory agent selected from the group consisting of dexamethasone, cyclosporine, bromfenac, nepafenac, ketorolac, suprofen, flurbiprofen or any combinations thereof.

In some embodiment, the ophthalmic medicine includes an anti-angiogenic ophthalmic agent selected from the group consisting of aflibercept, ranibizumab, pegaptanib, and brolucizumab, or any combinations thereof.

In some embodiment, the ophthalmic medicine includes a mydriatics selected from the group consisting of homatropine, cyclopentolate, tropicamide, phenylephrine, scopolamine, atropine or any combinations thereof.

In some embodiment, the ophthalmic medicine includes an anesthetic selected from the group consisting of tetracaine, proparacaine, lidocaine, or any combinations thereof.

In some embodiment, the ophthalmic medicine includes an anti-infective selected from the group consisting of moxifloxacin, gatifloxacin, ganciclovir, azithromycin, polymyxin b/trimethoprim, besifloxacin, tobramycin, trifluridine, vidarabine, oxytetracycline/polymyxin b, sulfacetamide sodium, erythromycin, levofloxacin, ofloxacin, gentamicin, chloramphenicol, gramicidin/neomycin/polymyxin b, bacitracin/neomycin/polymyxin b, idoxuridine, ciprofloxacin, chloramphenicol, or any combinations thereof.

In some embodiment, the ophthalmic medicine includes an antihistamines and/or decongestant selected from the group consisting of tetrahydrozoline/zinc sulfate, olopatadine, naphazoline/pheniramine, bepotastine, alcaftadine, ketotifen, epinastine, phenylephrine, azelastine, pemirolast, naphazoline/zinc sulfate, nedocromil, cetirizine, oxymetazoline, levocabastine, emedastine, cromolyn, lodoxamide, or any combinations thereof.

In some embodiment, the ophthalmic medicine includes a glaucoma agent selected from the group consisting of brimonidine/brinzolamide, netarsudil, bimatoprost, brimonidine/timolol, latanoprost/netarsudil, latanoprost, tafluprost, latanoprostene bunod, travoprost, dorzolamide/timolol, brimonidine, dorzolamide, brinzolamide, echothiophate iodide, timolol, unoprostone, dipivefrin, pilocarpine, metipranolol, carteolol, acetylcholine, carbacholor, apraclonidine, physostigmine, epinephrine, bimatoprost, betaxolol, and levobunolol, or any combinations thereof.

In some embodiment, the ophthalmic medicine includes a steroid selected from the group consisting of difluprednate, loteprednol, dexamethasone, fluocinolone, triamcinolone, rimexolone, fluorometholone, and prednisolone or any combinations thereof.

In some embodiment, the ophthalmic medicine can comprise a photosensitizing agent that can induce corneal cross-linking. In response to light exposure with specific wavelengths, photosensitizing agents generate reactive oxygen singles that participate in photochemical reactions to form advanced glycan endproducts, covalent cross-links between amino acids in collagen chains. In addition, species that are not photosensitizing, including metal ions, can be delivered which act as enzymatic cofactors in cross-linking reactions In some embodiment, the ophthalmic medicine can comprise a compound which participates in the cross-linking of collagen in the cornea. Riboflavin and Eosin Y have been demonstrated as compounds that when irradiated with the correct wavelength of light, will generate oxygen singlets that participate in the formation of advanced glycan end-product crosslinks. Copper ions have also been shown to be able to crosslink collagen in the presence of lysyl oxidase enzymes.

In embodiments, herein described biologically active cargo in the sense of the disclosure form a microparticle The term "microparticle" in the sense of the disclosure, indicates particles with a dimension from 1 and 1000 μm and in particular with dimension of less than 300 um and a density from 0.1 g/cc to less than 20/gcc. Size of microparticles can be effectively measured using scanning electron microscopy. Standard light transmission microscopy can be used as well in combination with reference standard objects to measure size. Size, mass, and density measurement can be achieved using a quadrupole ion trap [11]. Another way to measure particle density includes measuring the settling velocity of particles in water by using a microscope focused on a vertical capillary. Several microparticles are commercially available in a wide variety of materials, including ceramics, glass, polymers, and metals.

Microparticle in the sense of the disclosure are convex microparticles having an average density $\rho_p$ from 1 g/cc to less than 20 g/cc and an average diameter $D_p$ from 5 μm to 30 m.

The term "convex" when used in connection with microparticles indicates a particle which has a having a surface of the particle curved such as the exterior of sphere or ellipsoid. Convex microparticles comprise spherical discs, rods, and other shapes as will be understood by a skilled person [11].

. The term "average density" of a particle as used herein indicates the total mass of particles divided by the total volume of those particles. The "density" of a particle is equal to the particle Average density of the particles can be measured in several ways known to the person skilled in the art, such as: measurement of total mass of the particles divided by total volume of the particles, obtained through techniques including but not limited to spectroscopy, buoyancy, frequency shifting and so on. See, for example, "Volume and density determinations for particle technologists", Paul A. Webb (February 2001) [12], incorporated herein by reference in its entirety. mass divided by the particle volume particle.

For example, to measure the density of the microparticles, the microparticles are placed inside a pycnometer of known volume and weighed. The Pycnometer is then filled with a fluid of known density, in which the microparticle is not soluble. The volume of the microparticles is determined by the difference between the volume as shown by the pycnometer, and the volume of liquid added (i.e. the volume of air displaced). Division of weight of the microparticle by the measured volume gives the density of the microparticles. When all the particles are the same, the result gives the density of individual microparticle. When particles have different density, the result is the average density of all particles that are involved in the measurement.

In particular, the average density can be measured using a statistically significant sample of n particles and measuring the total mass $n<m_p>$ and displaced volume $n<V_p>$, then computing the ratio of mass to volume, $\rho_p=(n<m_p>)/$ $(n\langle V_p\rangle)=\langle m_p\rangle/\langle V_p\rangle$. In the present disclosure, particles have an average density $\rho_p$ that is at least 1 g/cc and equal to or less than 20 g/cc.

The term "average dimension" as used herein indicates is the summation of dimension of all particles divided by the number of particles. The dimension of a single particle indicates the diameter of a particle if the particle is spherical or the diameter of a representative sphere is the particle is non spherical wherein the diameter of the representative sphere is calculated based on the volume or the area of the non-spherical particle.

In particular a volume-based particle size equals the diameter of the sphere that has the same volume as a given particle. Typically used in sieve analysis, as shape hypothesis (sieve's mesh size as the sphere diameter).

$$D = 2\sqrt[3]{\frac{3V}{4\pi}} \quad (2)$$

where D: is the diameter of representative sphere and V is volume of particle

An area-based particle size equals the diameter of the sphere that has the same surface area as a given particle. Typically used in optical granulometry techniques.

$$D = \sqrt[2]{\frac{4A}{\pi}} \quad (3)$$

where D is the diameter of representative sphere and A: surface area of particle In some embodiments, where the convex microparticle of the disclosure to be delivered have different dimensions, the distribution of particle sizes can be narrow, by which it is meant that 90% of the biological cargo is contained in particles that have individual diameter $D_{pi}$ from $0.9\langle D_p\rangle$ to $1.1\langle D_p\rangle$. In some embodiments, where the convex microparticle of the disclosure have different dimensions the distribution of particles can be moderately broad, by which we mean 80% of the biologically active cargo is contained in particles having individual diameter $D_{pi}$ from $0.75\langle D_{pi}\rangle$ to $2\langle D_{pi}\rangle$.

In exemplary embodiments, two different batches of convex microparticles both have diameter $\langle D_p\rangle=15$ microns and have very different size distributions. When a statistically significant number of particles is examined under the microscope, one sample shows no particles having effective dimension less than 13.5 microns and no particles having effective diameter greater than 16.5 microns. For particles that carry biological cargo in proportion to their volume, such an observation indicates that more than 90% of the biological cargo is contained in particles that have individual effective diameters $D_{pi}$ from $0.9\langle D_{pi}\rangle$ to $1.1\langle D_{pi}\rangle$. For the other sample of substantially spherical particles with $\langle D_p\rangle=15$ microns, examination of a statistically significant number n of particles shows that 10 of 100 particles have $D_p<5$ microns, and 5 of 100 particles have $D_p>30$ microns (representing >125-times the mass of the particles with $D_p<5$ microns); and 10 of 100 have Dp from 5 to 7.5 microns. The n individual effective diameter values are used to estimate the volume of each particle; the sum of the n particle volumes gives the total volume of the n particles; starting from the smallest particle detected, individual particle volumes are summed until the cumulative volume equals 10% of the total volume, the $D_p$ of the last small particle in the sequence is taken as the cutoff diameter at small particles size, $D_{small}$; repeat the process starting from the largest particle detected and sum the volume until the cumulative volume equals 10% of the total; the Dp of the last large particle in the sequence is taken as the cutoff size for large particles that account for 10% of the total volume, $D_{large}$. A particular batch of substantially spherical particles having $\langle D_r\rangle=15$ microns and prepared such that the biologically active cargo is loaded in proportion to particle volume, is found to have $D_{small}=11$ microns and $D_{large}=35$ microns. The range of effective particle diameters starts below $0.75\langle Dp\rangle$ and extends beyond $2\langle D_p\rangle$; such a distribution would be regarded as broad.

In some embodiments, a convex particle can be substantially spherical, where the term substantially spherical refers to irregular convex particles having a sphericity index value from 0.9 to 1.0. The sphericity is taken to be the minimum of two different expressions, each of which individually proved adequate for efficiently identifying a useful point in the operating space of particle size, particle density and particle velocity for a specified the tissue of interest, target layer, tissue properties and particle accelerating device. The first of the methods of evaluating the sphericity is: the cube root of the ratio of the average particle volume $\langle V_p\rangle$ to the average volume of the smallest sphere that circumscribes a particle. In which the volume displaced by a statistically significant sample of n particles is used as $n\langle V_p\rangle$ to evaluate $\langle V_p\rangle$ and the average volume of the smallest circumscribing sphere $\langle V_{cs}\rangle$ is computed by analyzing a micrograph of the set of n particles spread apart such that the silhouette of each particle is visible, the particles tend to have their long axis approximately parallel to the microscope slide and the n values of the length of the long axis $a_{la}$ of the n particle silhouettes in the micrograph are used to compute the n volumes of the individual circumscribing spheres $V_{cs}=(\pi/6)a_{la}^3$. The second method uses the micrograph to determine the n pairs of values of $a_{la}$ and minor axis length $b_{la}$ in the direction orthogonal to the long axis of a given particle's silhouette and the sphericity is evaluated as the cube root of $(a_{la}^3)/(a_{la}b_{la}^2)=(a_{la}/b_{la})^2$.

In some embodiments a substantially spherical particle tends to lie down with their thinnest axis orthogonal to the microscope slide and is identified as platelet-like particles, because they are seen through the microscope to be platelets. In those embodiments, the first of the methods of evaluating the sphericity should be used.

In embodiments wherein substantially spherical particles are used, the average particle diameter can be evaluated using a micrograph of a statistically significant number of particles n as the average of the n values of the effective particle diameter, calculated as square root of the area of a particle silhouette in the micrograph. Particles carrying biologically active cargo can have internal variations of density and their effective density is equal to the particle mass divided by the particle volume particle.

In some embodiments, a convex microparticle in the sense of the disclosure can be an irregularly shaped convex particle having a major axis, a minor axis and an intermediate axis as will be understood by a skilled person. The major axis refers to the longest line that connects two points on the surface of the particle. The coordinates of one of the endpoints is taken as the origin and the opposite end point is (x,y,z) the length of the major axis denoted by $a_{major}$, is the square root of the sum of squares x,y,z, sqrt($x^{2+}$ $y^{2+}$ $z^2$). The intermediate axis is the longest line that is orthogonal to the major axis and connects two points on the surface of the particle. The length of the line connecting the two end points of the intermediate axis is denoted $a_{intermed}$. When the major and intermediate axes are known, the minor axis is the longest line between two points on the surface of the particle and is orthogonal to both the major and intermediate axes. The minor axis length is denoted $a_{minor}$. The methods used to characterize particle shape determine average values over a large number of particles. The most common techniques to determine particle size distribution are dynamic image analysis (DIA), static laser light scattering (SLS, also called laser diffraction), dynamic light scattering (DLS) and sieve analysis. The most sophisticated techniques for evaluating the size and shape is tomography as will be understood by a skilled person. Depending on the size range and optical properties of the particles, confocal optical microscopy (particle axis lengths of at least 5 microns; particle surface fluorescently labeled) and/or optical coherence tomography (particle axis lengths of at least 20 microns and particle surface that strongly scatters light). For detailed characterization of particles that have a dimension that is less than 5 microns can be performed using scanning electron microscope micro-computed tomography or x-ray micro-computed tomography. Tomographic images are used to evaluate all three of the principle axes of each particle and the compute desired average quantities from them.

An irregularly shaped convex particle can be produced as the result of a process used to load a particular biologically active agent into particles. For example, when a macroscopic block of materials is pulverized to create a powder of irregularly shaped convex particles from which, according to the disclosure, the desired range of particle size is obtained. Alternatively, regularly-shaped non-spherical particles can be produced by a variety of established methods, including but not limited to 3D printing, micro-molding, and extrusion with pelletization.

In in some embodiments of the disclosure, preferred irregularly shaped particles have $a_{intermed}/a_{major}$, between ½ and 1/10 and have $a_{minor}/a_{intermed}$ between ½ and 1.

In some embodiment microparticles of the present disclosure can comprise more than one cargo and more than one carrier materials that can be combined to allow coupling of the carrier with the cargo and/or to obtain a desired density as will be understood by a skilled person.

Microparticles comprising a cargo and optionally a carrier material in the sense of the disclosure can be prepared with methods identifiable by a skilled person upon reading of the present disclosure which depend on the specific cargo and specific carrier material as will be understood by a skilled person. Additional, preparation of a microparticle with set density and amounts of cargo can also be identified by a skilled person.

Methods to prepare microparticles in the sense of the disclosure include mechanical pulverization, spray-drying, spray chilling, and emulsion-drying techniques as well as additional methods identifiable by a skilled person [13]. [14] [15].

In some embodiments, the convex microparticle of the disclosure can be monodisperse in some embodiments the convex microparticle of the disclosure can be polydisperse The dispersity is a measure of the heterogeneity of particles in a mixture. A measure of the dispersity is provided by the Polydispersity index (PDI) which is a measure of the breadth of the particle size distribution for the microparticles as described herein. PDI is defined as the square of the standard deviation divided by the mean particle diameter. For a perfectly uniform ("monodisperse") sample consisting of exactly one and only one particle dimension. Microscopy measurement of particle sizes will provide data for PDI calculation. A narrow, moderate and broad polydisperse microparticle has PDI in the ranges of 1.0-1.1, 1.1-2.0, and greater than 2.0, respectively as will be understood by a skilled person.

In some embodiments, preparation of microparticles can be performed using a vibrating orifice aerosol generator (VOAG) to prepare a microparticle with a set density and diameter.

In particular a VOAG can be used incorporate density boosting metal nanoparticles. For example, gold or tungsten nanoparticles with size less than 100 nm have settling velocities low enough such that they will stay dispersed in a liquid. Accordingly, inclusion of these metal nanoparticles together with a suitable cargo in the liquid used to prepare microspheres using the VOAG will include the metal within carrier materials used to form to microspheres. In particular, in some embodiments, I=incorporating one or more carriers formed by high density materials can impart mass needed to increase momentum that contributes to particle embedding energy as will also be understood by a skilled person, for example tungsten nanoparticles can be added to an ethanol/polymer solution further including a cargo to prepare a microparticle with a density higher than 7.8 gg/cc as will be understood by a skilled person.

In additional exemplary embodiments a VOAG can be used with a carrier polymer such as poly(ethylene glycol) dissolved in suitable solvent (such as ethanol) and a drying column, to provide microparticles in the sense of the present disclosure using a spray drying technique. In those embodiments, the solution is ejected from the VOAG and is converted into a droplet train that has low polydispersity. The droplets can then then be fed into a drying column (e.g. 1-meter-tall) with nitrogen fed at 30 standard cubic feet per minute. As particles settle to the bottom of the column, which is heated to a suitable temperature (e.g. 120° C.), ethanol is evaporated from the droplets until a solid particle is left over at the bottom. From empirical research, it was found that droplets had to be prepared that were 70-90 μm in diameter in order to become fully solid at the bottom of the column.

In embodiments, wherein spray drying technique are performed with a VOAG it is possible to obtain a precise control of the size of droplets produced and include additives with polymers or other carrier materials to change the composition and physical properties of the microparticle. Droplet size can be changed using different precision pinholes in the VOAG as will be understood by a skilled person (see Examples section). Additional size control can be achieved by modulating the vibration of piezoelectric excitation. The resulting dry particle that can be produced is proportional to the size of the droplet emitted by the VOAG (see Examples section).

In addition to providing control over the size of the dry particles produced by spray drying technique, the VOAG allows customization of particle composition and properties. For example, incorporating charged species (e.g. lysine) will result in a hollow particle morphology. Methods have already been discussed to alter particle density using metal nanoparticles.

In embodiments, where the a VOAG is used a precise control over the polydispersity of the droplets emitted from the device can also be achieved as will be understood by a skilled person. By exciting the VOAG piezoelectric ceramic with appropriate frequencies, monodisperse droplet trains can be emitted from the device. As long as particles are effectively dispersed in a drying column, preventing coagulation, the resulting fully-dried particles will be monodisperse as well. If a polydisperse size distribution is desired, excitational frequencies can simply be turned off. Monodisperse particles, assuming they have the same impact velocities, will be found at similar penetration depths within a soft, homogeneous target substrate. Polydisperse particles will result in a more varied penetration depth distribution as will be understood by a skilled person.

In some embodiments, microparticles with set caracteristicus can be commercially sourced, as will be understood by a skilled person. Manufacturers comprises Spherotech and Cospheric and additional manufacturer identifiable by a skilled person In embodiments herein described microparticles according to the disclosure can be delivered with a method and system are described for controlled ballistic delivery of a biologically active cargo to the cornea of an individual.

The term cornea as used herein indicates the transparent front part of the eye (a sense organ that reacts to light and allows vision) of an individual.

When referred to as a noun, the term "individual" as used herein in the context of treatment refers to a single biological organism, including animals having a sense organ that reacts to light and allows vision and in particular higher animals and in particular vertebrates such as mammals and in particular human beings.

The cornea of the eye of a human being indicates the parts that covers the iris, pupil, and anterior chamber. The cornea, with the anterior chamber and lens, refracts light, with the cornea accounting for approximately two-thirds of the eye's total optical power. The related position with respect is schematically illustrated in FIG. 1A.

Corneal tissue has biophysical properties related to layered heterogeneity that prevent the uptake of drug species.

Figure 1B:
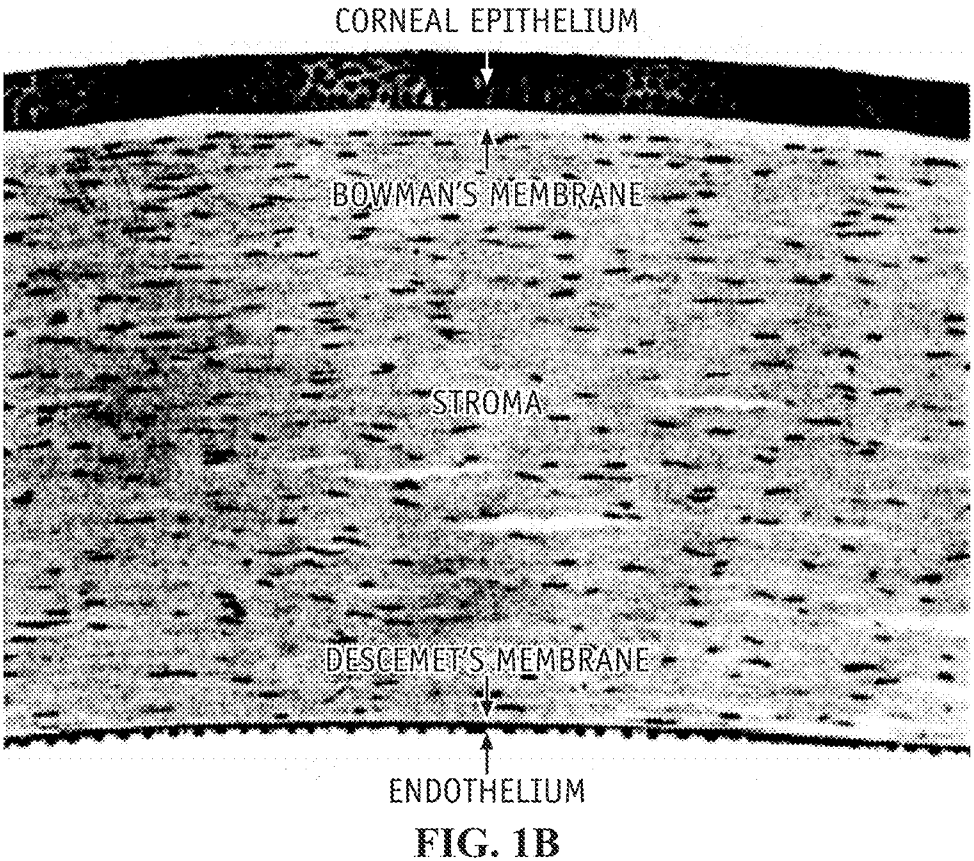
FIG. 1B shows a representation of the major layers of the cornea shown in H&E stained tissue section. Image reprinted from Ehlers and Hjortdal. [2]

The cornea is comprised of five main layers in the order of the epithelium, Bowman's Layer, the stroma, Descemet's Membrane, and the endothelium (identified in FIG. 1B).

In some individuals, such as in dog, wolf, cat, tiger, lions, rabbit, pigs, cows, goats, or horses, the Bowman's layer is not found as will be understood by a skilled person.

The epithelium is on average 53 μm thick and sits on a 0.3-μm-thick basement membrane, which consists of collagen fibrils and laminin proteins. Beneath this, Bowman's Layer, if any is present, three is a sheet of randomly oriented collagen fibrils that provides an outward toughness to the cornea. Next, the stroma constitutes most of the corneas' thickness. It is mainly acellular (1 keratocyte per 50,000 $\mu m^3$) and contains 200 collagen lamellae containing fibrils that radiate outwards at precise angles to give the cornea its transparency. The extracellular matrix consists of a mixture of peptidoglycans, glycosaminoglycans, fibronectins, and lamins [19]. The high content of peptidoglycans and glycosaminoglycans in the stroma gives the tissue a net negative charge. Finally, Descemet's Membrane is an acellular fibrous layer secreted by the endothelium monolayer below. The biomechanical strength of the cornea can be attributed to its inner stromal layer, since epithelial and endothelial cell layers lack any contiguous protein network. The interlamellar spacing between collagen fibrils and constitutive properties between protein and peptidoglycan is what gives rise to a transparent tissue, similar in structure to tendon, that has considerable mechanical strength (Table 1). [20]

As shown in Table 1 below, the cornea has significant stiffness, especially in Bowman's Layer and the stroma.

TABLE 1

Mechanical properties of individual layers of the cornea. Data from Last et al. unless otherwise specified*.

| Structure | Mechanical Properties Reported in Literature |
|---|---|
| Tear Film | Loss modulus (viscosity): 2.33 mPa [Human Rheometry]** |
| Epithelium | Elastic Modulus: 0.57 kPa [Rabbit; AFM] |
| Epithelial Basement Membrane | Elastic Modulus: 7.5 k2a [Human; AFM] |
| Bowinan's Layer | Elastic Modulus: 108.9 kPa [Human; AFM] |
| Stroma | Elastic Modulus: 33.1 kPa [Human; AFM] |
| Descemet's Membrane | Elastic Modulus: 50 kPa [Human; AFM] |
| Endothelium | Elastic Modulus: 4.1 kPa [Rabbit; AFM]*** |

*From Last et al.; 2012 [21]
**From Gouveia et al.; 2005 [22]
***From Thomasy et al.; 2014 [23]

Additionally, tear film with dissolved mucin forms a hydrophilic, negatively charged barrier, blocking hydrophobic materials or anions. Superficial epithelial cells are joined to one another by desmosomes and tight-junction complexes (*zonula occludens*). These structural elements stitch the anterior surface of the eye together and prevent the infiltration of bacteria and viruses, but also medicinal compounds. Corneal epithelial cells express an array of ATP-binding cassette efflux transporter pumps, which actively remove lipophilic molecules and organic anions from epithelial cytoplasm [24]. The corneal epithelium is lipophilic in nature—hydrophilic compounds that are delivered topically have low uptake rates. These characteristics impair the ability to deliver drugs to the cornea, and especially to underlying stromal tissue. Furthermore, precorneal barriers to drug delivery include solution drainage, blinking, and induced lacrimation.

In embodiments, herein described convex microparticle comprising a cargo in the sense of the disclosure can be ballistically delivered to the cornea a velocity equal to or higher than 100 m/s to set target regions of the cornea within the epithelium the bowman's layer, if any, the stroma and/or any interface therebetween.

The term "ballistic delivery" as used herein refers to the delivery of high velocity microparticles to a target substrate such that they are physically embedded in the target material. Particles typically have velocities of at least 100 m/s to achieve embedding in the tissue.

Techniques for accelerating microparticles include using an expanding gas to impart momentum on a microparticle. For biological substrates, a precision pneumatic device that diverts expanding gas away from a treated tissue sample can be preferred.

To detect the presence of particles in tissue and to quantify penetration depth, fluorescently active compounds can be included in the composition of ballistic microparticles. Tissues can be fixed and sectioned to identify the particles. For example, a using exposure to solutions such as aqueous 10% w/w formaldehyde solutions for up to two days. Following cryoprotection (e.g. in 10 w % sucrose solution for eight hours and 30 w % sucrose for 12 hour), tissues can be sectioned using a microtome. Then particles can be identified and their penetration depth measured using fluorescent transmission microscopy or confocal microscopy.

In embodiments, herein described the impact velocity of ballistically delivered particles of at least 100 m/s In exemplary embodiments, the ballistic delivery in the sense of the disclosure can be performed using a pneumatic capillary gun. For example, particles can be placed on a mesh substrate inserted in a luerlock tubing connector. Particles are deposited in aqueous solution with a concentration of about 1% w/w. Once the particles are fully dry (lyophillization has been used to fully dry the material), then the luer lock connector is loaded into the ballistic device. When the device is adequately aimed at a biological substrate, then a solenoid valve will be triggered to deliver compressed helium at 50-100 psig. Gas rushes past the mesh substrate, picks up the microparticles, and accelerates them down a capillary. This capillary ejects particles into a proprietary vacuum chamber, that strips away compressed gas shocks, and ejects gas free streams of high velocity microparticles. To detect microparticles in the target substrate, it helps to include a fluorescent compound in the microparticle formulation. This allows the use of confocal microscopy to identify the positioning of particles in the 3D tissue substrate.

Other forms of particle acceleration can also be employed. In additional exemplary embodiments, a PDS1000 gene gun can be used which operates by accelerating particles on a polymeric disc. For example, particles are placed on the disc and typically dried, but liquid payloads can be delivered as well. The disc is accelerated when helium bursts a rupture disc. While the device bursts a rupture disc and discharges it into a vacuum to maximize the velocity of gas expanding through a nozzle, a similar device can be designed that discharges helium into ambient air while diverting most of the harmful gas. After the polymeric disc is accelerated, it is made to collide with a mesh stopping screen. Any particles that are on the polymeric disc leave the substrate and carrying through the mesh stopping screen with the velocity of the polymeric disc at the time of collision. This method benefits by using the low aerodynamic relaxation time of the polymeric disc, meaning that high density microparticles can be accelerated to high velocities without using an impractical, long acceleration tube. Another technique to accelerate microparticles involves using laser induced projectile impact testing. In this method, particles are placed on an elastomer spun-coated on a thin gold layer (several micron thick). When the gold foil is ablated using a high powered YAG laser, a small bubble will form in the elastomer that ultimately bursts. This fast event will cause particles to eject from the surface of the elastomer at velocities as high as kilometers per second.

In embodiments herein described, the microparticle that can be delivered with method and systems of the present disclosure have a diameter from 5 to 30 um and a density from 1 g/cc up to 20 g/cc.

Methods and systems herein described and related particles and compositions, in several embodiments can be used to deliver a biologically active cargo such as drugs and implants to controlled target regions of the corneal tissues and in particular to deliver microparticles to the epithelium and bowman's layer of the cornea with controlled spatial distribution In some embodiments the microparticle has a density from 1.0 g/cc to 2.5 g/cc and the set target region is a target region the within the epithelium of the cornea at a depth of half to one diameter of the particle. For example, in some embodiments, particle velocity from 200 tom 500 m/s having a diameter 5 to 30 um with density of 1.0 g/cc, 100% of particles will be +/−30 micron from the surface of the epithelium.

In some embodiment, a particle for penetration of the top layer of corneal tissue would need no density modification and therefore can be provided by the cargo with or without carrier material to be selected accordingly as will be understood by a skilled person.

In some of those embodiments the particle comprises an ophthalmic drug to be delivered to the corneal epithelium. In some of those embodiments, the ballistic delivery can be performed by embedding particles optionally comprising polymer carrier material, the embedding performed by one diameter. In those embodiments, embedded microparticles are expected to dissolve slowly, remaining in place, without material being significantly washed away or mechanically swept out of the eye.

In an exemplary embodiment, microparticles to be delivered to target region within the epithelium of the cornea at a depth of one or two diameters of the particle can comprise: i) 90-99% w/w polyethylene glycol or PDLLA with controlled D content to tune the rate of particle hydrolysis and other biocompatible and biodegradable polymers (e.g. poly-lactic-co-glycolic acid, poly(ε-caprolactone) (PCL), poly-Lactic Acid, poly(3-hydroxybutyrate-co-3-hydroxyvalerate) (PHBV), Chitosan and Cellulose; ii) 1-10% w/w a drug (e.g. an antibiotic such as azythromyocin or doxycyclin); iii) Polydispersity between 1 and 1.1 to ensure similar penetration; iv) velocities greater than 100 m/s; and/or v) ejected using a pneumatic capillary gun. In some of those embodiments the use would be for general or localized infection of the eye.

In some embodiments the microparticle has a density from 2.5 g/cc to 7.8 g/cc and the set target region is the interface between the epithelium and the stroma in a region encompassing the Bowman's layer if any, as well as possibly portions of the epithelium and the stroma, as will be understood by a skilled person upon reading of the present disclosure.

Figure 2:
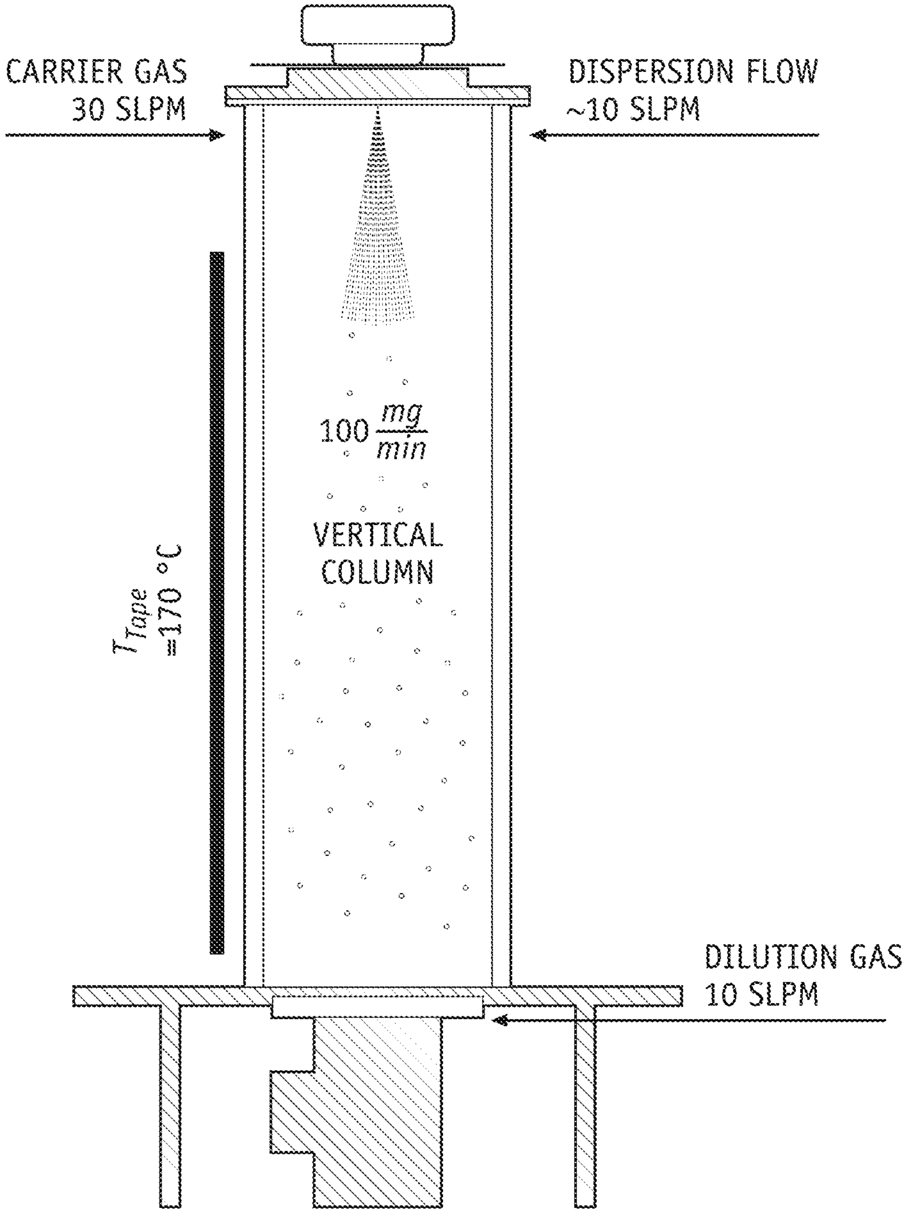
FIG. 2 shows a schematic representation of a dry column for preparation of microparticles according to the present disclosure. The schematics shows how Nitrogen is fed to the VOAG (dispersion gas), to the top of the column (carrier gas), and to the particle trap (dilution gas). The column walls are heated to a certain temperature and the VOAG usually ejects a ~200 mgs of solution a minute, if the 35 μm pinhole is used

In particular in some embodiments using density from 2.5 g/cc to 7.8 g/cc results in having microparticles delivered to the bottom of the epithelium, at the interface with the stroma, encompassing the Bowman's layer if any with insensitivity to particle impact velocity. at a depth of 5 to 10 dimeter of the microparticle depending on the dimension of the microparticles (see indications on probability density of FIG. 2.0 Example 18).

In some embodiments, particle velocity from 200 to 500 m/s the microparticle particles has a diameter of 5 to 30 um with composition 2.5 g/cc ~25% lie within +/−15 um from the stroma.

In some embodiments, particle velocity from 200 tom 500 m/s having a diameter of 5 to 30 um with composition 4.2 g/cc ~50% lie within +/−15 um from the stroma.

In some embodiments, particle velocity from 200 tom 500 m/s having a diameter of 5 to 30 um with composition 7.8 g/cc ~70% lie within +/−15 um from the stroma.

In some of those embodiments, microparticles having a density higher than 7.8 gg/cc to less than 20 g/cc can be delivered to the interface between epithelium and stroma layer, in a region that encompass the Bowman's layer if any as well as regions within the stroma as will be understood by a skilled person. In particular, microparticles within that density ranges can penetrate into the stroma by several tens of micron as will be understood by a skilled person upon reading of the present disclosure.

A skilled person will be able to select additional combination of density, dimension and velocity based on the indications provide in the examples section with particular reference to the guidance related to the probability density (see in particular in Example 18 and FIG. 20) as well as in view of the present disclosure in its entirety.

For medical applications, the system of delivery preferably includes a technique to protect tissues from materials used to impart momentum to microparticles.

In some embodiments, a particle for penetration to the interface between the epithelium and the stroma would require density modification of the cargo and therefore use of an appropriate carrier material, as will be understood by a skilled person upon reading of the present disclosure. In akme of those embodiments the cargo is a hydrophilic drug to be delivered to the corneal stroma. The corneal epithelium is hydrophobic in nature, so it slows the uptake of hydrophilic drugs. If particles can be delivered to the interface between the epithelium and the stroma, transfer of compounds to the stroma should be enhanced.

In those embodiments, the ballistic delivery can be performed taking into account that the higher the density of the particle, the larger the aerodynamic relaxation time. This results in smaller particles that are able to keep their velocity for a longer distance when ejected into still air, but particles that take longer to come to the high velocities of the expanding carrier gas. Especially for 30 μm particles with density of 7.8 g/cc, the length needed to for particles to reach speeds upwards of 100 m/s becomes long (7.2 m). The reason the same size range is chosen is to enable acceleration, but also so particles are not two orders of magnitude greater than the size of an epithelial cell. This situation could cause gross damage to tissue volumes.

In an exemplary embodiment, microparticles to be delivered to target region within the to the bottom of the epithelium, at the interface with the stroma can comprise: i) carrier formed by 80-89% w/w polyethylene glycol or PDLLA with controlled D content to tune the rate of particle hydrolysis, or other biocompatible and biodegradable polymers (e.g. polylactic-co-glycolic acid, poly(ε-caprolactone) (PCL), polyLactic Acid, poly(3-hydroxybutyrate-co-3-hydroxyvalerate) (PHBV), Chitosan and Cellulose); and an additional 10% w/w 40 to 60 nm tungsten nanoparticle iii) 1-10% w/w drug (e.g. eosin Y or copper sulfate); iii) Polydispersity between 1 and 1.1 to ensure similar penetration; iv) Velocities greater than 100 m/s and/or Ejected using a pneumatic capillary gun. These embodiments can be used for example for corneal cross-linking therapy without debridement of the cornea In some embodiments the microparticle has a density from 7.8 g/cc to 20 g/cc will be placed and the set target region in the upper layers of the corneal stroma. In those embodiments, high density particles. A technique such as laser induced projectile impact testing or acceleration on a polymeric disc with a short aerodynamic relaxation time should be employed in order to get to velocities on the order of 100 m/s.

Density boosting additives, including iron oxides and metal nanoparticles can be added to carrier materials to achieve increased particle density. Another technique to delivery payloads with high density includes using porous metals loaded with therapeutic cargo.

In some embodiments the methods herein described can be performed with combination of components forming a system for controlled ballistic delivery of microparticle to the cornea.

In some embodiments, the system according to the present disclosure comprise a convex microparticle having a diameter from 5 to 30 um and a density from 1 g/cc up to less 20 g/cc, the microparticle comprising the biologically active cargo within a carrier material.

The system further comprises a device configured to ballistically deliver to the cornea the substantially spherical microparticle. The substantially spherical microparticle and the device can be used for controlled ballistic delivery of a biologically active cargo to the cornea of an individual according to methods herein described.

Additional suitable devices can be identified by a skilled person. For example a device that can be used comprises devices for the delivery of genetic materials to the cornea using metal microparticles such as the one described in Zhang et al [6] (see also Example 36).

The systems herein disclosed can be provided in the form of kits of parts. In kit of parts for performing any one of the methods herein described, the related and the reagents can be included in the kit alone or in the presence of device of microparticles compositions. In kit of parts for the treatment of an individual the microparticles and devices for the related application can be comprised together with the reagents formulated for administration to the individual as well as additional components identifiable by a skilled person.

In a kit of parts, the carrier material, cargos, microparticles, devices and the reagents for the related application and additional components identifiable by a skilled person are comprised in the kit independently possibly included in a composition together with suitable vehicle carrier or auxiliary agents. For example, one or more microparticles can be included in one or more compositions together with reagents for detection also in one or more suitable compositions.

Additional components can include the VOAG, a drying column, and labels such as fluorescent compounds to mark the location of microparticles, reference standards, and additional components identifiable by a skilled person upon reading of the present disclosure.

The terms "label" and "labeled molecule" as used herein refer to a molecule capable of detection, including but not limited to radioactive isotopes, fluorophores, chemiluminescent dyes, chromophores, enzymes, enzymes substrates, enzyme cofactors, enzyme inhibitors, dyes, metal ions, nanoparticles, metal sols, ligands (such as biotin, avidin, streptavidin or haptens) and the like. The term "fluorophore" refers to a substance or a portion thereof which is capable of exhibiting fluorescence in a detectable image. As a consequence, the wording "labeling signal" as used herein indicates the signal emitted from the label that allows detection of the label, including but not limited to radioactivity, fluorescence, chemoluminescence, production of a compound in outcome of an enzymatic reaction and the like.

In embodiments herein described, the components of the kit can be provided, with suitable instructions and other necessary reagents, in order to perform the methods here disclosed. The kit will normally contain the compositions in separate containers. Instructions, for example written or audio instructions, on paper or electronic support such as tapes, CD-ROMs, flash drives, or by indication of a Uniform Resource Locator (URL), which contains a pdf copy of the instructions for carrying out the assay, will usually be included in the kit. The kit can also contain, depending on the particular method used, other packaged reagents and materials (i.e. wash buffers and the like).

In some embodiments, methods and systems of the disclosure can be used in connection with therapeutic applications, for the treatment and/or prevention of conditions of the cornea of the individual.

The term "treatment" as used herein indicates any activity that is part of a medical care for, or deals with, a condition, medically or surgically. The terms "treating" and "treatment" refer to reduction in severity and/or frequency of symptoms, elimination of symptoms and/or underlying cause, prevention of the occurrence of symptoms and/or their underlying cause, and improvement or remediation of damage. Thus, for example, "treating" a patient involves prevention of a symptom or adverse physiological event in a susceptible individual, as well as modulation and/or amelioration of the status of a clinically symptomatic individual by inhibiting or causing regression of a disorder or disease.

The term "prevention" as used herein with reference to a condition indicates any activity which reduces the burden of mortality or morbidity from the condition in an individual. This takes place at primary, secondary and tertiary prevention levels, wherein: a) primary prevention avoids the development of a disease; b) secondary prevention activities are aimed at early disease treatment, thereby increasing opportunities for interventions to prevent progression of the disease and emergence of symptoms; and c) tertiary prevention reduces the negative impact of an already established disease by restoring function and reducing disease-related complications.

The term "condition" indicates a physical status of the body of an individual (as a whole or as one or more of its parts e.g., body systems), that does not conform to a standard physical status associated with a state of complete physical, mental and social well-being for the individual. Conditions herein described comprise disorders and diseases wherein the term "disorder" indicates a condition of the living individual that is associated to a functional abnormality of the body or of any of its parts, and the term "disease" indicates a condition of the living individual that impairs normal functioning of the body or of any of its parts and is typically manifested by distinguishing signs and symptoms in an individual.

In some embodiments method and systems of the disclosure can be used in alternative or in combination with, emulsions, ointments, gels, and polymeric inserts to increase the bioavailability of medicine in the cornea.

In some embodiments method and systems of the disclosure can be used in alternative or in combination with nanotechnologies, including dendrimers, cyclodextrins, nanoparticles, liposomes, and polymeric micelles can be combined with the microparticular composition as described. Novasorb®, a cationic emulsion, can be used to deliver latanaprost, a prostaglandin analog used for treating glaucoma. Durasite® is a solution of cross-linked polyacrylamide that can be used to deliver besifloxacin and azithromyacin for the treatment of conjunctivitis.

In some embodiments method and systems of the disclosure can be used to obtain the delivery of high-velocity medicinal microparticles to the anterior surface of the eye.

Biolistic delivery of microparticles to the cornea has several advantages compared to standard topological solutions. First, therapeutic microparticles can be delivered to the surface of the cornea in a uniform, quantifiable layer that will not be redistributed due to gravity and the geometry of the anterior ocular surface. This is expected lead to much more even distribution of therapeutic compounds, which can be beneficial for treatments like corneal cross-linking surgery in which cross-linking density is affected by spatial distribution. Second, the use of ballistic microparticles likely allows for instantaneous traversal of the eye's mucin coat. This barrier can lead to rejection of many negatively charged molecules.

Additionally, the medicinal particles embed in the corneal epithelium, remain fixed in place, and slowly dissolve to release therapeutic compounds to surrounding tissue volumes. In particular, embedding a micro particle in corneal tissue allows for bioavailability of compounds for a long duration of time. If particles are embedded in tissue, fixing them in place, they can dissolve over a period of several hours, leading to more effective uptake of a medicine.

Further details concerning the identification of the embodiments of methods and systems of the disclosure and related compositions, that can be performed in combination with such devices can be identified by the person skilled in the art upon reading of the present disclosure.

EXAMPLES

The methods and system herein disclosed are further illustrated in the following examples, which are provided by way of illustration and are not intended to be limiting.

The following material and methods were used in performing the experiments reported in the following examples.

Drying Column Used for Microparticle Preparations

A drying column was built for the production of solid polymeric microparticles. In particular one-meter-tall 10-cm-diameter drying column was wrapped in heater tape (about 3.6 meters of tape with a width of 5 cm; McMaster Carr). The tape was controlled with a CN142 temperature controller (Omega Engineering) that was used to drive a solid-state relay controlling power to the heater. The temperature controller was receiving input from a K-Type thermocouple attached between the heat tape and the wall of the glass column. This allowed us to have more control over heat tape, preventing overheating. Two T-Type Process Heaters (Omega Engineering; Item #AHP-5052) were used to heat the carrier gas (fed to the top of the column) and the dilution gas (fed to the bottom of the column). The carrier gas was used to dilute the air in the column and to carry the particles gently to the particle trap. The dilution gas was fed directly to the particle trap to dilute vapor in the column and prevent condensation. Another CN142 temperature controller was used to control the temperature of the inline heater feeding the carrier gas to the column. The other inline heater was wired in series with the first heater, giving it indirect temperature control. Three flow control-valves with rotameters were used to control 1) the carrier gas flow, 2) the dilution gas flow, and 3) the dispersion gas flow being sent directly to the VOAG (gases labelled in FIG. 1). The dispersion gas was meant to disperse droplets radially as they enter the column, thus improving drying and hopefully reducing droplet coagulation. Since the column is configured to produce respirable microparticles and vapors from organic solvents, the entire apparatus was placed inside a tent enclosure with a duct connected to the house ventilation system. This setup allowed for containment of hazardous materials, and also kept the column at a workable height. In general, this design of the drying column was made to effectively dry microparticles, to dilute the vapors exiting the bottom of the column, and to fully contain the aerosols produced within.

Monodisperse Aerosol Generator:

A Vibrating orifice aerosol generator (VOAG) a device known to create monodisperse droplet described in Berglund, & Liu, (1973) [25] [was used The orifice is made of a precision pinhole laser-drilled into a thin foil disc (Edmund Optics). It is an element that can be interchanged when a different outlet size is required or when the orifice has become obstructed. The piezoelectric element is a 2.5-cm-diameter disc punched out of 75-μm-thick steel shim stock fixed to a piezoelectric ceramic (7×8 mm; Stem Inc.) using silver epoxy. When initiating a jet, the tubing which carries fluid away from the device is capped, introducing a step change in pressure. The piezoelectric ceramic is controlled using a function generator (Agilent 33220a) with sinusoidal waveforms oscillating between positive and negative five volts. There is an input for compressed air on the device that disperses microparticles ejected into the particle drying column.

The mount used to place the VOAG on top of the column centered and helped disperse the aerosol being fed to the drying column. Mounts were built that used a quick, diagnostic test to see if droplets were being produced in a monodisperse manner. With the jet initiated, a stream of gas was directed orthogonally at the droplet-train. If the flow of the gas was laminar and the frequencies being provided to the VOAG were in the range of monodisperse breakup, then the liquid would be deflected as a kinked ray, instead of a spray. This phenomenon is demonstrated in. With no excitation, particles are deflected in a spray because the distribution is polydisperse and droplets have different characteristic aerodynamic relaxation times. When a 19 kHz signal is applied to the microjet, a clean ray of particles is deflected.

Oscillatory Shear Rheology

To measure the viscosity of PEG solutions, a strain-controlled oscillatory shear rheometer was used (ARES 4100). An 80 mm cone-shaped geometry (4° degree cone angle) was used with a 50 μm gap. Samples were tested on the rheometer with low strain rates compared to particle impacts (from 1 to 1001/s) and n=5 measurements were recorded per solution.

Aerosol Flowrate Measurement

To measure the flowrate of fluid ejected from orifice pinholes, liquid was collected in 1.5 mL conical microcentrifuge tubes for thirty seconds. At the end of collection times, the mass ejected from the pinhole was measured. Using the diameter of the pinhole, the velocity of incompressible fluid exiting the orifice was calculated. Measurements were recorded six times for each viscosity of fluid tested.

Custom High-Speed Imaging System

When imaging aerosols, the a-\ was used to record images of shadows cast by moving droplets. The VOAG was mounted on top of a hollow poly(ethylene) cylinder. Aerosols were illuminated with either a continuous lamp or a bright pulsed-LED (VLP-4830-25; VAL Electronics). The former was used to measure broad polydisperse size distributions. The pulsed-LED was used to visualize monodisperse size distributions when more resolution was desired. Aerosols were imaged three centimeters from the outlet of the VOAG. A Chronos 2.1-HD high speed camera (Krontech) was used for these studies. It was run at 1024 frames per second to maximize camera resolution (1.3 megapixels). There were two separate microscope objectives used in this study, 2× and 10× magnification lenses (Mitutoyo). The lenses have a 33.5 mm working distance. The 2× objective was used to measure aerosols not being exposed to piezoelectric agitation (with the continuous light source and a 1 μsec exposure time). The 10× objective was used for monodisperse aerosols (with the pulsed light source). The LED flashes for a duration of 10 μsec at the start of every ten milliseconds.

Image Processing Pipeline

To record droplet size distributions from high-speed video, an image processing pipeline was written in Python (Appendix A.2). Binary images were generated that turned camera frames into 2D plots that show information describing what pixels contain outlines of droplets. Since droplet data often had different degrees of background lighting, threshold pixel values were chosen on a video by-video basis. Threshold values were increased until droplet objects no longer increased in size. Once masks were generated from image data, regionprops, an open-source Python function, was used to locate objects and record their major and minor axis dimensions. The major axis was indicated by where the droplet was at its widest and the minor axis was where it was the smallest. Droplet diameters (major axes) were recorded if major:minor axis ratios were less than 1.3 and droplets were not connected. These criteria were included to reject droplets that had not yet relaxed after breaking up from the capillary jet, to reject droplets that had not yet broken up, and to reject droplets colliding. Data from individual frames were saved and plotted. Droplet size-distributions of polydisperse aerosol trains were reduced to whisker plots using bokeh, another open-source Python package.

Assessment of Tissue Damage Using Confocal Microscopy

Confocal microscopy was done on tissue treated with stainless steel microparticles prior to staining with picosirius red (from Abcam Inc.). Picosirius red is a fluorescent dye that binds strongly to collagen fibrils and also stains epithelial tissue. Sections of tissue were cut to 30 μm thickness and were then stained for 5 minutes. This was sufficient to produce bright fluorescence on the stroma and the epithelium. Tissue was inspected using a Zeiss LSM 710 inverted confocal microscope. Z-stacks were recorded (30 μm depth) to show how the tissue is damaged as a result of microparticle impact.

Example 1: Preparation of Microparticles Using a Drying Column

Microparticles were prepared using a drying column schematically described in FIG. 2.

In particular, nitrogen was fed to the VOAG (dispersion gas), to the top of the column (carrier gas), and to the particle trap (dilution gas). In particular, the dispersion gas flow was set by monitoring the state of the aerosol jet at the top of the column using a borescope. The flow was increased to 10 SCFH until the jet just started to move with the dispersion gas. A flowrate of 30 SCFH was chosen for the carrier gas. This resulted in an approximate velocity of gas moving through the column of 3 cm/s. Dilution gas was set to 10 SCFH.

The column walls are heated to a certain temperature and the VOAG usually ejects a ~200 mgs of solution a minute, if the 35 μm pinhole is used. A previous drying simulation indicates that if droplets made of ethanol can be aerosolized with diameters less than or equal to 100 μm, then solid microparticles can be formed in the one-meter-tall drying column.

At steady state with a 35 μm pinhole ejecting fluid into the column at 0.1 g/min, the column gas temperature was 100° C. (measured ⅔rd's of the way up the column with a temperature probe). The inline heaters were set to 250° C., resulting in a steady state gas temperature of 80° C. for the nitrogen going into the column. The VOAG using a 35 μm pinhole was excited at 35 kHz to try and produce droplets that were around 70 μm.

These are the typical conditions at which particle preparations were run at.

Example 2: Flowrate Characterization of Aerosolized Particles

In order to characterise the flow rate used to provide microparticles with a drying column with a procedure exemplified in Example 1, 50 and 75 μm pinholes were used to aerosolize solutions that have viscosities from 1 to 40 centipoise.

Solution viscosity follows the following power law expression, where c is the weight fraction of PEG in solution.

$$\mu = 1955.2c^3 - 368.7c^2 + 61.0c + 0.3. \tag{4}$$

Figure 3:
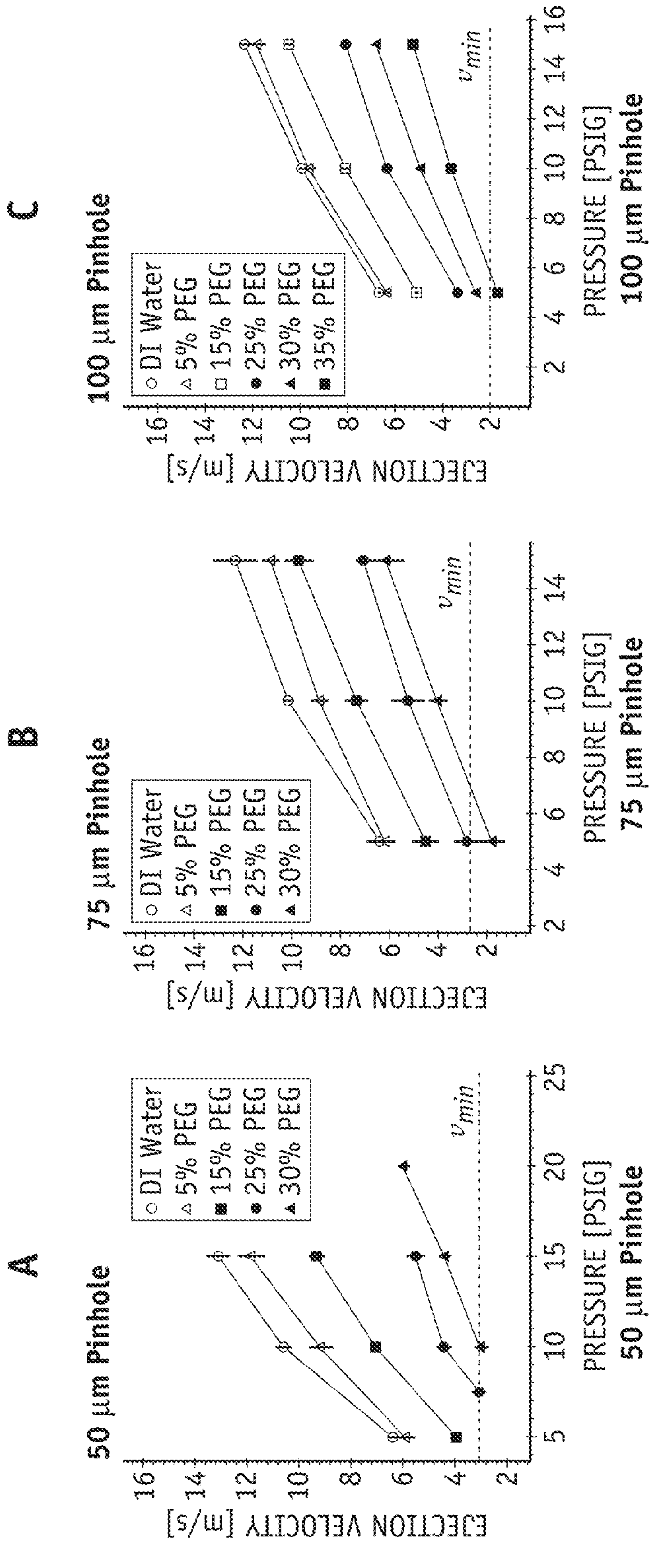
FIG. 3 shows charts illustrating mass flowrate and ejection velocity for different pinholes with PEG solutions of different concentration. The mass flow rate (top) and ejection velocity (bottom) for three pinholes is plotted for a set of different PEG solutions. N=6 measurements. Error bars show 95% confidence intervals. Dotted lines show $v_{min}$, predicted by Equation 2 as reported in Lindblad 1965 [3], wherein that $v_{min}$ scales inversely with jet diameter $D_j$, density ρ, and the liquid's surface tension in ambient air σ, namely, $$v_{min} = \sqrt{\frac{8\sigma}{\rho_l D_j}}. \tag{1}$$
Figure 4:
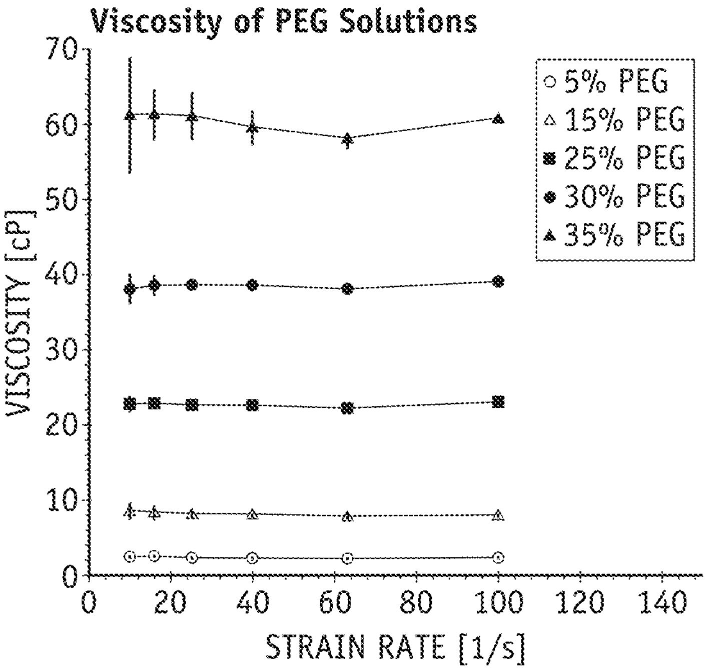
FIG. 4 shows a diagram reporting the oscillatory shear rheology of PEG solutions. Strain sweeps for five different PEG solutions from 10 to 1001/s. Each point is from n=5 tests. Error bars show 95% confidence intervals.

The results of flow characterization studies are shown in FIG. 3 and the viscosities measured for solutions tested in this study are shown in FIG. 4

The data for the 50 μm pinhole shows that when solution viscosity reaches 20 cP, the lowest aerosolization pressure tested increases slightly from 5 to 7.5 PSI. This is because, at 5 PSI, the aerosol could not be initiated and maintained for more than a few seconds. When testing 30% PEG, the minimum pressure tested increases further to 10 PSI. This behavior suggests that a minimum pressure is needed for aerosol formation. FIG. 3 also plots the ejection velocity.

Ejection velocity for a given pressure is similar between pinholes. Dotted lines indicate the theoretical minimum jet velocity predicted by Equation 2. The theoretical minimum ejection velocity was predicted accurately for the 50 μm pinhole, but jet velocities below the predicted value were measured for data with the 75 and 100 μm pinholes.

Solutions were tested with higher viscosity (60 and 80 cP), but they were found to be exceedingly difficult to form droplet trains. When pinhole size was increased to 100 μm, the VOAG was able to aerosolize a 60 cP solution. The range of viscosities reported represent a range that can be aerosolized reliably with the VOAG used in this study.

Figure 5:
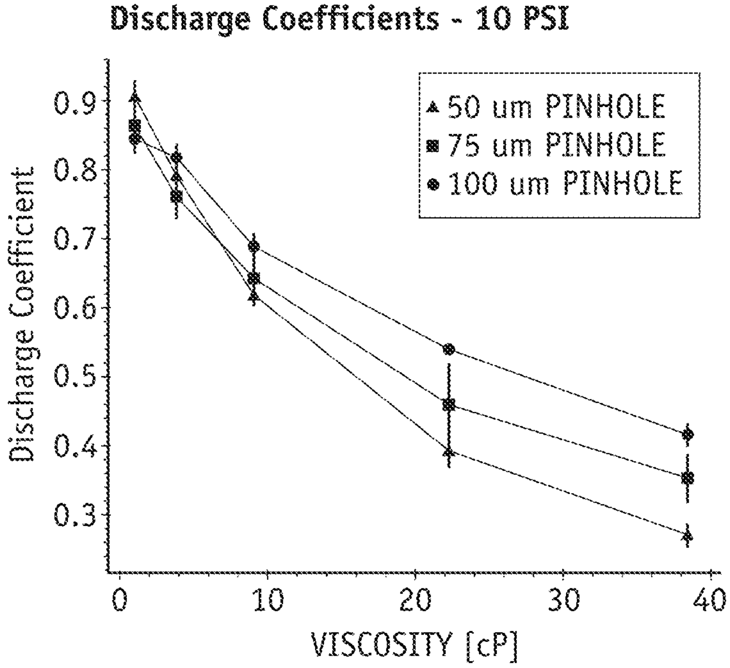
FIG. 5 shows a diagram reporting the discharge coefficient as a function of viscosity. At 10 PSI, the discharge coefficient of each pinhole is recorded. N=6 samples per data point. Error bars show 95% confidence intervals.

Higher pressures were applied (up to 60 PSI; 4.21 bar), and they did not lead to jet initiation when viscosities were greater than 60 cP. FIG. 5 shows how $C_D$ changes in the aerosol generator.

Example 3: Size Distribution. Of Aerosolized Microparticles

Figure 6:
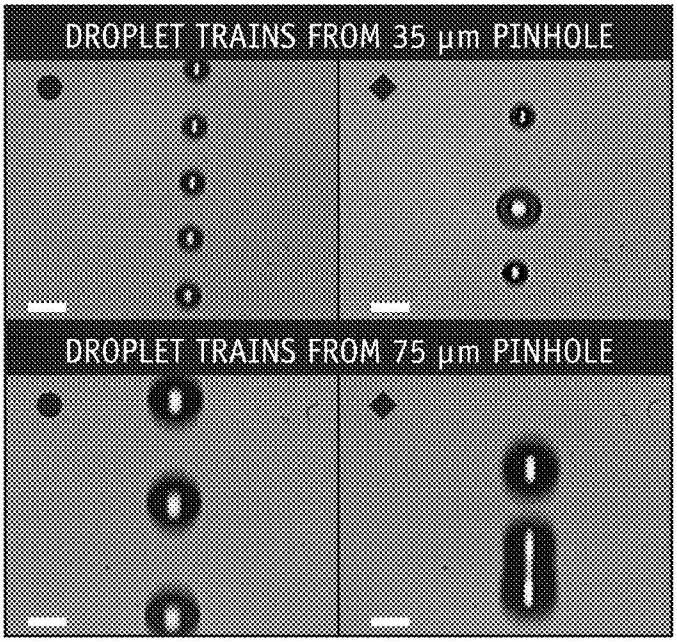
FIG. 6 shows a chart of representative micrographs of aerosols emitted from different pinholes (10× Objective; strobing light–1 msec exposure time). Light exposure is 10 microseconds when recording of trains of ♦ monodisperse and ● polydisperse droplet trains. 100 μm bar shown.
Figure 7:
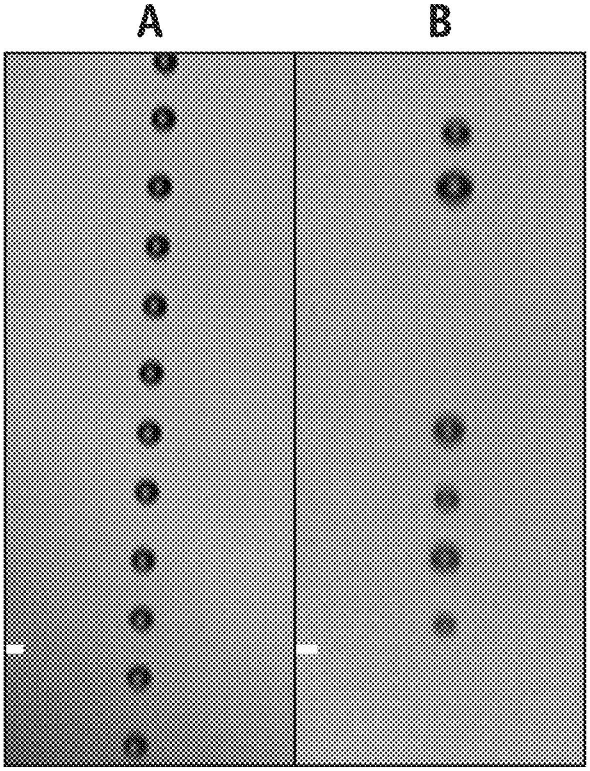
FIG. 7 shows micrographs of aerosols emitted from a 35 μm pinhole (2× Objective; bright continuous light source—1 μsec exposure time). In particular FIG. 7 Panel A) shows monodisperse aerosol excited at 35 kHz and FIG. 7 Panel B) shows polydisperse aerosol excited at 60 kHz. 100 μm error bars shown.

To measure the size distributions of viscous solutions aerosolized by the VOAG, the image processing pipeline (Appendix A.2) went through frames one by one thresholding and acquiring droplet data. Representative images of aqueous aerosols measured with 10× and 2× objectives are shown in FIG. 6 and FIG. 7 respectively and related size distribution are shown in FIG. 8.

These figures indicate the dichotomy between monodisperse and polydisperse aerosol size-distributions. Monodisperse aerosols show identically sized objects with uniform spacing. Polydisperse distributions are characterized by non-uniform spacing between droplets and aspherical shapes, which are formed from insufficient time for drops to relax following droplet breakup or collisions between droplets of different size/characteristic acceleration times. The 10× objective which produced FIG. 6 was used to measure droplet size from monodisperse aerosols (for better size resolution than the 2× objective). Despite slight motion blur in the images, this study was capable of measuring diameters accurately by recording the major axis perpendicular to the velocity vector.

Figure 8:
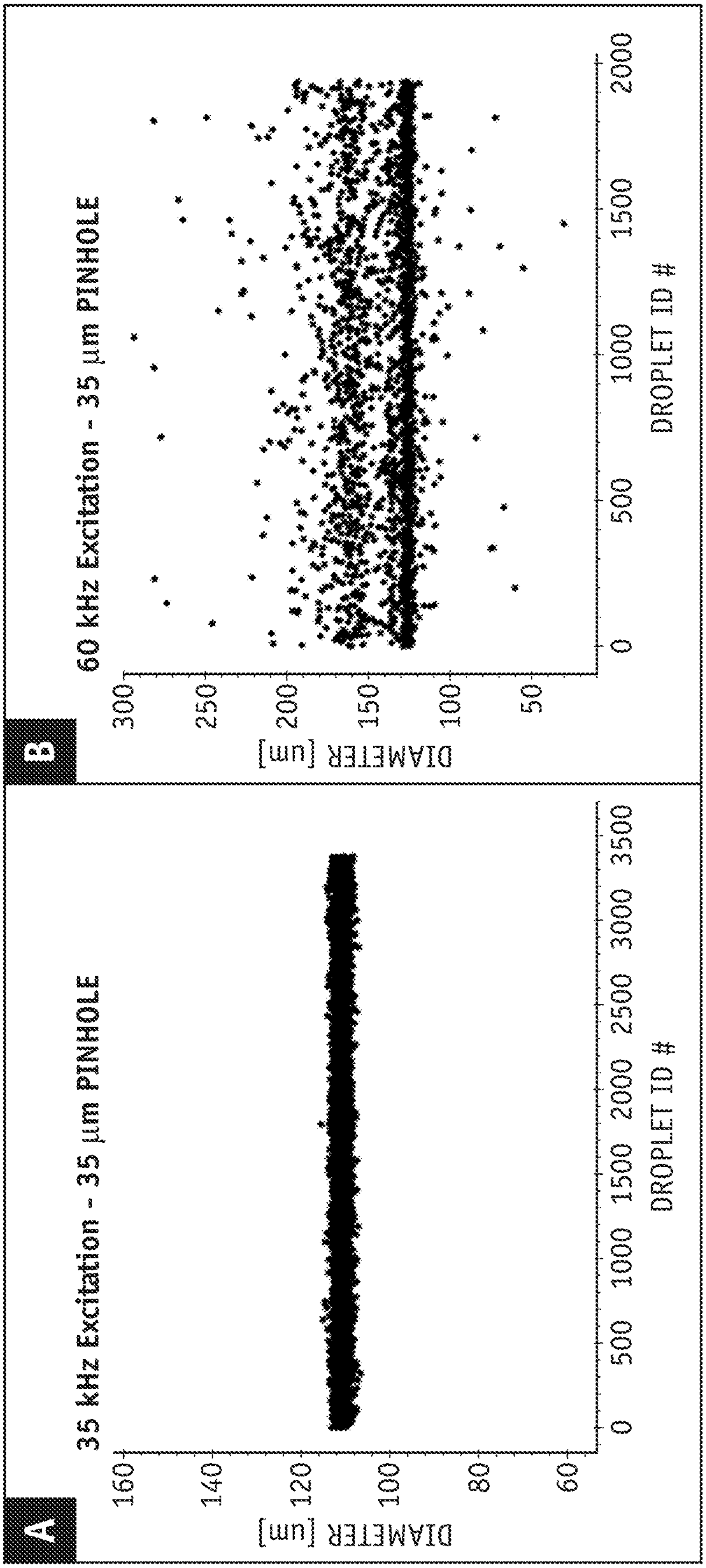
FIG. 8 shows charts illustrating size distribution for aerosol formed from water emitted by a 35 μm pinhole. Size distributions show the droplet-sizes recorded from two separate high-speed videos (three and two seconds long). The x-axis shows the droplet ID number from videos which increases with elapsed time. In Particular FIG. 8 Panel A shows droplets from an aerosol excited at 35 kHz.

Size distributions, like those shown in FIG. 8 were recorded for a range of viscosities using a 75 μm pinhole. These graphs, which show individual droplet size over time (denoted by Droplet ID number—a sequential numerical marker), describe the same monodisperse and polydisperse aerosols shown in FIG. 7 Using Image J on FIG. 7 Panel A droplet size measured around 110 μm, indicating good accuracy of the image processing pipeline. \ FIG. 7 Panel B shows a polydisperse distribution, with high number density around two different sizes.

Example 4: Effect of Viscosity and Pinhole on Droplet Sizes Produced

Figure 9:
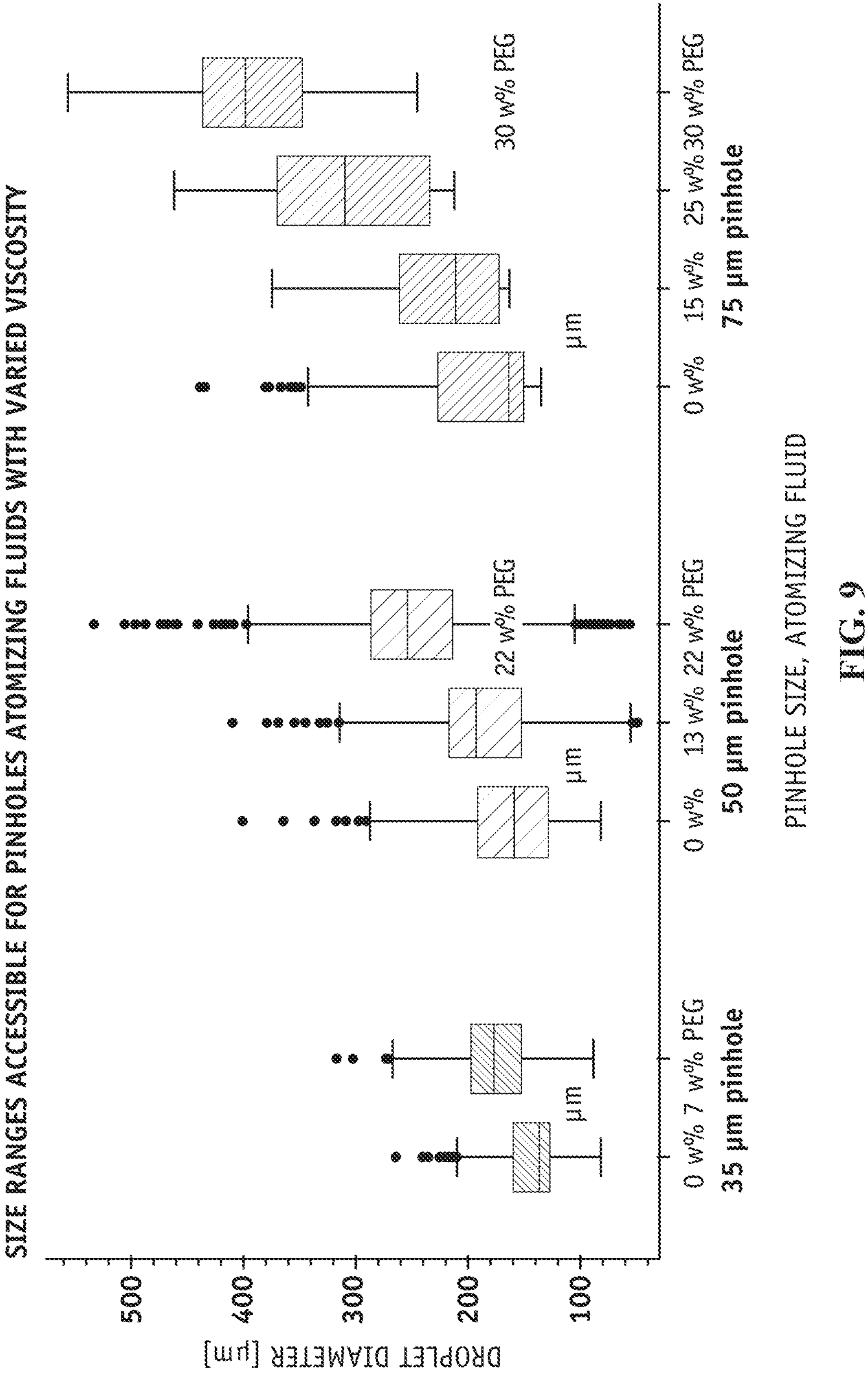
FIG. 9 shows a diagram illustrating size distribution of viscous aerosol droplets from orifice pinholes without piezoelectric excitation. Box-plots summarize the size-distribution of aerosols emitted from three different pinholes with a range of PEG solutions. Driving force for aerosolization was 0.3 bar.

The size distribution of polydisperse, non-excited droplet-trains was recorded. The data is represented using a boxplot in FIG. 9. Boxes show the interquartile range (IQR), and whiskers show the lowest datapoint still within 1.5 times the IQR. Black points on these figures indicate outliers in the dataset. The data shows significant increases in droplet-size as viscosity is increased. Using the power law expression in Equation (5), an increase in viscosity from 1 to 3.4 cP for the 35 μm pinhole (using 7% PEG as the weight fraction) results in a significant increase in droplet size. The mean droplet size increases from 148.3 μm to 173.5 μm and the IQR shifts as well. Thus, an increase in viscosity, which has minimal effect on the mass flowrate of a given pinhole, can still have a significant effect on the breakup of a capillary jet into droplets.

The effects seen in 50 and 75 μm pinholes also show significant changes with increased viscosity. Using a 13% w/w PEG solution (6.3 cP), the mean droplet size shifts from 162 μm to 181 When a 22% w/w solution is used (16.7 cP), the mean droplet size shifts to 241 μm and the IQR shifts from 3 to 4 pinhole diameters to between 4.5 and 5.5 orifice diameters. The 75 pinhole showed a large range in droplets produced. Testing the solution that was ~40 cP in viscosity, droplets were made that were five to six times the diameter of the orifice.

These data indicate that the VOAG is sensitive to changes in viscosity and altering solution viscosity can lead to a much wider range of droplet sizes that can be used.

Example 5: Production of 70 to 175 Um Droplets Using Atomization of Alcohols

To test low-viscosity, high-volatility liquids like ethanol and isopropanol, a 75 μm pinhole was first used. Isopropanol was filtered and then the flowrate was measured using a pressure of 0.34 bar. The average volumetric flowrate of isopropanol was measured to be 1.49 cc/min. This corresponds to an ejection velocity of $$v = \frac{\dot{Q}}{\frac{\pi}{4}D_o} = \frac{\left(14.9\frac{\text{cm}^3}{\text{min}}\frac{1\text{ min}}{60\text{ sec}}\right)}{\frac{\pi}{4}(.0075\text{ cm})^2}\frac{1\text{ m}}{100\text{ cm}} = 5.6\text{ m/s},$$

where $\dot{Q}$ is the volumetric flowrate and $D_o$ is the orifice diameter.

When comparing this with the data shown in \ FIG. 3, it can be seen that the expected ejection velocity was 6.0 m/s±0.5 m/s, so the pinhole was considered to be clear and unobstructed. Next, the expected range of frequencies leading to monodispersity was calculated. The high-end range of frequencies is given by λ=3$D_1$ in Equation (4), where $D_j$ is the jet diameter, which is approximated using the diameter of the orifice. This disturbance wavelength leads to a frequency of $$f = \frac{v}{3D_o} = 25.0 \text{ kHz}.$$

Figure 10:
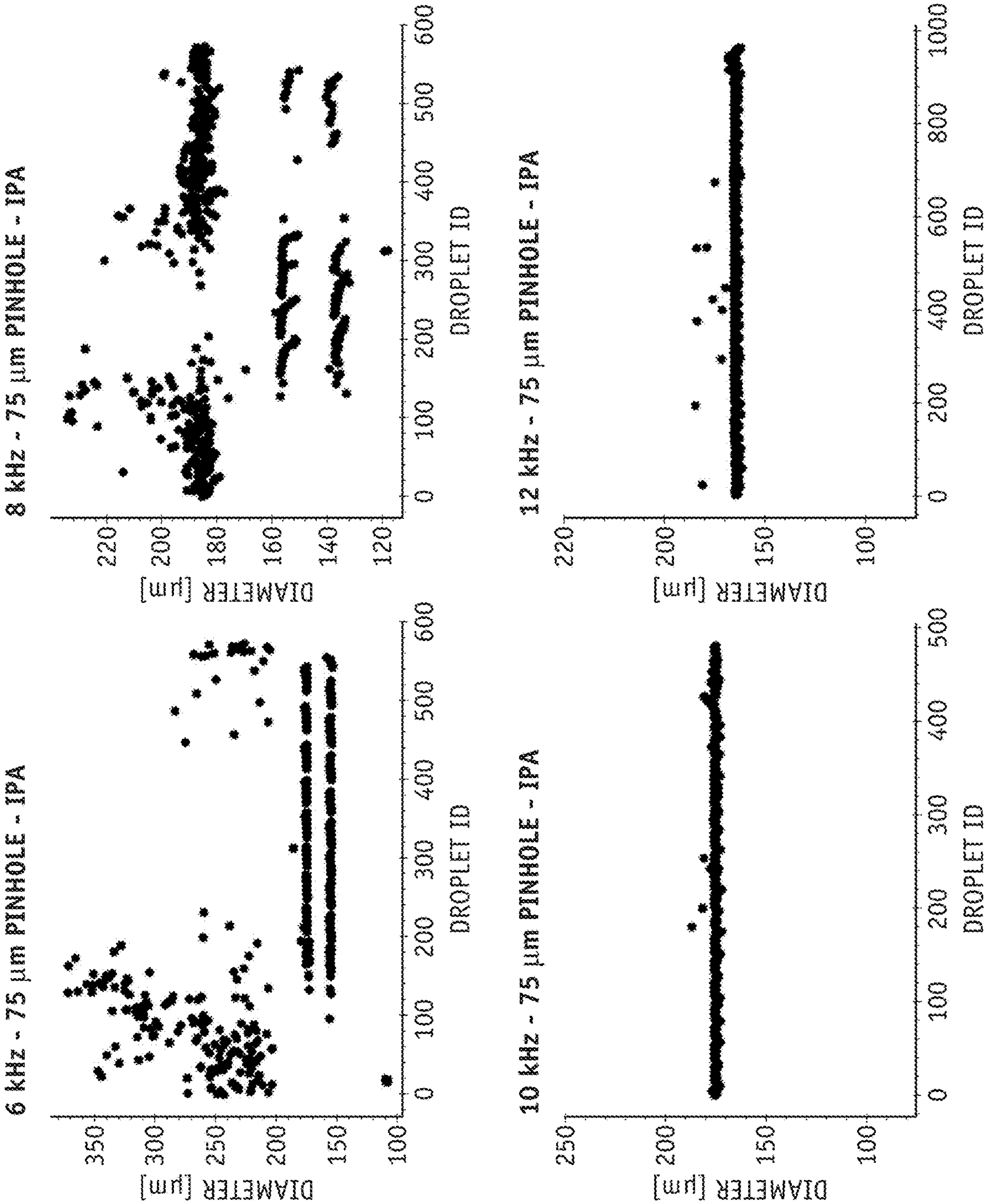
FIG. 10 shows charts illustrating size distribution of isopropanol ejected from a 75 pinhole (6 to 12 kHz). Lower frequencies show bimodal and even trimodal distributions of droplet size. Then, when the expected region of monodisperse frequencies is entered, there is a shift to monodisperse droplet production.
Figure 11:
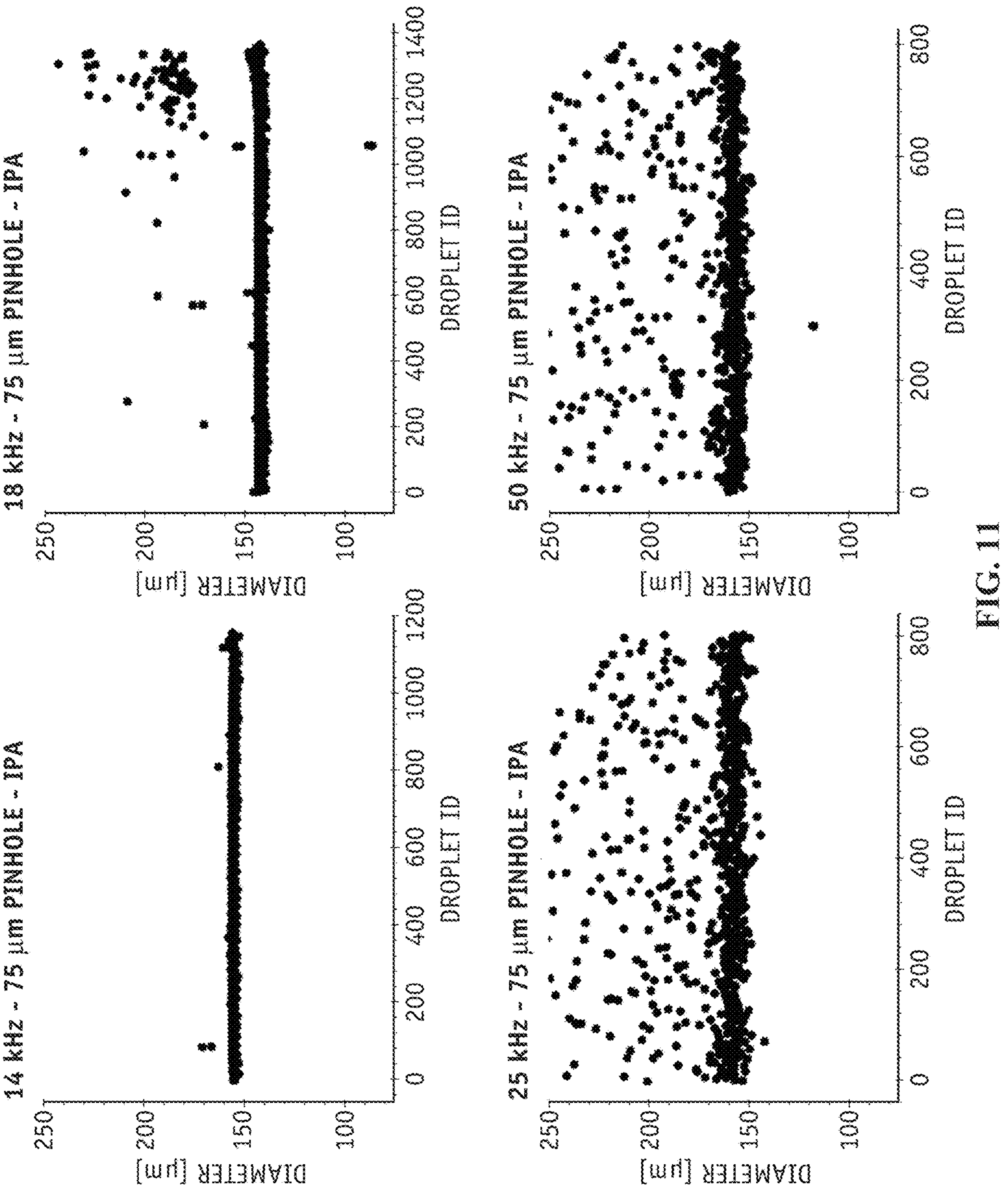
FIG. 11 shows charts illustrating size distribution of isopropanol ejected from a 75 pinhole (14 to 50 kHz)—monodisperse production occurs up until 18/19 kHz. Then at 25 kHz and 50 kHz, the production of droplets is essentially the same as if the orifice were not being excited at all.

The low end of expected monodisperse frequencies is 10.7 kHz. Based on these calculations, frequencies were chosen below this range (6 and 8 kHz), within this range (10, 12, 14, and 18 kHz), as well as size distributions greater than this range of frequencies (25 kHz and 50 kHz). The size distributions measured in this analysis are shown in \ FIG. 10 and FIG. 11.

Example 6: Preparation of Monodisperse Microparticles with Controlled Sizes

A 35 μm pinhole was chosen to produce monodisperse aerosols and in particular 70 μm to 120 μm droplets formed with ethanol. If the generator was operated at around 35 kHz, 70 μm droplets could be produced by the VOAG. With this droplet size, an expected final particle diameter can be calculated using the following conservation equation:

$$D_p = C_v^{1/3} D_d \quad (5)$$

where $D_p$ is the diameter of the particle, $D_d$ the diameter of the droplet, and is the volumetric concentration of solute. For a 70 μm droplet with concentration of 1% to 5% w/w, the expected final droplet size comes out to 15 to 26 μm. For a 100 μm particle, the expected final particle size comes out to 21 to 36 μm.

This size range is in the range of previously tested ballistics, so these conditions can be selected for particle preparations.

Figure 12:
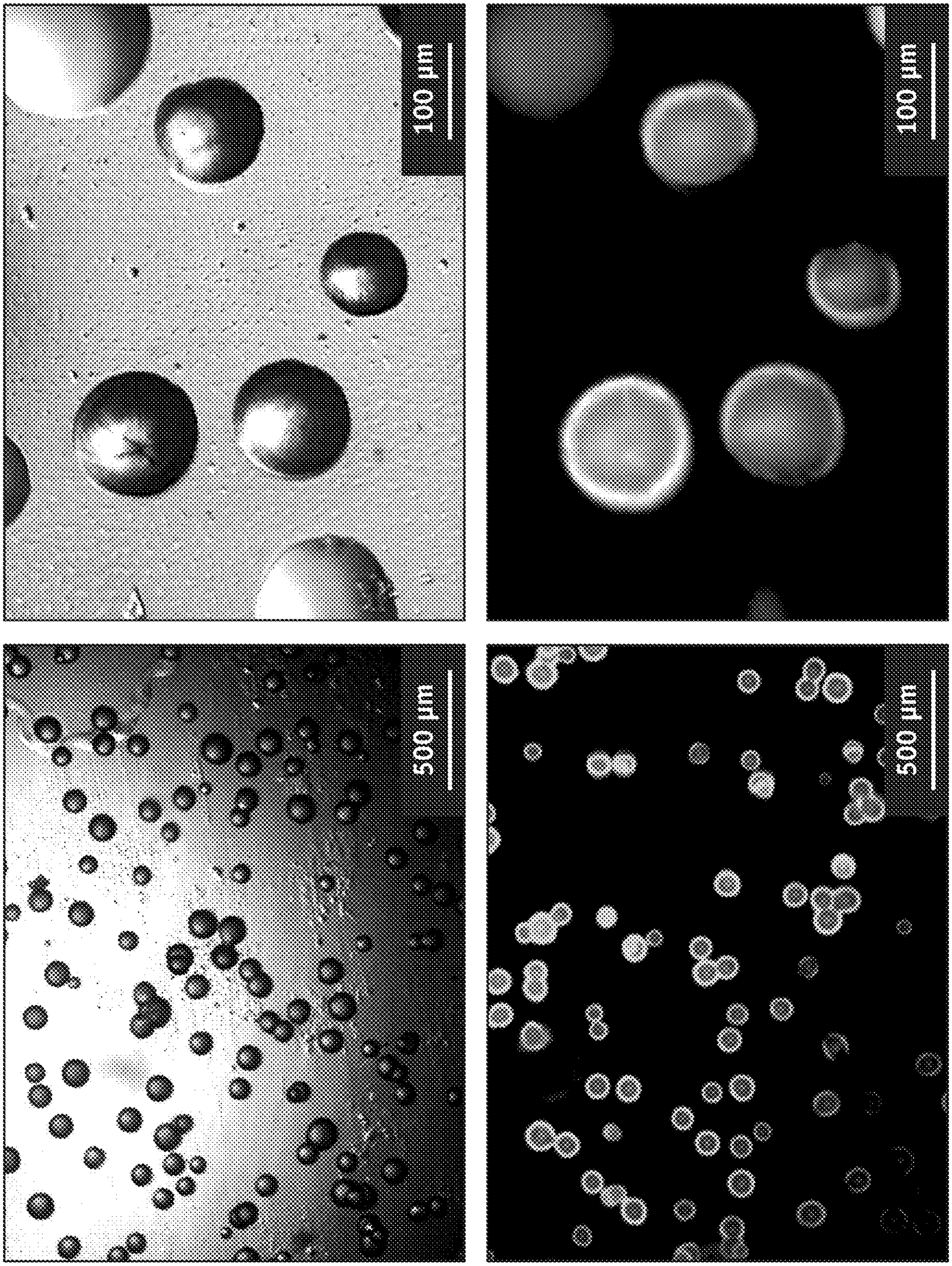
FIG. 12 reports pictures showing PEG microparticles made with 1% w/w Eosin Y using 50 μm pinhole. These microparticles were formed using the protocol described herein. The particles had a flattened morphology from relaxing on the bottom of the petri dish. As seen in the top-right image, particles were not fully dried in the process.

Microparticles with different sizes and densities can be prepared using a drying column in view of the indications of Examples 1 to 5 as will be understood by a skilled person Example 7: Description of Microparticles Formed The Using the drying column, several samples of PEG microparticles were prepared. PEG was used due to its biocompatibility and its relatively high density for a polymer (1.125 g/cc). FIG. 12 shows the particles that are produced using the 50 μm pinhole, which may not be fully dry. The microparticles formed in this particle preparation were made using a 50 μm pinhole receiving excitation at 17.5 kHz. These images show a distribution of particles that is polydisperse. The microbeads that appear dry are 50-80 μm.

The polydispersity is likely due to a distribution of residence times in the column and potential coagulation of droplets. In addition, while monodispersity is checked at the beginning of runs, it is quite likely that particulate matter builds up on the orifice leading to periods where the aerosol is no longer monodisperse. One other interesting facet of these images is the dark stained ring surrounding particles. In many particle preparations that resulted in wet microparticles, this ring phenomenon is observed. The predominant theory for this observation involves the diffusion of charged solutes in wet droplets to the interface between droplet and air. This can lead to subsequent crystallization on the surface, poor drying, and hollow morphologies.[22]

Figure 13:
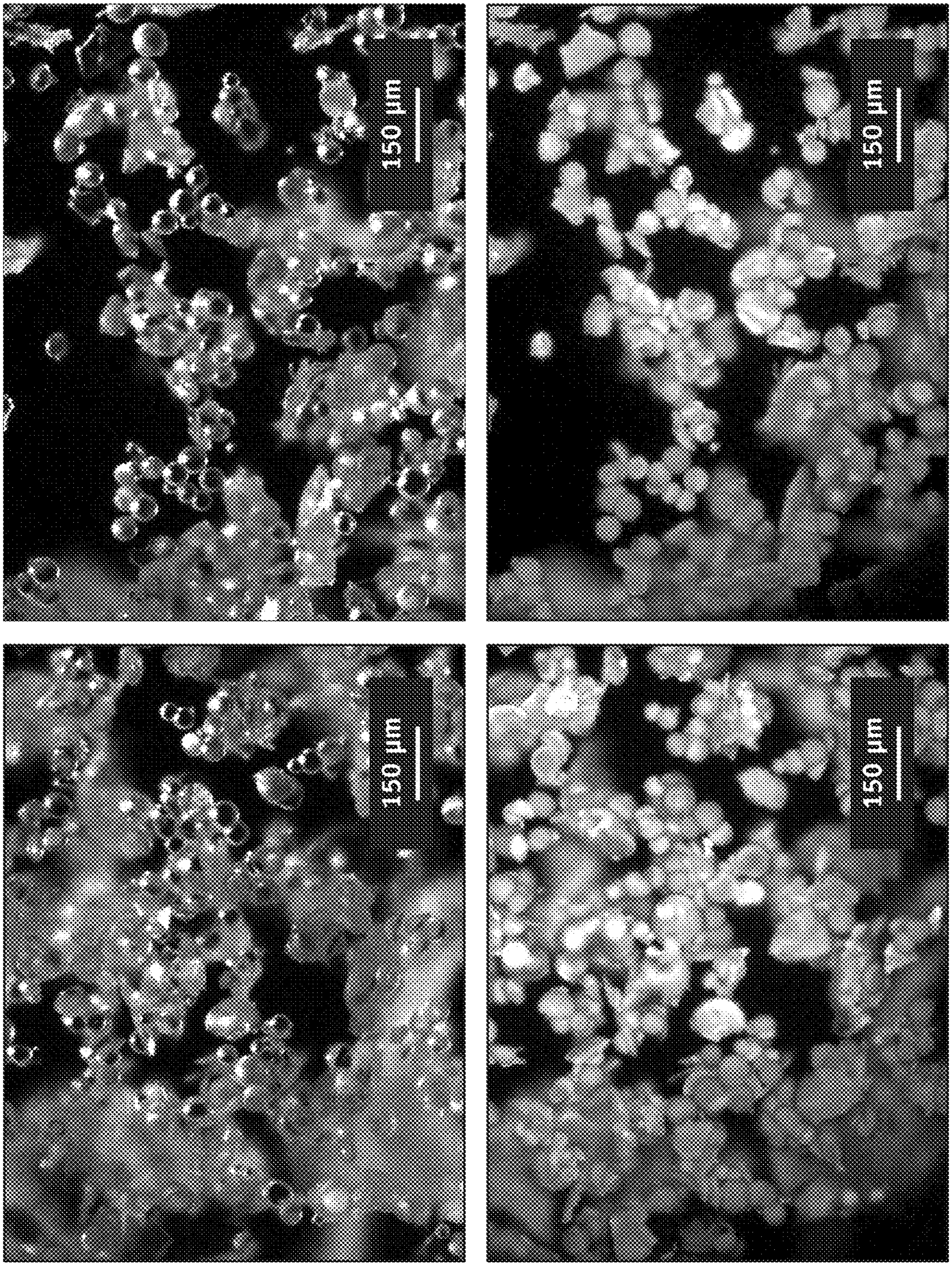
FIG. 13 reports pictures showing PEG microparticles made with 1% w/w Eosin Y using 35 μm pinhole. The particles were smaller than those formed with the 50 μm pinhole. The particles are round, solid, and stick to one another.

When a smaller pinhole was used, particles like those shown in FIG. 13 were formed. In these figures, clusters of particles can be shown sticking together. There is no discernible Eosin Y ring on these particles, possibly because charged solutes do not have enough time to diffuse to the surface of the droplet before drying. The solid microparticles are all under 50 μm. There was also a good amount of PEG that crystallized on the bottom of petri dishes. This material was scraped up with the rest of the microparticles. Nonetheless, this particle preparation was a success, because it achieved essentially dry microparticles that are in the same size range as our previous ballistics testing. With these particles set aside and stored under vacuum, they were ready to be placed on macrocarriers and used in our ex vivo ballistics experiments.

A skilled person will understand that a solution can be aerosolized into the column using tungsten, acoustic agitation, and a larger pinhole, but the heat duty of the column is going to need to be increased to dry the larger droplets.

Example 8: Preparation of Microparticle with Biologically Active Cargo

To form particles in the drying column, the following procedure was developed. A solution of poly(ethylene glycol) (PEG 10 kDa $M_w$; Alpha Aesar) was prepared by heating and stirring in 96% ethanol (VWR) until the solution reached 35° C. and was stirred for another half hour.

A cargo is added by appropriate procedure based on the type and amount of cargo to be included. In the case of 1% w/w Eosin Y microparticles, 3.96 grams of PEG was dissolved in 96 grams ethanol along with 40 mgs of Eosin Y salt (Sigma Aldrich). The solution was cooled to room temperature and filtered with a 0.45 μm cutoff syringe filter. (see Example 8)

The solution can be loaded into the VOAG and a microjet was initiated. After checking monodispersity of the aerosol stream using the impinging jet method of Example 3. (FIG. 7), the VOAG was mounted on top of the column without having engaged any heating. Once the aerosolizer was mounted, temperature controllers were turned on along with gas inputs. While the column was heating up, the bottom of the particle trap was left open so vapor and condensed liquid could drip out.

After one hour of heating and feeding the aerosol jet into the column, the particle trap was connected to the collection chamber and a glass petri dish was inserted to collect settling particles. The column was run for one-hour intervals, at which time dried particles would be collected and a fresh petri dish would be placed in the collection chamber. With low flowrates of 0.1 to 0.2 mL/min, the 50 mL fluid reservoir would last for a few hours. If solution ran out, fresh solution would be refilled, but often this would lead to obstructions building up in the pinhole during column downtime.

The petri dishes were placed in a vacuum oven at ambient temperature and vacuumed down to 125 mmHg. After drying overnight, the particles were scraped up using a razor blade and stored in a scintillation vial. In general, the yields were low. About 40 mgs of particles could be collected over a preparation that lasted four hours and used 100 mL of particle solution (1% yield)

Example 9: Preparation of Microparticles Comprising Eosyn Y as Cargo and PEG as Carrier To poly(ethylene glycol) (PEG) microspheres with 1% w/w Eosin Y were prepared using a spray-drying technique.

A vibrating orifice aerosol generator (Berglund et al., 1973[25]) with a 35 μm pinhole ejecting droplets at 5 m/s with a piezoelectric ceramic vibrating at 30 kHz was used to produce droplets of 3.96% w/w PEG with 0.04% w/w Eosin Y in 96% v/v ethanol.

Droplets fell through a 1-meter-tall 10-cm-diameter drying column equipped with ports for heated, dry gas. N2 at 100° C. with a flowrate of 30 standard cubic feet per hour was used to heat and carry the smaller particles through the column. Large (100 μm) droplets had a settling time in the column of around 5 seconds.

Microparticles were collected at the bottom of the drying column and further dried in a vacuum oven overnight (at ambient temperature) before being placed on macrocarriers.

The size distributions of this particle preparation resulted in particles of sizes 30 to 50 μm. In the end, the broad library of microparticle size and composition that was desired could not be produced, due to time constraints and difficulties avoiding pinhole obstruction. With higher heat duties to the column, slightly larger pinholes, and improved dispersion of droplet trains entering the column, it is expected that it will become easier to make dry microparticles. A rich potential research project involves making particles containing density-boosting metal nanoparticles to increase the embedding energy of therapeutic microparticles.

Example 10: Selection of Gel Substrate for Ballistic Experiments

Before testing a Pneumatic Capillary Gun (PCG), a convenient gel target was required that had similar mechanical properties compared to corneal tissue. Agarose gels can be prepared quickly and are transparent, which is a benefit for ballistics experiments. Based on previous work done by Professor Groisman, agarose was selected as the substrate material. Oscillatory shear rheology was performed on a range of agarose gels using an 8 mm diameter geometry. To make gels, agarose was dissolved in DI water by microwaving until boiling. Using a Pasteur pipette, the boiling solution was poured in between two acrylic plates clamped around 0.7 mm spacers with rectangular slots for the solution to flow into. The gels were allowed to set at 4° C. for two hours. The gels were cut into discs using an 8 mm biopsy punch. Tissue samples were prepared by dissecting the cornea from porcine eyes and punching out an 8 mm disc from the center of the tissue using a biopsy punch. When testing tissue, an 8 mm cleated geometry developed by our lab was used to prevent wall slip [26] [27]. To test samples, the rheometer geometry was lowered onto samples until a normal force was registered. Strain sweeps were run on a stress-controlled rheometer (TA Instruments; AR1000) from 1 to 1001/s with eight points per decade (at 25° C.).

Figure 14:
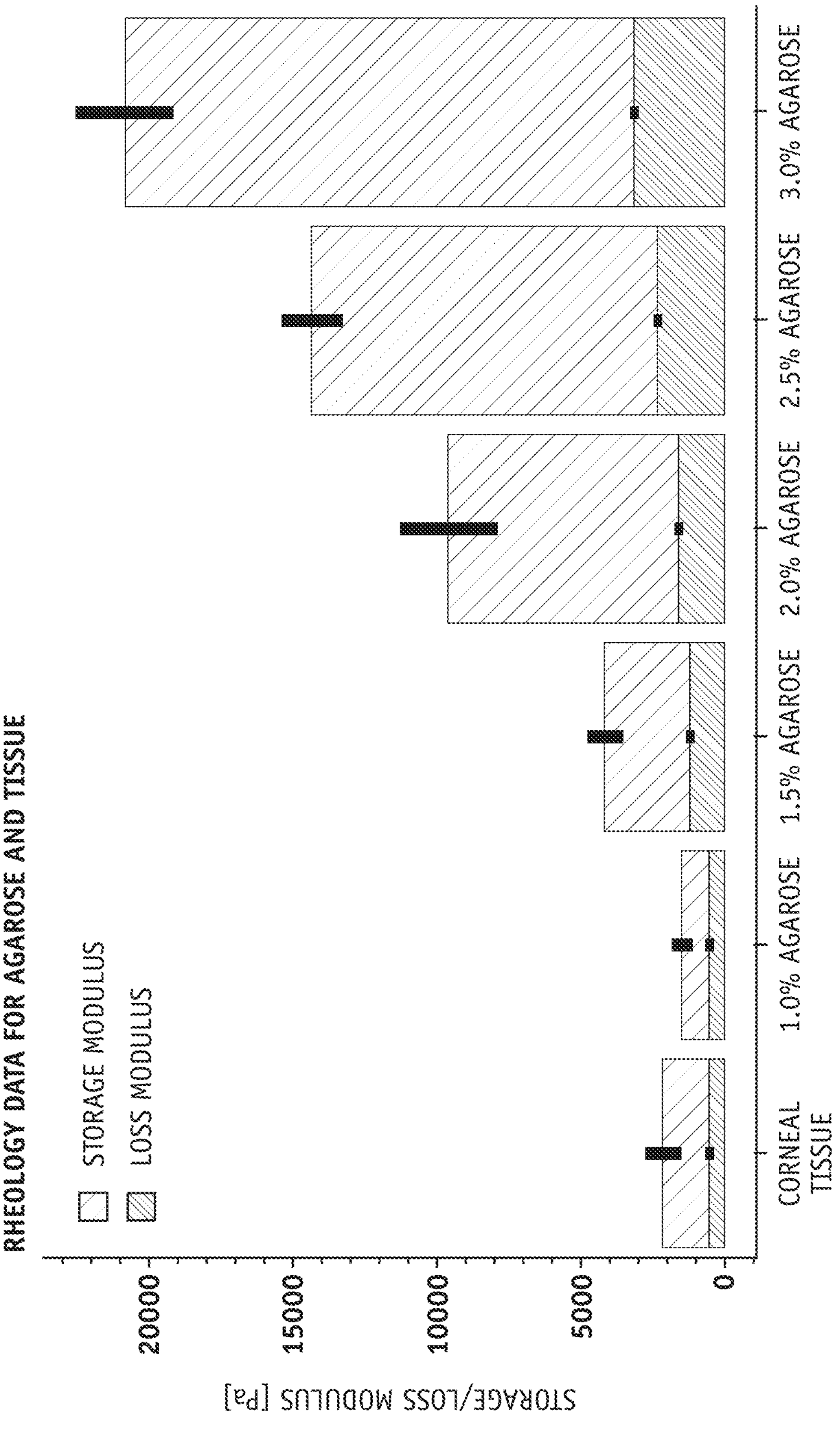
FIG. 14 shows a chart illustrating the rheological data of agarose gels and corneal tissue. Storage and loss modulus taken as the average of reported values when doing frequency sweeps from 1 to 1001/s. N=6 measurements per sample. 95% confidence intervals shown.

The results of this testing are shown in FIG. 14. The storage and loss modulus for 1.0 to 3.0% w/v agarose gels are plotted along with the data measured from corneal tissue. From this data, it can be found that the 1.0% w/v gels are the most similar compared to the corneal tissue. The outcomes of this experiment have to be considered along with the testing parameters. The strain rates measured in this experiment are very low. This is problematic, since it has been demonstrated that the mechanical properties of corneal tissue are heavily dependent on strain-rate [28]. Regardless, this data indicated the use of 1% w/v agarose gels for our initial ballistic testing. Agarose was chosen over ballistic gelatin since agarose can be prepared much more quickly than ballistic gelatin. In later experiments, a switch was made to ballistic gelatin so that regressions fit to empirical data could be used to infer particle impact velocity.

Figure 15:
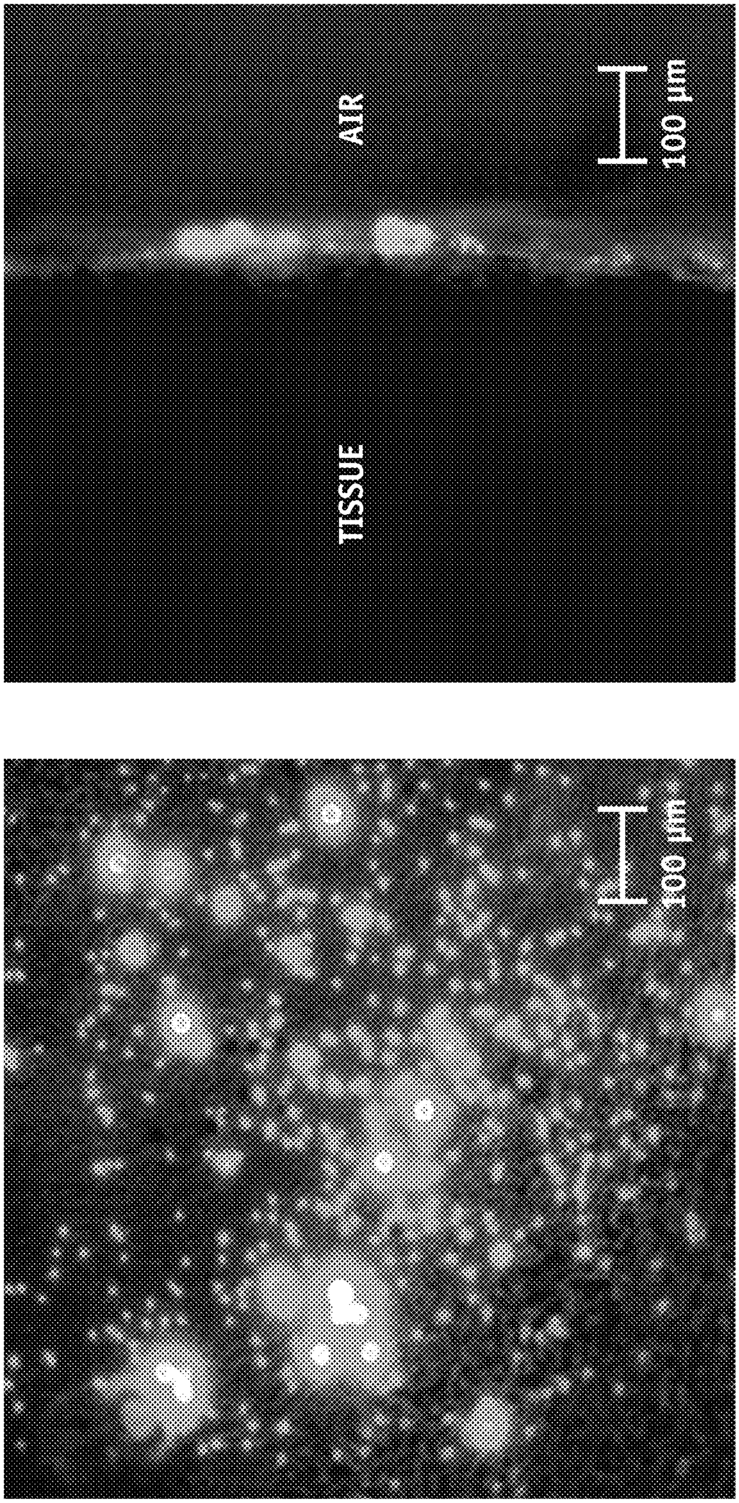
FIG. 15 shows transmission micrographs of corneal tissue treated with 4 and 30 μm poly(styrene) spheres. Top-down view of the cornea shows all microparticles in the same plane (left panel). Cross-section of cornea with particles all on the surface (right panel).

Example 11: Initial Experiments Done with Pneumatic Capillary Gun (PCG) on Corneal Tissue After determining penetration depth statistics in agarose for 10 to 280 μm polystyrene microspheres using the PCG, experiments were done to see if these microspheres would embed in porcine corneal tissue. This testing was done by preparing lure-lock cassettes that contain a solution of 1.5% w/w 30 μm particles with 0.5% w/w 4 μm particles. Each cassette received 2.5 μL of the solution and were dried using the freeze-drying method (Section 2.2.4). 4-μm microparticles were included to mark the surface of the tissue (due to their low impact velocities from fast deceleration rates). Similar solutions were prepared with 10 and 20 μm particles. Once cassettes were prepared, porcine eyes were trimmed of surrounding fat and muscle tunic and their surfaces were dried. Particles were delivered to the anterior surface of the tissue using an acceleration pressure of 4 bar and an injection pressure of 4.5 bar in Alex Groissman's capillary device. To image particles in tissue, transmission microscopy and confocal microscopy were performed to illuminate fluorescent microparticles. Transmission microscopy was performed by dissecting the cornea, placing it on a microscope slide, and tilting it to reveal the cross-section. Transmission microscopy results are shown in FIG. 15 In both the top-down view of the cornea and the view of the cross-section, all microparticles appear on the anterior ocular surface in the same plane. These results indicate that the plastic spheres do not have enough kinetic energy to penetrate the surface of the cornea. FIG. 15 also reveals a dense network of collagen fibrils under the surface of the epithelium. This meshwork leads one to suggest that smaller microparticles may be able to get into the stroma, but these particles do not have enough energy to break through the epithelial layer. In confocal microscopy, all three particle preparations containing 10, 20, and 30 μm particles showed similar results—superficial penetration. These particle samples appeared in the same plane, just barely penetrating the surface from zero to half a diameter.

Figure 16:
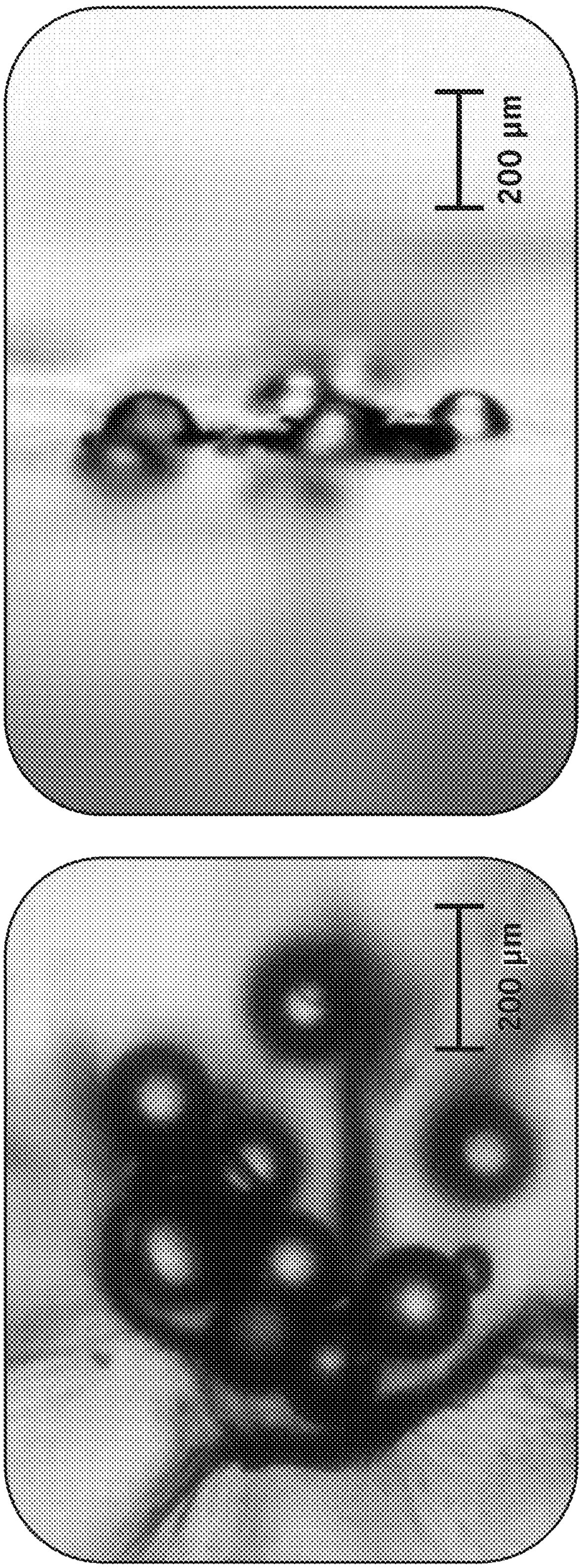
FIG. 16 shows transmission micrographs of corneal tissue treated with 150-180 μm barium titanate spheres (4.2 g/cc), wherein a cluster of particles indents the surface of the cornea instead of penetrating to deeper tissues (left panel) and a group of particles has embedded by about half a diameter (right panel).

To increase the amount of kinetic energy of particles, 150-180 μm barium-titanate microspheres were delivered to the cornea. These beads, which had the ability to penetrate 1% w/v agarose gels by over two millimeters, represented the microparticle with the greatest overall kinetic embedding energy accessible with the PCG (at that time). Despite deep penetration in gel, microparticles were again found to be incapable of penetrating the cornea. Two modes of particle arrest are shown in FIG. 16. Some of the microparticles were "caught" by the cornea, making an indentation on the surface of tissue. Other particles are seen embedding in the surface by as much as half a diameter. Since these particles are over three times the thickness of the epithelium, this penetration does possibly suggest penetration to the stroma. However, penetration with such large spheres in which particles may just be indenting the surface is not the kind of particle penetration sought out for (i.e. indetectable by the eye). When the PDS1000 gene gun became available, it afforded the opportunity to test smaller, denser materials (see Table 2 for reason the ballistic device is less compatible with dense particles).

Example 12: Preparation of Corneal Tissue Samples

To carry out experiments, porcine eyes were acquired within twelve hours of animal sacrifice (Sierra Medical Products) and were used within two hours. The eyes were stored in antibiotic media and kept moist with phosphate buffered saline (PBS) prior to microparticle treatment until ready for particle delivery, when the eyes were trimmed of surrounding tissue and the surface was lightly dried.

Following particle delivery, porcine eyes were placed in Falcon vortex tubes filled with Davidson's Fixative Solution (DFS, as described in Shariati et al., 2008[29]). Whole eyes were allowed to be fixed for two hours so the cornea would maintain its natural shape, and then corneal tissue was dissected from intact globes, placed in DFS, and refrigerated for 24 hours.

Whole eyes were allowed to be fixed for two hours so the cornea would maintain its natural shape, and then corneal tissue was dissected from intact globes, placed in DFS, and refrigerated for 48 hours.

Tissue was transferred from DFS to 10% w/w sucrose in PBS for eight hours followed by 30% w/w sucrose in PBS overnight. Fixed cornea tissue was trimmed to a 1 cm square and frozen in optimal cutting temperature (OCT) compound for 1 hour at −80° C. Sections were prepared on a microtome in a cryostat to a thickness of 50 μm (larger than the largest particle size) and were imaged immediately to collect data on particle positioning within the tissue. Gel samples were sufficiently stable to section manually using a razor blade in order to photograph particle-field cross-sections.

Example 13: Ballistic Delivery of Microparticles

A BioRad PDS-1000 gene gun (catalog #: 1652257) was used to deliver high-velocity microparticles following protocols described in Sanford et al., 2003. In brief, a payload of microparticles of interest is placed on a Kapton disc (macrocarrier) that is mounted below the gas acceleration tube of the device. A rupture disc that bursts at a prescribed pressure (1350 PSI, 92 bar) is mounted in the gas acceleration tube.

The sample chamber is then pumped down to approximately 23 mm Hg to maximize payload acceleration (the sample is exposed to vacuum for approximately 30 s). The gas acceleration tube is pressurized with a desired carrier gas (helium); when the rupture pressure is reached, the gas expands, accelerating the macrocarrier in a reproducible manner. Particles release from the macrocarrier when it is abruptly stopped by a wire mesh that allows microparticles to pass (1 cm flight length).

Five polydisperse microparticle materials were chosen to span the desired density range. The range of tested microparticle composition and density is shown in Table 2.

TABLE 2

Information About Particles Used

| Particle Material | Particle Density | Size (Diameter) Range |
|---|---|---|
| poly (ethylene) | 1.1 g/cc | 10-29 μm |
| soda-lime glass | 2.5 g/cc | 10-22 μm |
| baruim-titanate glass | 4.2 g/cc | 5-22 μm |
| stainless steel | 7.8 g/cc | 5-22 μm |
| tungsten | 19.2 g/cc | 20-40 μm |

According to the manufacturers (Cospheric for all particles except ones made of tungsten which come from US Research Nanomaterials Inc), few particles are smaller than the indicated size range and not more than 10% of microparticles are larger than the indicated size range. This accords with the distribution of sizes measured in subsequent data.

The particles were placed in 96% v/v ethanol at a concentration of 3% w/w and vortexed immediately prior to pipetting 20 μL onto macrocarriers. Note that the experiments are analyzed one particle at a time to relate penetration depth to particle size, so the results are not affected by possible differences between the particle size distribution on the macrocarriers (suspension taken from the bottom of the test tube might be enriched in faster-settling larger particles). Ethanol was allowed to evaporate three hours in a desiccator at ambient temperature and pressure before particles were used.

Particles were delivered to the surface of the cornea prepared according to Example 10, using the Bio-Rad PDS-1000, which delivers particles to tissue under rough vacuum. Embedding has also been achieved by a custom-device that works at atmospheric pressure.

Microparticle penetration was characterized in three gels and three cornea samples for all materials tested according to procedures exemplified in the following examples.

Example 14: Corneal Tissue Processing for Penetration Depth Measurements

Following treatment according to Example 13, the corneal tissue was fixed using a paraformaldehyde solution, and then was sectioned to reveal cross-sections. This method allowed reliable measurement of penetration depths. While the microtome blade possibly moves particles, the reproducible depths observed in the research suggest that this effect was low.

Figure 17:
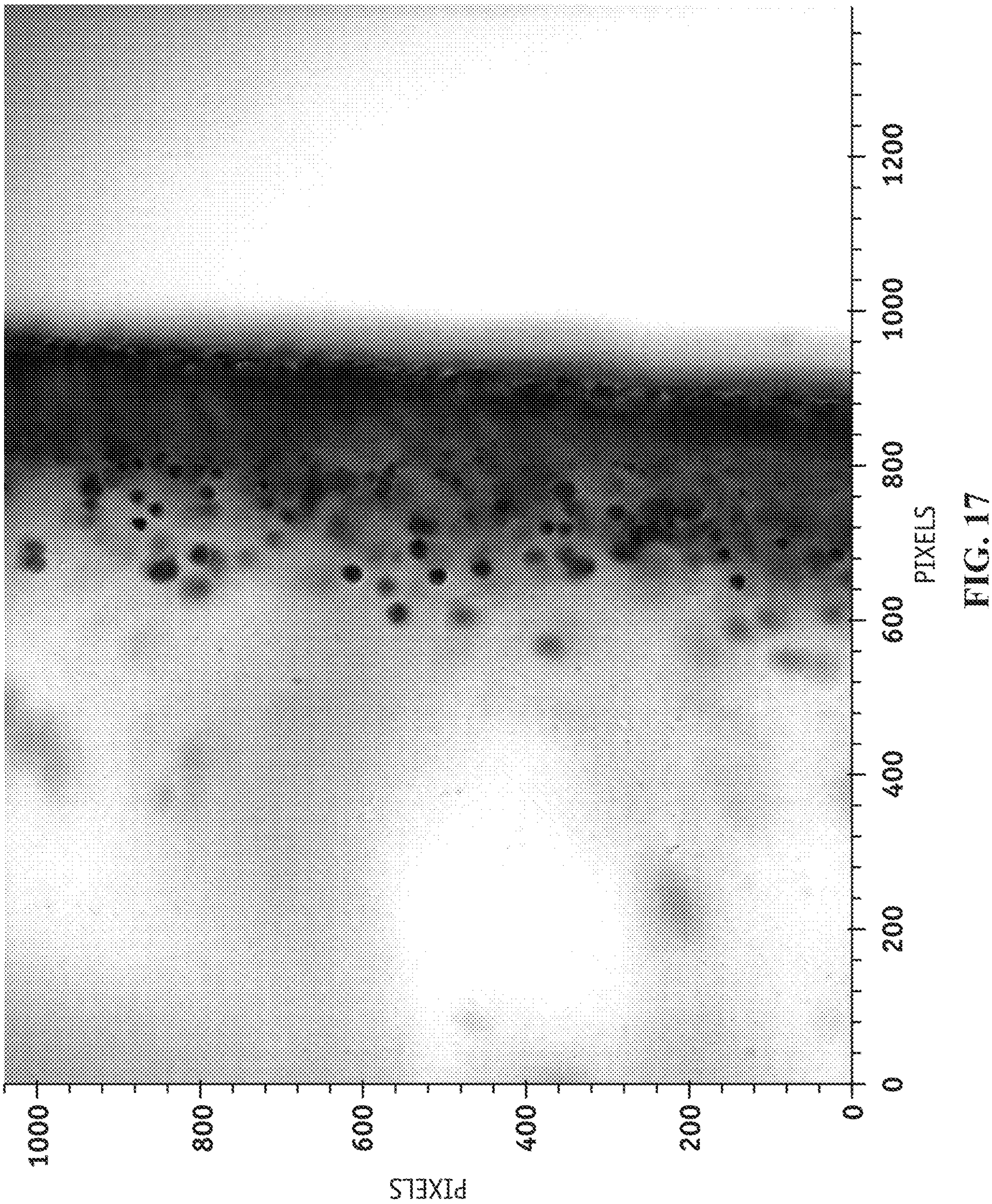
FIG. 17 shows interface used in Jupyter Notebook to click on microparticles in order to record points on each side of the particle as well as points on the surface. These coordinates were fed to the end of the image process pipeline and penetration statistics were generated. Here is shown penetration of stainless steel microspheres in 10% w/w gelatin.

To collect statistics on particle penetration into gelatin or corneal tissue, an image processing pipeline was developed in which individual particles are selected, particle diameter is measured, and the distance from the surface of the specimen is calculated according to Image Processing Pipeline: FIG. 17 shows a representative Image Interface of microparticles delivered to a cornea tissue sample.

Example 15: Ballistic Delivery of Microparticles Comprising Eosin Y to Corneal Tissue Sample The microparticles of Examples 9, were ballistically delivered to the corneal tissue sample prepared according to Example 10, with a procedure exemplified in Example 11. The related depth was measured according to procedures exemplified in Example 12.

In particular, using a vibrating orifice aerosol generator, droplets were generated with a procedure exemplified in Example 8 and 9, using a solution of 3.96% w/w poly (ethylene glycol) (10 kDa) with 0.04% w/w Eosin Yin ethanol.

Specifically, droplets, which were controlled to have diameters of ~100 μm (using a 35 μm pinhole with 15 kHz excitation, 0.35 cc of solution per minute), were fed into a temperature-controlled 1-metertallcolumn heated to 100° C. 30-50 μm particles were collected in a petri-dish and dried by being placed in a vacuum chamber (125 torr) under ambient temperature overnight.

Figure 18:
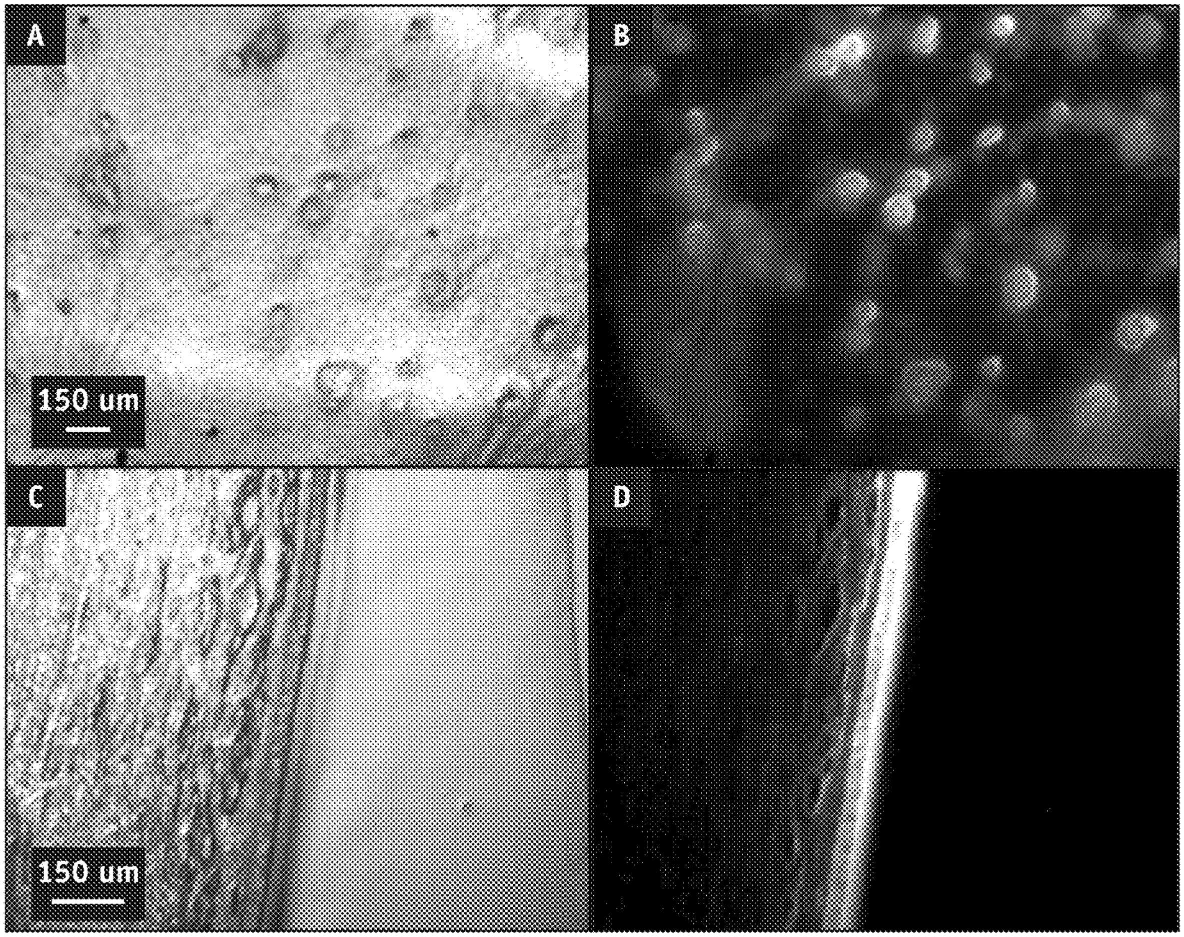
FIG. 18 shows polyethylene glycol microspheres with 1% w/w EY embedded in corneal tissue, wherein in Panel A 10 minutes after particle instillation of anterior surface of the cornea, topdown view of the cornea under brightfield microscopy; in panel B cornea under fluorescent excitation under 500 nm light excitation of Eosin Y 10 minutes after instillation; in panel C two days after instillation, 50 μm thick cross-section of cornea tissue under brightfield microscopy; and in panel D two days after instillation exposed to fluorescent excitation of Eosin Y.

The related results are shown in FIG. 18 Panel A and FIG. 18 Panel B which show particles firmly embedded on the surface of the cornea and beginning to dissolve. FIG. 18 Panel C and FIG. 18 Panel D shows tissue brightly stained with the therapeutic Eosin Y, even after sitting in tissue fixation solution for two days.

A confocal image of the dye fluorescence, like that shown in FIG. 18 Panel B, reveals staining from Eosin Y around microparticles. Following the tissue fixation protocol (two days later), FIG. 18 Panels C and D show the staining of the epithelium with Eosin Y. While more images of the tissue closer to the time of delivery were not acquired, microparticles appear to have fully dissolved while being exposed to fixative solutions. Solid microparticles could not be found and there was a strong staining of the corneal epithelium with the fluorescent Eosin dye. As can be seen in the images, staining of the underlying stroma was minimal. There was some evidence of stromal staining. There is impetus to more closely measure the dissolution of these microparticles.

This support the conclusion that release into the tear film is gradual and may indicate that drug enters adjacent tissues over time. First, particles of size ranging from 5-22 μm diameter with density range from that typical of polymer/drug compositions to that of steel were successfully delivered to corneal epithelium. Second, the corneal epithelium appears to close over the particles after they enter the tissue; we did not see a "track" left by the particles.

Example 16: Ballistic Delivery of Microparticles of Different Size and Densities to the Cornea The microparticles of Example 11, including the microparticles of Table 2, were ballistically delivered to the corneal tissue sample prepared according to Example 10, with a procedure exemplified in Example 11. The related depth was measured according to procedures exemplified in Example 13.

By bombarding tissue with a set of microparticles with a broad range of densities and sizes, information about minimum kinetic embedding energies can be deduced. The following protocol for delivering microparticles to tissue was used. Eyes were mounted and placed in the gene gun chamber as close as possible to the macrocarrier containment assembly. To deliver particles to tissue, 1350 PSI (91.8 bar) rupture discs were used.

The gene gun bombardment chamber was evacuated to ~30 mm Hg absolute pressure. To prepare macrocarriers, the particles were placed in 96% ethanol at a concentration of 3% w/w and were vortexed immediately prior to pipetting 20 μL onto macrocarriers. Particles were allowed to dry for two-four hours before delivery to tissue.

Experiments were analyzed one particle at a time to relate penetration depth to particle size, so the results are not affected by possible difference between the particle size distribution on the macrocarriers (suspension taken from the bottom of the test tube might be enriched in faster-settling larger particles). To quantify the impact response of the cornea to particles, three shots of microparticles were delivered to tissue for each particle density used.

Example 17: Penetration Model of Microspheres in Cornea Tissue

A model of ballistic delivery of microparticles in the cornea has been tested in view of the data of the ballistic deliver of microparticles performed according to Example 14 the Soda-lime, Barium and Stainless steel microparticles of Example 11. The related depth was measured according to procedures exemplified in Example 13 and reported in FIG. 19.

Figure 19:
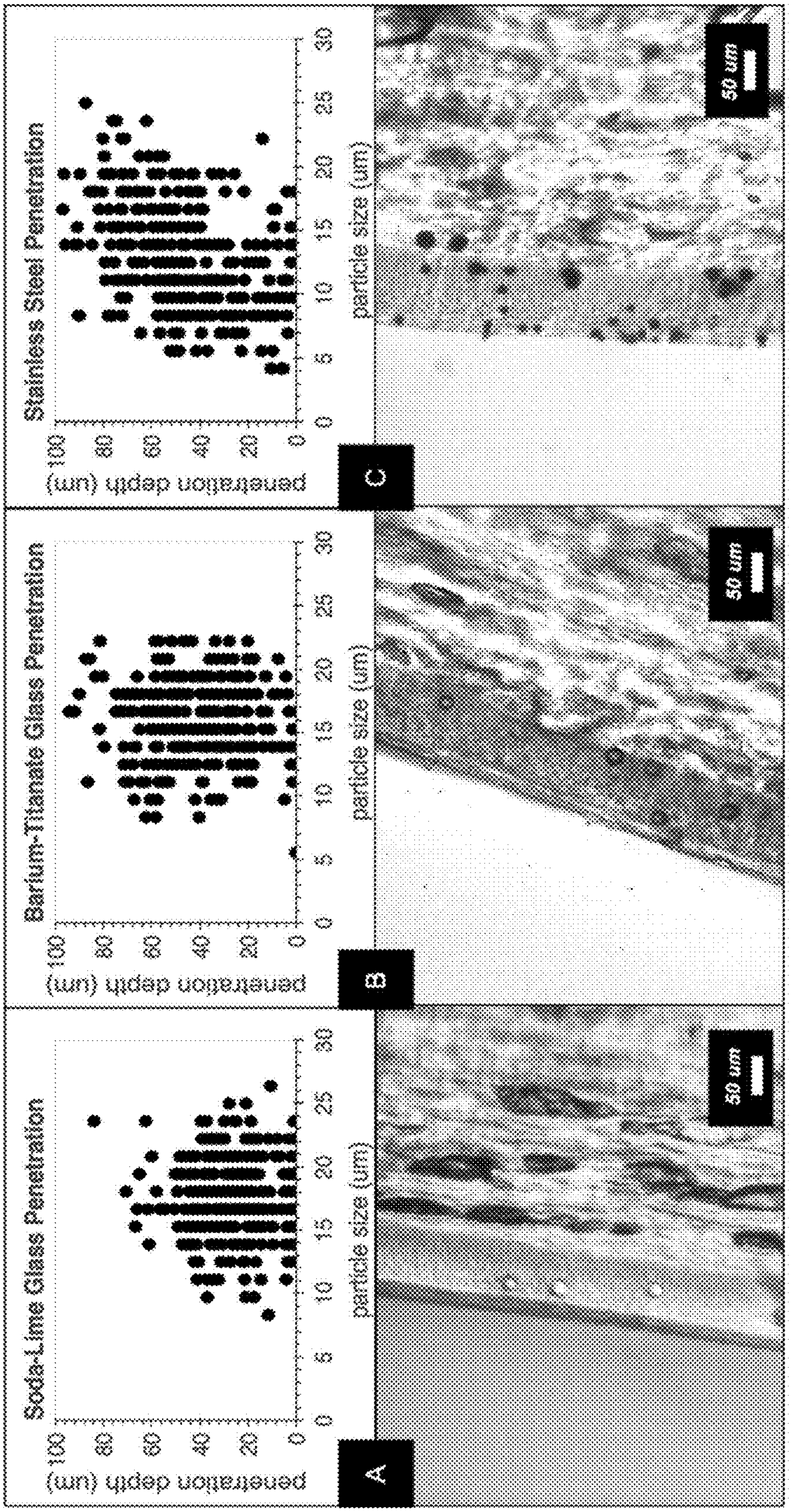
FIG. 19 reports charts and pictures illustrating particle embedding in corneal tissue. Penetration depth of 300 particles from three shots to porcine cornea and representative micrographs for soda-lime glass particles in FIG. 19, Panel A, barium-titanate glass particles in FIG. 19, Panel B, and stainless steel particles in FIG. 19, Panel C.

In particular the statistics shown in FIG. 19 were recorded by processing image data from sections of corneal tissue exposed to ballistic microparticles.

Each scatter plot shows the result of 300 particles identified in tissue. The particles were identified and their dimensions indicated by a user of the image processing pipeline. This was done instead of thresholding image intensity data because there were defects in the image data that came from reflections off of the tissue which made it difficult to identify objects from thresholding alone. There are slight variations in the thickness of the epithelium. The thickness of the epithelium was measured for 100 images of corneal sections. The average thickness was 63.1 μm (standard deviation of 9.8 μm). Despite areas where the epithelium was thinner, there is little ability for the microparticles tested to carry through the epithelium and embed into the stromal tissue of the cornea.

As shown in the illustration of FIG. 19, all three particle compositions penetrate the cornea the extent of penetration is shown to depend on density more than on size.

In particular, as shown in FIG. 19 both small and large particles embed to similar depths in the corneal epithelium, and most particles can be found between 30 and 60 μm deep (see in particular However, while, the lowest-density microspheres (1.1 g/cc poly(ethylene); PE) did not penetrate the cornea deeply (see FIG. 19 panel A), the particle with higher density tended to accumulate towards the basal layer of the epithelium (see FIG. 19 panels B and C)

Both lower density and high density layer however were able to firmly embed in the apical layer of the cornea as shown by the illustration of FIG. 19 panels A-C.

Example 18: Penetration Model of Microspheres in Cornea Tissue by Probability Density Additional information concerning the behaviour of microparticle ballistically delivered in cornea the related probability density of particle was determined To calculate probability density, impact statistics are binned according to their distance from the sample surface. Then, binned penetration depths are divided by the total number of observations for that particle size. Penetration depth is normalized by dividing the penetration distance by particle diameter, so the expected proportionality to particle diameter yields a constant normalized penetration depth.

Figure 20:
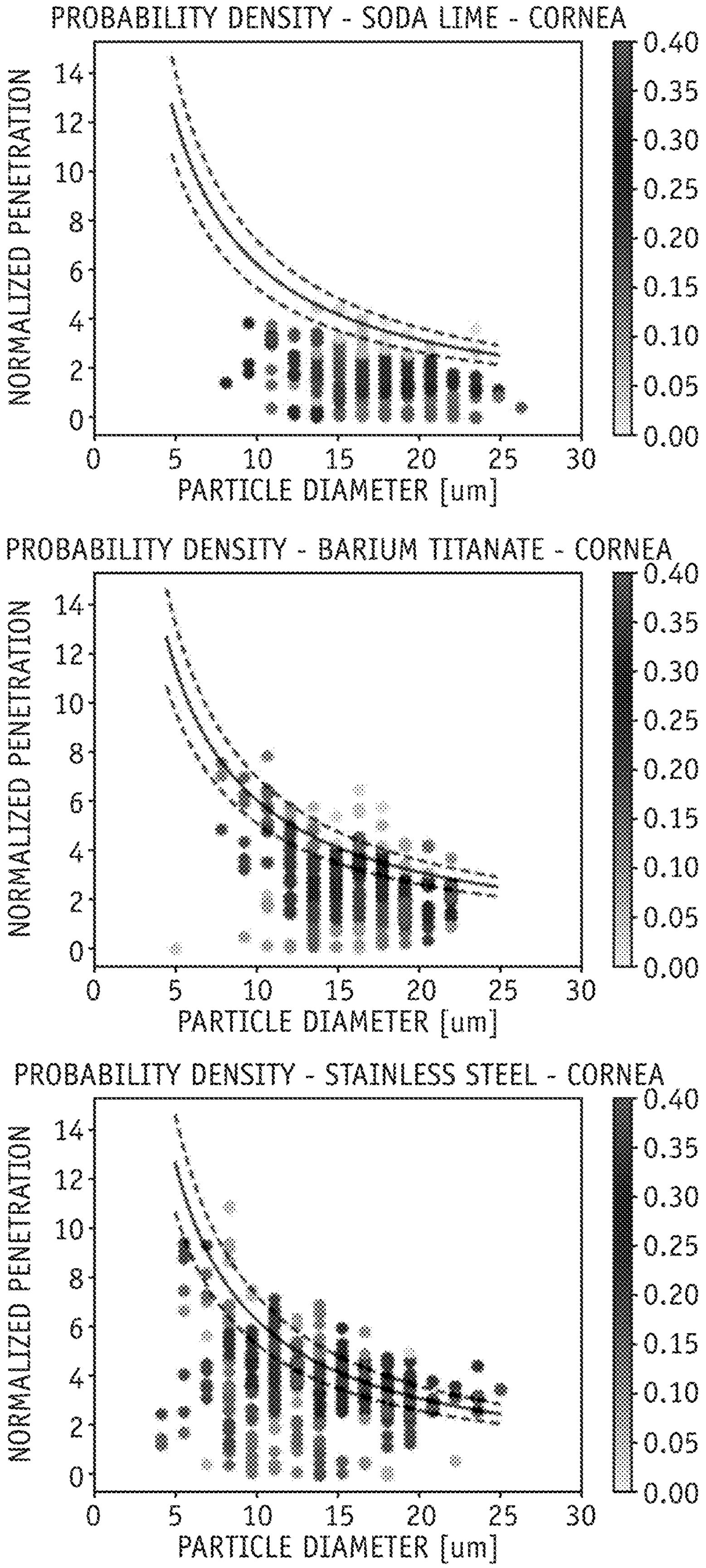
FIG. 20 shows probability densities of soda lime, barium titanate, and stainless steel impacts in corneal tissue shown with particle penetration normalized by particle diameter. The curve band represents the measured average thickness of the epithelial layer bounded by a standard deviation above and below the mean value.
Figure 21:
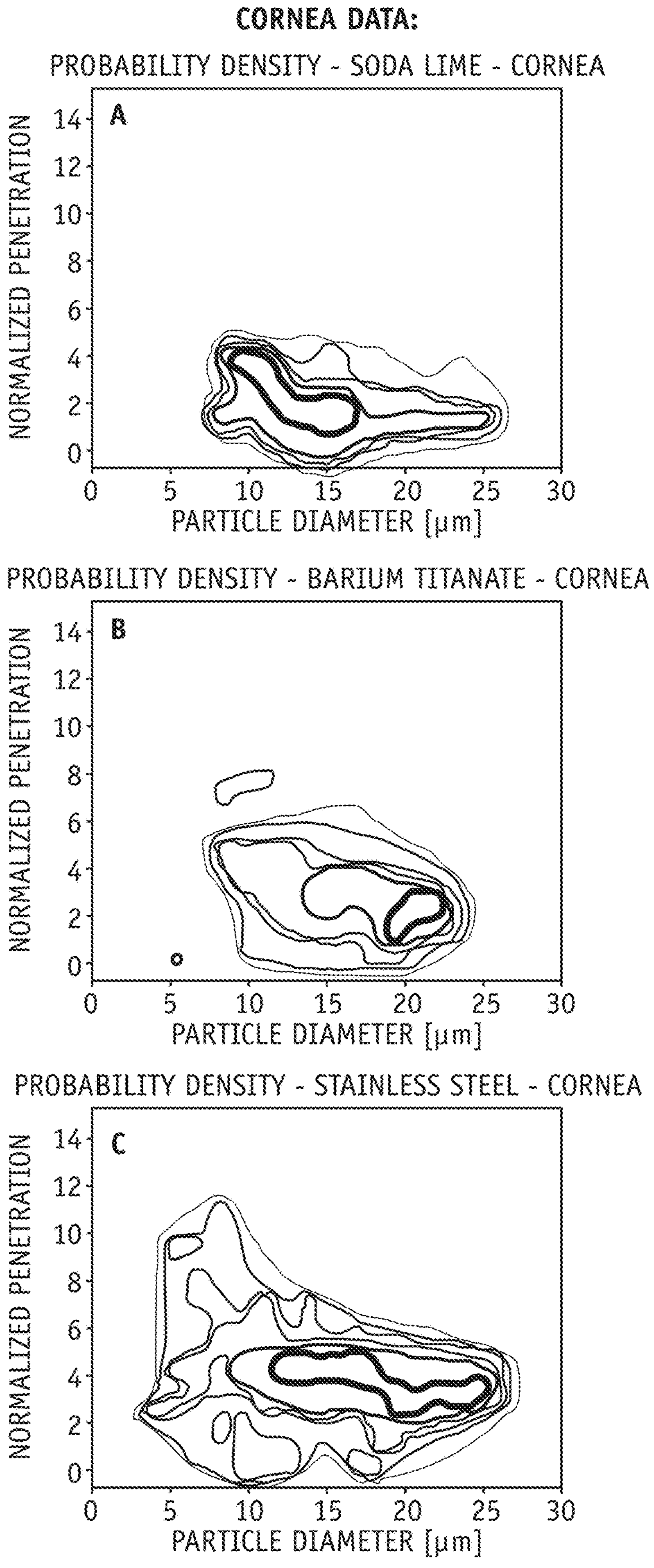
FIG. 21 shows the same penetration depth data as in FIG. 20 in a contour format.
Figure 22:
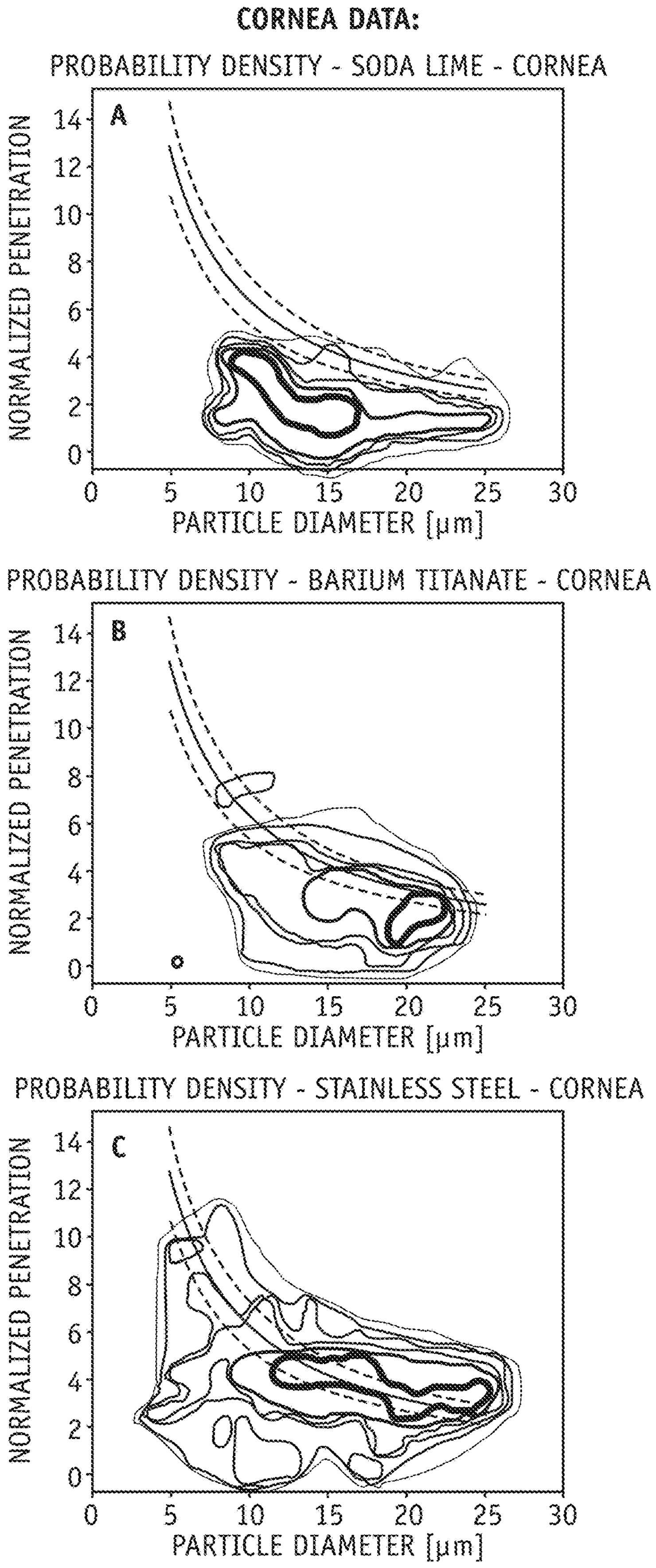
FIG. 22 shows the same penetration depth data as in FIG. 20 in a contour format with average thickness of the epithelial layer bounded by a standard deviation.

The results are shown illustration of FIGS. 20, 21 and 22. In FIG. 20, the "hotter colors" (darker) represent areas where the probability density was greatest. FIG. 21 shows the same penetration depth data of FIG. 20 in a contour format. FIG. 22 shows the same penetration depth data as in FIG. 20 in a contour format with average thickness of the epithelial layer bounded by a standard deviation.

The probability density for the normalized penetration depth in ballistic gelatin is insensitive to particle size, as expected (FIG. 20 Panels A-C). In gelatin, increasing relative density of the particles relative to the sample conforms with the expected proportional increase in normalized penetration. In contrast, normalized penetration into the cornea is not independent of particle size and does not simply increase proportionally with the particles' relative density (FIGS. 20A-C).

In FIG. 20, the curved bands represent the expected location of the interface between the epithelium and the stroma. When the average thickness of the epithelium is divided by the diameter of an expected particle, the solid curve is generated. The dotted lines indicate upper and lower bounds of the epithelium interface calculated by using the standard deviation statistics recorded measuring the thickness of the epithelium.

Peculiar features of the distribution of normalized penetration in the cornea include possible evidence of bimodal probability distributions for small, low density particles (FIG. 20 Panel A), 12.5±0.7 and 14.0±0.7; for smaller particles, very few entered the epithelium and loss of particles from the surface during handling precluded quantitation). A first peak at very low penetration suggests that there is a threshold impact velocity required to pass through the apical layer of the corneal epithelium (i.e., the distribution of impact parameter for small soda lime particles includes some that are so low that the particles come to rest on the epithelium). With increasing size, soda lime particles transition to a unimodal distribution as seen in ballistic gelatin, with the most probable normalized penetration that is insensitive to particle size (FIG. 20 Panel A, for particle diameter>15 μm).

At the opposite extreme, large, high density particles show a penetration depth that does not increase with particle size and normalized penetration depth actually decreases with increasing particle size (FIG. 20 Panel B for particle diameter>15 μm and FIG. 20 Panel C for particle diameter>8 μm). This behavior is not described by either the Poncelet model or the elastic Froude number scaling rule. The ability to deposit particles to a narrow region relative to the distribution of size and velocity of the particles is clinically useful. It enables clinicians to deliver a biologically active cargo to a controlled depth reproducibly despite variations in the particle size and velocity.

The peak penetration depth appears to be dictated by the thickness of the epithelium (indicated by a shaded band in FIG. 20 Panel A) The limited ability of the microparticles tested to penetrate through the epithelium and embed into the stromal tissue of the cornea suggests that there is a threshold remaining kinetic energy that must be exceeded for particles to pass through the boundary between the epithelium-stroma. In accord with this hypothesis, the distribution of penetration depths has a pronounced asymmetry, with an abrupt decrease in probability of penetration into the stroma.

As a results of the probability density determination exemplified in FIG. 20, FIG. 21 and FIG. 22 it appears that when particles enter the cornea, there is a narrow range of penetration depths in which particles with having the tested diameter and densities can embed, confined to the epithelium and the bowman's layer if present for the range of impact parameter examined here.

Once particles reach the epithelial-stromal boundary, their motion is essentially arrested. Although previously unanticipated, this behaviour can be rationalized in hindsight based on corneal mechanical properties in the literature. Atomic force microscopy (AFM, using for example, SiN cantilevers with a borosilicate sphere tip) has been applied to interrogate individual layers, leading to a Young's Modulus of 0.57 kPa for the corneal epithelium, 110 kPa for Bowman's Layer, and 33 kPa for the stroma (Last et al.; 2010 [21]). However, the large contrast in properties reported by Last et al is not found in other studies, such as [23] which reports elastic modulus of the rabbit corneal epithelium, 0.57±0.29 kPa (mean±SD); anterior basement membrane (ABM), 4.5±1.2 kPa; anterior stroma, anterior stroma, 1.1±0.6 kPa (note the 30 fold lower value than Last et al.)

While porcine corneas lack Bowman's Layer, mechanical properties within the stroma can be stiff and vary with depth. Regions where the collagen lamellae are more interwoven (the anterior stroma) are consistently found to be stiffer than the posterior cornea (Blackburn et al., 2019[19]). Such a step up in the stiffness could explain the high probability of particles halting at the boundary between the two layers.

The experimental discovery that particles observed to penetrate to the same depth in ballistic gelatin form a group with respect to their ability to penetrate the cornea provides guidance regarding other combinations of density and velocity that will also deliver particles of diameter from 20 to 30 μm to the posterior half of the epithelium: in addition to particles having dimension 20-30 μm and density of 7.8 g/cc with velocities from 140 to 180 m/s, delivery to the posterior half of epithelium can be achieved using particles having dimension 20-30 μm and a density of 4.2 g/cc by using velocities from 270 to 330 m/s.

Although it would require supersonic velocities, as can be provided by LIPIT, particles having dimension 20-30 μm and a density of 2.5 g/cc can also be delivered to the posterior half of the epithelium by using velocities from 450 to 550 m/s. The penetrating power varies smoothly with velocity and density, such that interpolation between the experimentally observed ranges reliably identifies other combinations of density and velocity that will provide localization of delivery to the posterior half of the epithelium for a selected particle size. This is useful when considerations of a particular formulation of biologically active cargo and carrier places a restriction on the density that can be used. For example, particles of density 3.35 g/cc (midpoint between 4.3 and 7.8 g/cc) having velocity from 360 to 440 m/s.

This conclusion is unexpected as the possible role of the epithelial basement membrane and concluded that for the porcine corneas considered here before the experiments herein summarized was considered unlikely to make a significant contribution to arresting particle penetration: it is quite thin (~100 nm thick) and is continuous with the stroma below (Abhari et al.; 2018[30]).

Nonetheless, the evidence reported in this present disclosure suggests layered heterogeneity in mechanical properties of tissue is what gives rise to the cornea's penetration response.

Example 19: Penetration of Low Density (Less than 2.5 g/cc) Microparticles in Corneal Tissue Lowest-density microspheres (1.1 g/cc poly(ethylene); PE of Example 11 and Table 2 above) did not penetrate the cornea deeply, but they were able to firmly embed in the apical layer of the cornea.

Figure 23:
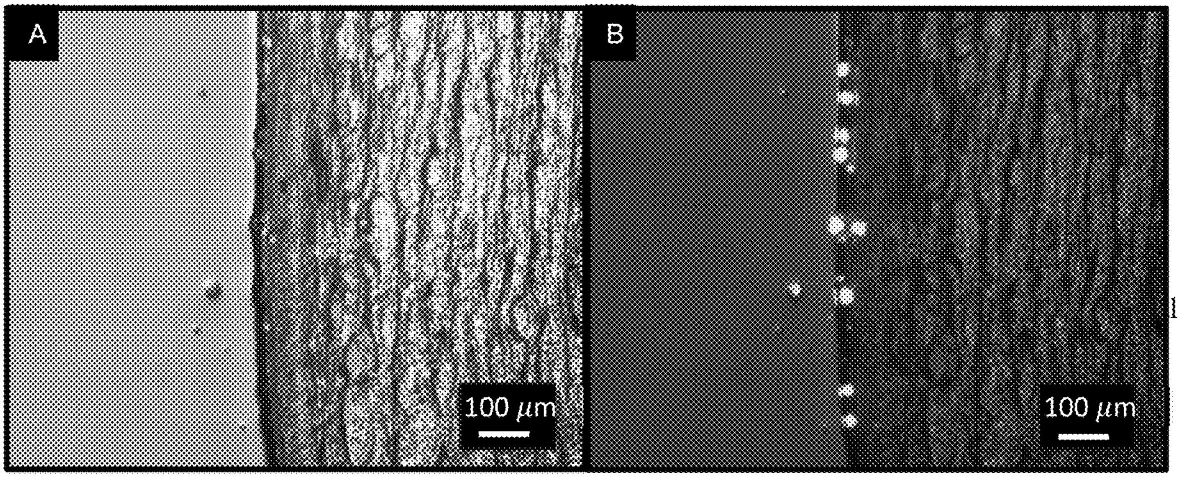
FIG. 23 shows superficial penetration of low-density microspheres in corneal tissue. Poly(ethylene) spheres, which show low penetration in ballistic gelatin, barely penetrate corneal tissue. Fluorescent micrograph shown on the right to highlight microparticles.

When corneal tissue was tested with these particle payloads, penetration was superficial. FIG. 23 Panels A and B show fluorescent microparticles embedded just at the surface of tissue. While penetration was far from reaching stromal tissue, it is promising that particles can be found on tissue after three days of the tissue processing protocol.

These results suggest that microparticles are firmly embedded on the surface of the tissue. In addition, since the densest layer of tight protein-junctions are on the anterior surface of the cornea between stratified epithelial cells, this type of penetration may still enhance drug delivery.

Figure 24:
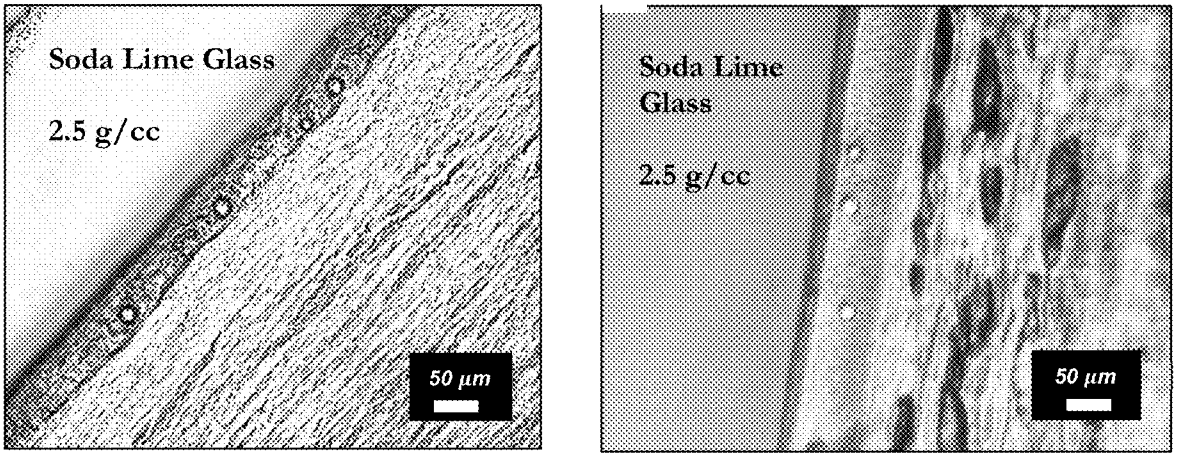
FIG. 24, reports pictures showing Soda-Lime glass spheres embedded in section of corneal tissue. Tissue sections are 50 μm thick. Particles embed throughout the epithelium.
Figure 25:
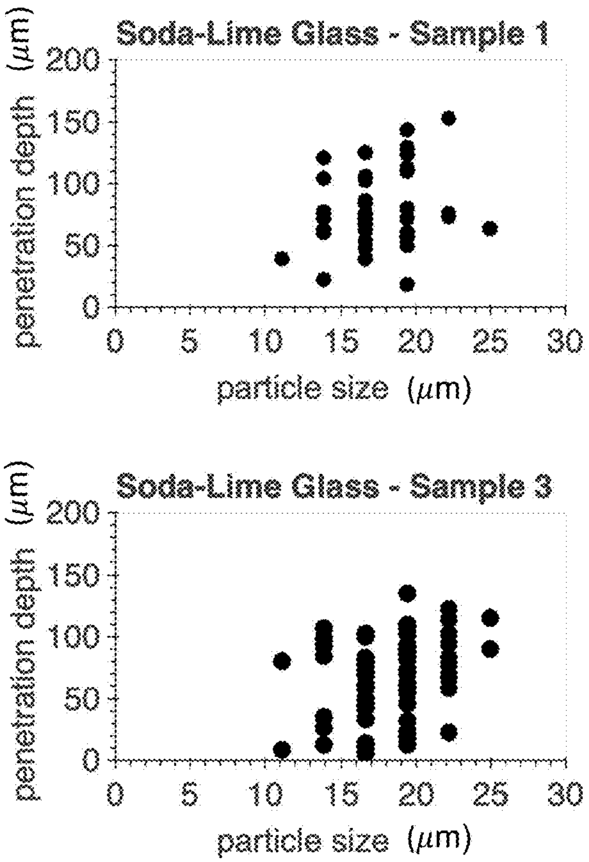
FIG. 25 shows charts illustrating Penetration statistics of soda-lime spheres embedded in corneal tissue. The penetration of spheres in tissue is shown for three separate shots into three different corneal samples. Image processing pipeline was used to go through each image individually.

Example 20: Resulting Penetration of 2.5 to 7.8 Glee Microparticles in Corneal Tissue The next particles that were tested were soda lime glass spheres (10-22 μm; 2.5 g/cc). These particles showed significant penetration through the corneal epithelium, and they did not penetrate any further. The penetration observed from representative micrographs shown in FIG. 24 indicates particles scattered throughout the epithelium. Penetration statistics for all three cornea samples treated with microparticles, shown in FIG. 25, indicate similar penetration statistics from one particle delivery to another. Sample one shows only 80 particles found in the tissue (as opposed to 100 for all other samples and materials). More images were taken of the third sample to compensate. The range of particles detected by the image processing pipeline is representative of the actual range of particles reported by the vendor. Some particles are slightly larger than the expected size range, potentially due to clicking on larger diameters than actually were seen using the image processing pipeline. It is possible that deceleration of smaller particles led to a pileup at the surface of the tissue. There was a smaller quantity of particles found in the tissue sections than was seen testing higher density microspheres. It is possible that particles are embedding in the apical surface of the cornea and tissue processing is stripping particles from the surface, reducing the number of particles seen in sections. This low number of particles observation was seen with PE spheres as well.

Figure 26:
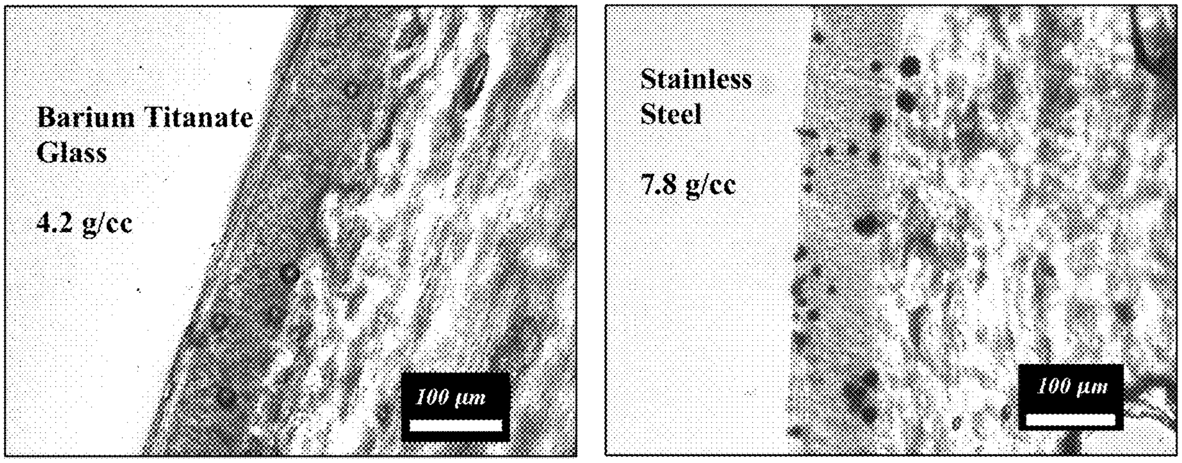
FIG. 26 reports pictures showing penetration of barium-titanate and stainless-steel microparticles in cornea. The penetration of spheres in tissue is shown in 50 μm tissue sections.
Figure 27:
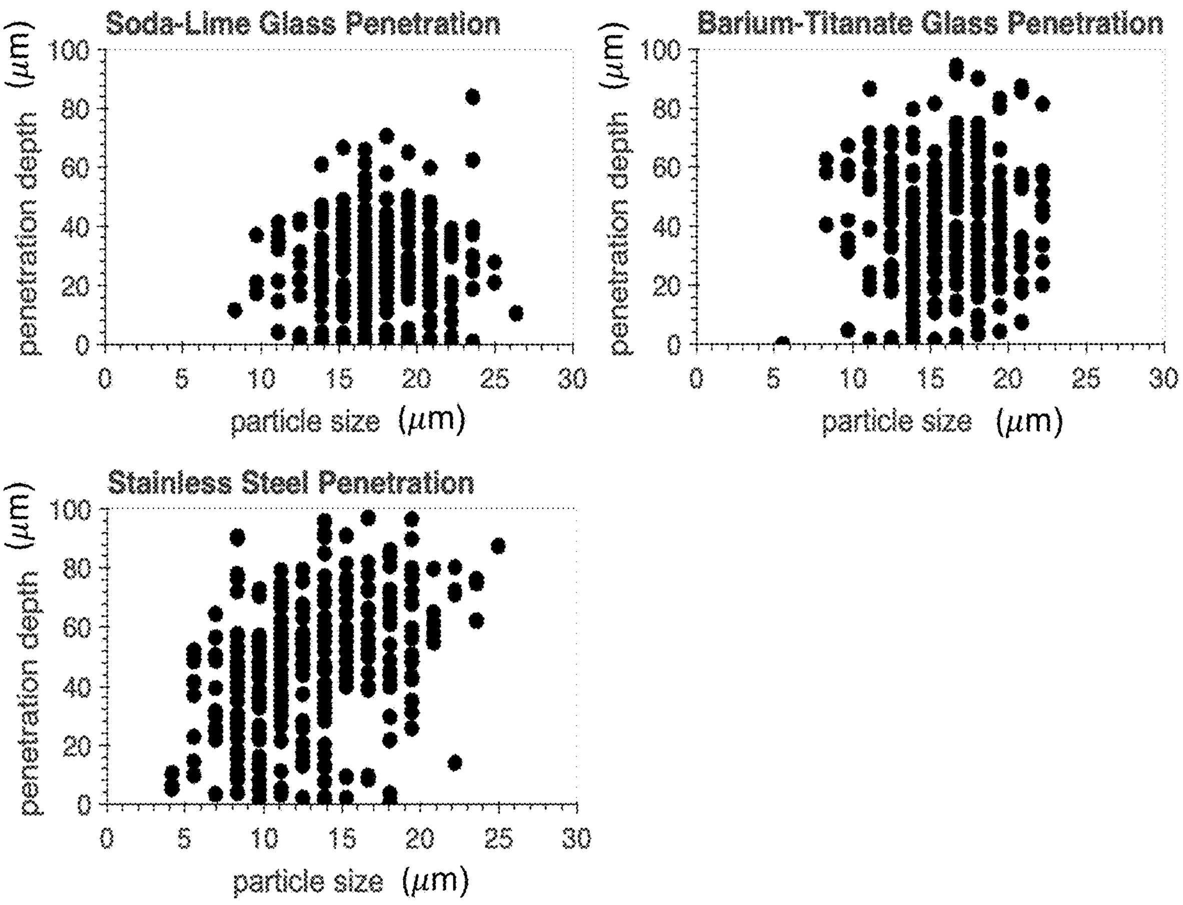
FIG. 27 shows charts reporting penetration statistics for range of particle densities in cornea. The penetration of spheres in tissue is shown for three separate shots of soda-lime glass, barium-titanate glass, and stainless-steel microspheres. Changing particle density only slightly changes particle penetration depth.

When particle density was increased, penetration depth in tissue did not significantly rise, as was expected. Barium-titanate spheres penetrated to the bottom of the corneal epithelium but did not travel any deeper than this. While these particles were able to travel over twice the distance as soda-lime glass spheres in gelatin, FIG. 26 shows the particles getting stuck at the interface between the epithelial layer and stroma. What's more, stainless steel microparticles, which embedded in gelatin up to four times as much as soda-lime glass microparticles, get held back by the same interface. The full penetration statistics of the particles tested, shown in FIG. 27, indicate a slight increase in penetration depth when projectile density is increased, but the penetration is similar for the three sets of particles.

Figure 28:
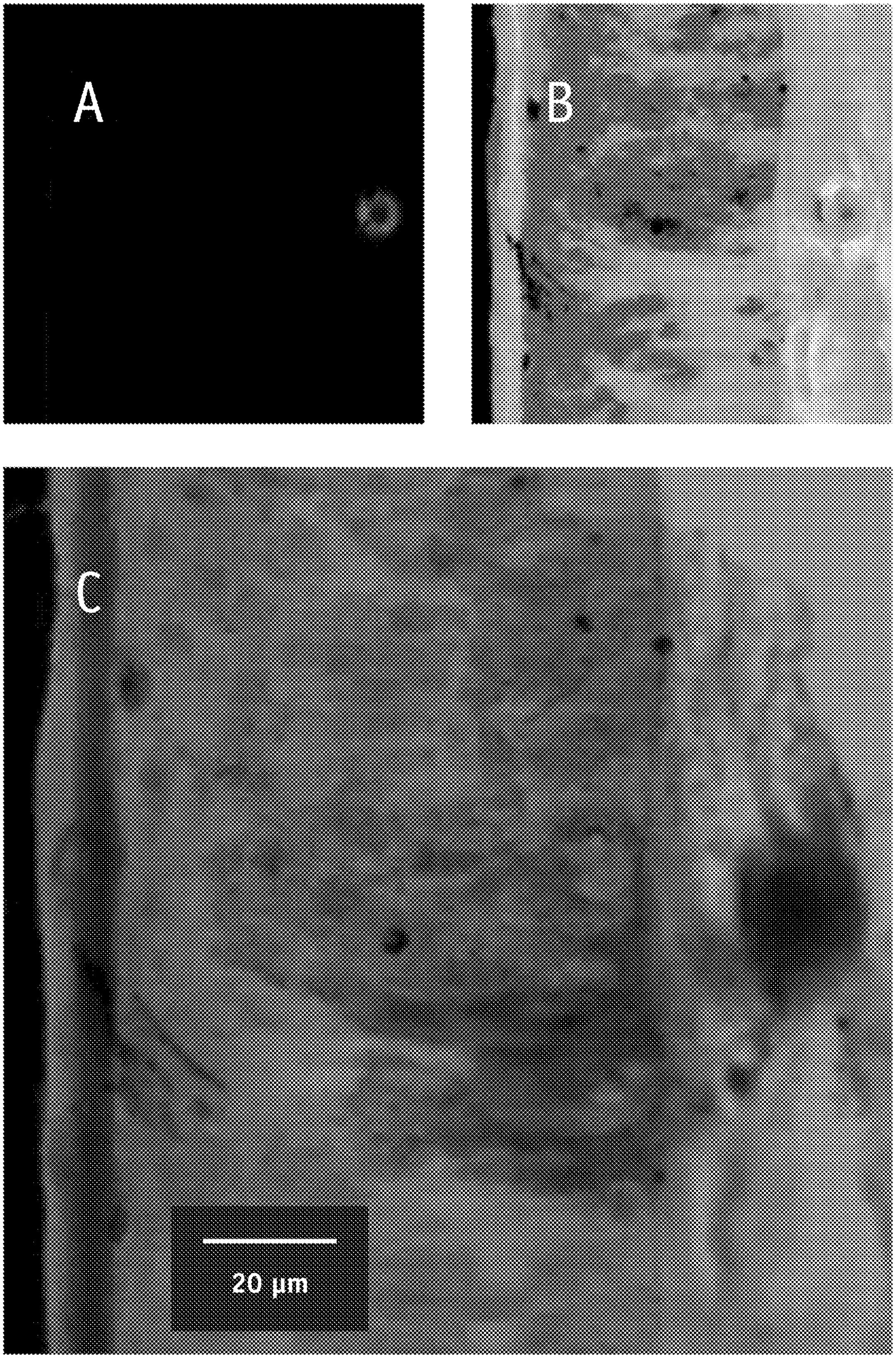
FIG. 28 shows confocal Z-Stack illustrating steel particle embedded in Picosirius-Red stained corneal tissue. From A to C, depth in the z-stack is increased. The 30 μm thick section was stained for 5 minutes in Picosirius Red.

While embedding depth was shallow, it is interesting to note that penetration into the epithelium did not leave a visible "track." To the extent observable with optical microscopy, no evidence of tissue damage was seen. Confocal microscopy was done on tissue treated with stainless steel microparticles prior to staining with picosirius red (Abcam Inc.). Picosirius red is a fluorescent dye that binds strongly to collagen fibrils and is used to determine collagen type, as in Vogel et al.[7] While it was recommended that staining should be done for 1 hour, sections of tissue were stained for 5 minutes. This was sufficient to produce bright fluorescence on the stroma and the epithelium. The tissue was sectioned 30 μm thick to ensure adherence to the microscope slip during staining. When this was done, there were no observed defects in the epithelium that could have been a trail, despite there being many particles that were in the tissue (FIG. 28).

There are slight variations in the thickness of the epithelium. The thickness of the epithelium was measured for 100 images of tissue sections. The mean thickness was 63.1 μm (standard dev. 9.8 μm). Despite areas where the epithelium was thinner, there is little ability for the microparticles tested to carry through the epithelium and embed into the stromal tissue of the cornea.

Figure 29:
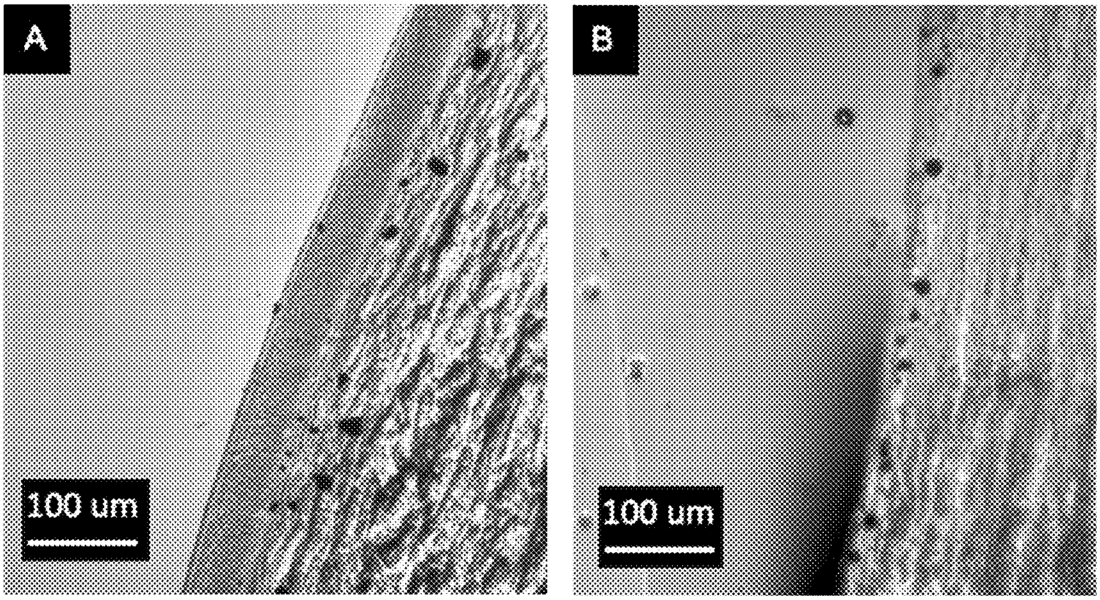
FIG. 29 shows pictures illustrating in panel A tungsten microparticles embedded to shallow depth in stroma and in panel B stainless steel microparticles in tissue with epithelium debrided prior to bombardment.

Example 21: Penetration of Particles Having Density 7.8 g/Cc to 20 g/Cc and Debrided Corneal Tissue A density was established at which microparticles infiltrate the stroma when tungsten was used as a projectile material. FIG. 29 Panel A \shows the results of bombarding intact corneal tissue with tungsten particles. As can be seen, the tungsten microparticles just enter the superficial layers of stromal tissue. Despite having a density twice that of stainless-steel particles tested, there is only a small increase in the total penetration depth of microparticles. FIG. 29 Panel B shows the results of bombarding corneal tissue that has been debrided (epithelium removed with a razor blade). As can be seen, the stroma is an effective momentum sink that arrests particles on its surface.

Figure 30:
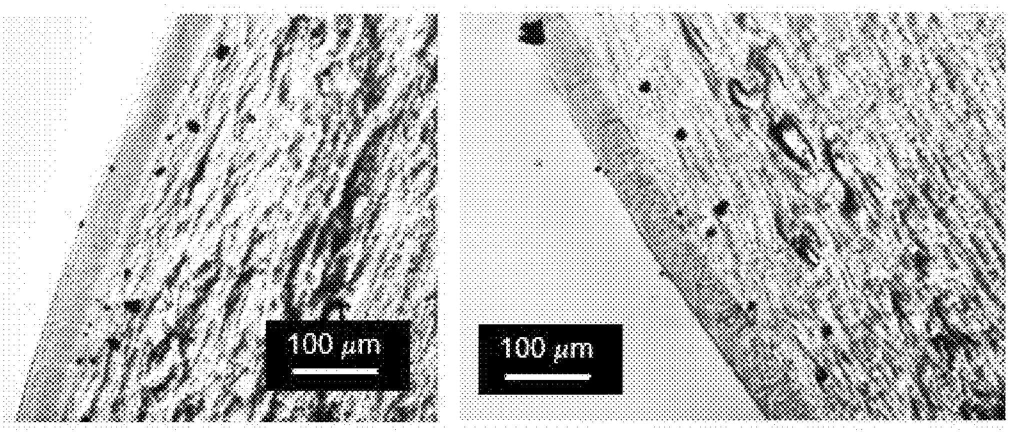
FIG. 30 shows 20 to 40 μm tungsten ballistics embedded in corneal tissue, wherein microparticles of tungsten ballistics, which have 19.2 times the density of the tissue itself, are able to get all the way through the epithelium.

Example 22: Penetration of Particles Having Density 20 g/Cc to 40 g/Cc in the Cornea As a test to determine minimum kinetic energy needed to break through to the stroma, penetration of tungsten microparticles with a diameter of 20 to 40 μm was investigated. Since these particles had such a high settling velocity, it was difficult to pipette mixtures of ethanol and tungsten particles. As such, tungsten was deposited dry on Kapton macrocarriers. Electrostatic forces between particles and the polymer film were enough to keep the particles in place long enough to be bombarded into tissue. The results of bombardments in corneal tissue using an 1800 PSI rupture disc were recorded. Tungsten particles embedded between 50 and 100 μm into the stroma in the two images are shown in FIG. 30. As is shown, tungsten particles are firmly embedded in the tissue, with little damage or disturbance of the surrounding tissue. This data shows that in order for microparticles to traverse the epithelial layer of the cornea, they need to have exceptionally high density like tungsten.

Example 23: Penetration of Microparticles in Anterior and Posterior Layers of Stromal Tissue Tough mechanical properties of the stroma appear to be the cause of particles getting effectively stopped in corneal tissue. This would explain how small particles are able to travel freely more self-diameters in distance before getting halted at the stroma, but larger particles are halted as soon as they reach the epithelium-stroma interface. To test if the stroma was the main source of resistance to microparticle entry, corneal tissue was prepared for ballistics testing that had been debrided (epithelium removed). If particles were indeed being stopped by the thick anterior layers of the stroma, the spheres should still become arrested at superficial depth. If there is a decelerating effect of the corneal epithelium, then microparticles should travel even further without the layer of tissue intact.

Figure 31:
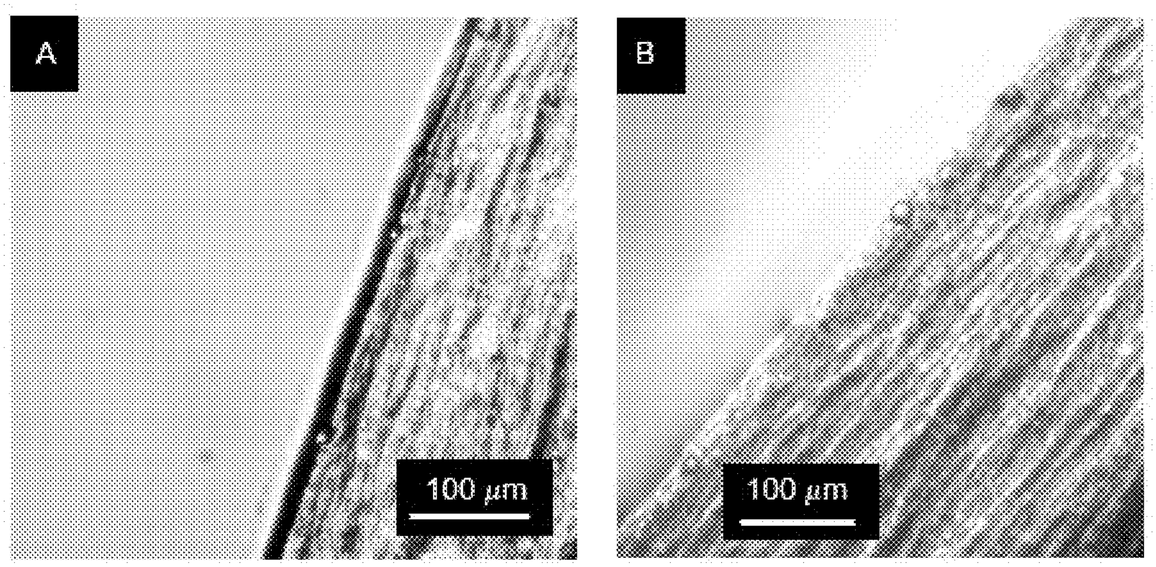
FIG. 31 shows 10-22 μm soda lime spheres embedded in debrided corneal tissue wherein microparticles are embedded in the outermost layer of the stroma and fewer particles are found than with epithelium intact.
Figure 32:
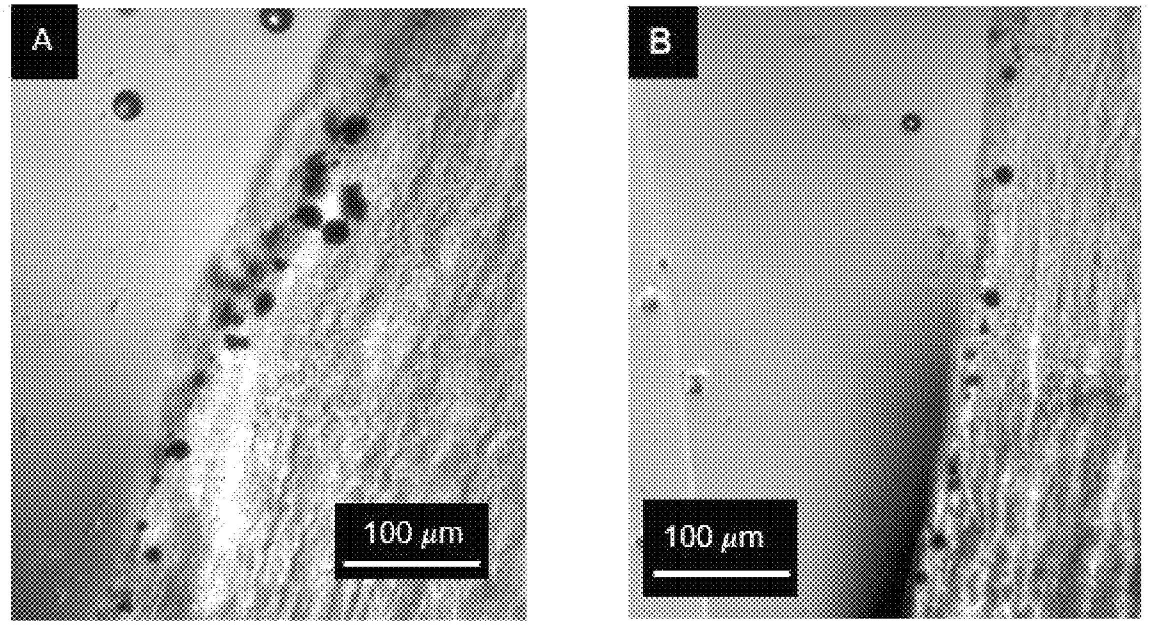
FIG. 32 shows 5-22 μm stainless steel spheres embedded in debrided corneal tissue wherein microparticles are embedded in the outermost layer of the stroma. Particles on the large and small end of the size spectrum show up in the tissue.

The corneal epithelium can be removed by scraping the surface of the cornea with a razor blade. This was done before two preparations of particles were delivered ballistically with the PDS1000 gene gun. Soda-lime and stainless steel microparticles were prepared for the experiment. The results of soda-lime glass spheres embedding in debrided tissue show what was expected: the particles (FIG. 31 are arrested in the outermost layer of the stroma. It was also observed that fewer particles were in the cornea following the tissue processing procedures, as opposed to when the corneal epithelium is in place when particles are embedded. Perhaps this soft layer of tissue keeps particles in the sample while tissue is being fixed and protected. Only the particles that get firmly stuck in the fibers of the stroma remain when the tissue is inspected. Even when the particles are three times as dense as the stainless-steel microspheres are, FIG. 32 shows that microparticles are arrested in the anterior stromal surface. There are fewer microparticles embedded in the tissue than with the epithelium intact, but there are more present than with the soda-lime glass particles. It can be seen that both stainless steel microparticle sizes on the low and high end of the size spectrum show up in the images selected.

Figure 33:
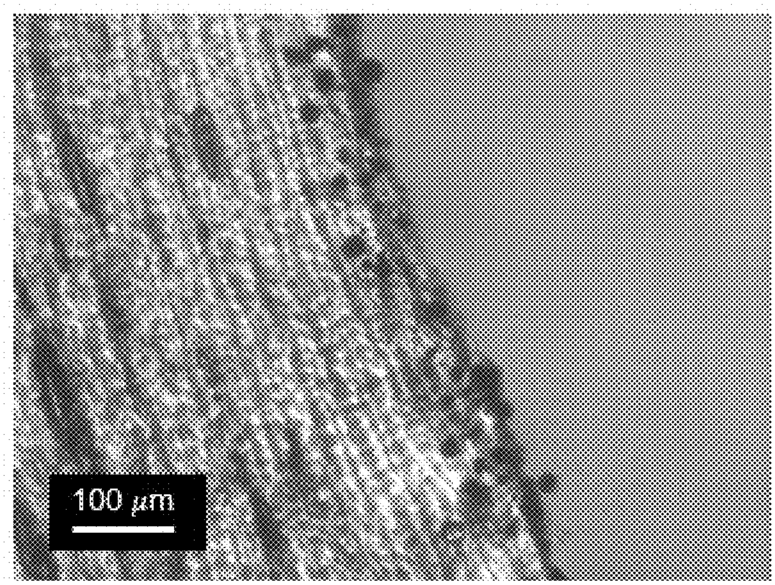
FIG. 33 shows 5-22 μm stainless steel spheres embedded in posterior corneal surface wherein microparticles are embedded in the endothelium and a small distance into the underlying stroma tissue.

In addition to delivering microparticles to the anterior surface of the stroma, particles were also delivered to the posterior surface to assess the ability of the interface to arrest particles (FIG. 33). This was done by dissecting cornea tissue from porcine eyes and using the ballistic device to treat the back surface of each sample. The endothelium is a five micron thick monolayer of cells with hexagonal packing.[12] Since it has such a low thickness, this layer's contribution to the mechanical properties relating to microparticle entry are likely small (compared to underlying posterior layers of the stroma). When posterior corneal tissue was treated with microparticles, there was a similar particle arresting response observed compared to particles embedding at the anterior surface. Particles embed in the stroma by one to two diameters, but none go deeper than this. AFM data from the literature reports that the posterior stroma has a lower Young's Modulus than the anterior stroma. Penetration observed was a bit deeper than in experiments done on the anterior stroma.

Example 24: Microparticles Ballistically Delivered to the Cornea Stay in Place in the Target Tissue Layer where they are Delivered To assess the ability for tissue to seal up as ballistic particles embed in the material, picosirius red was used to stain the epithelium and stroma and confocal microscopy was used to image individual layers of the tissue surrounding a single particle.

Figure 34:
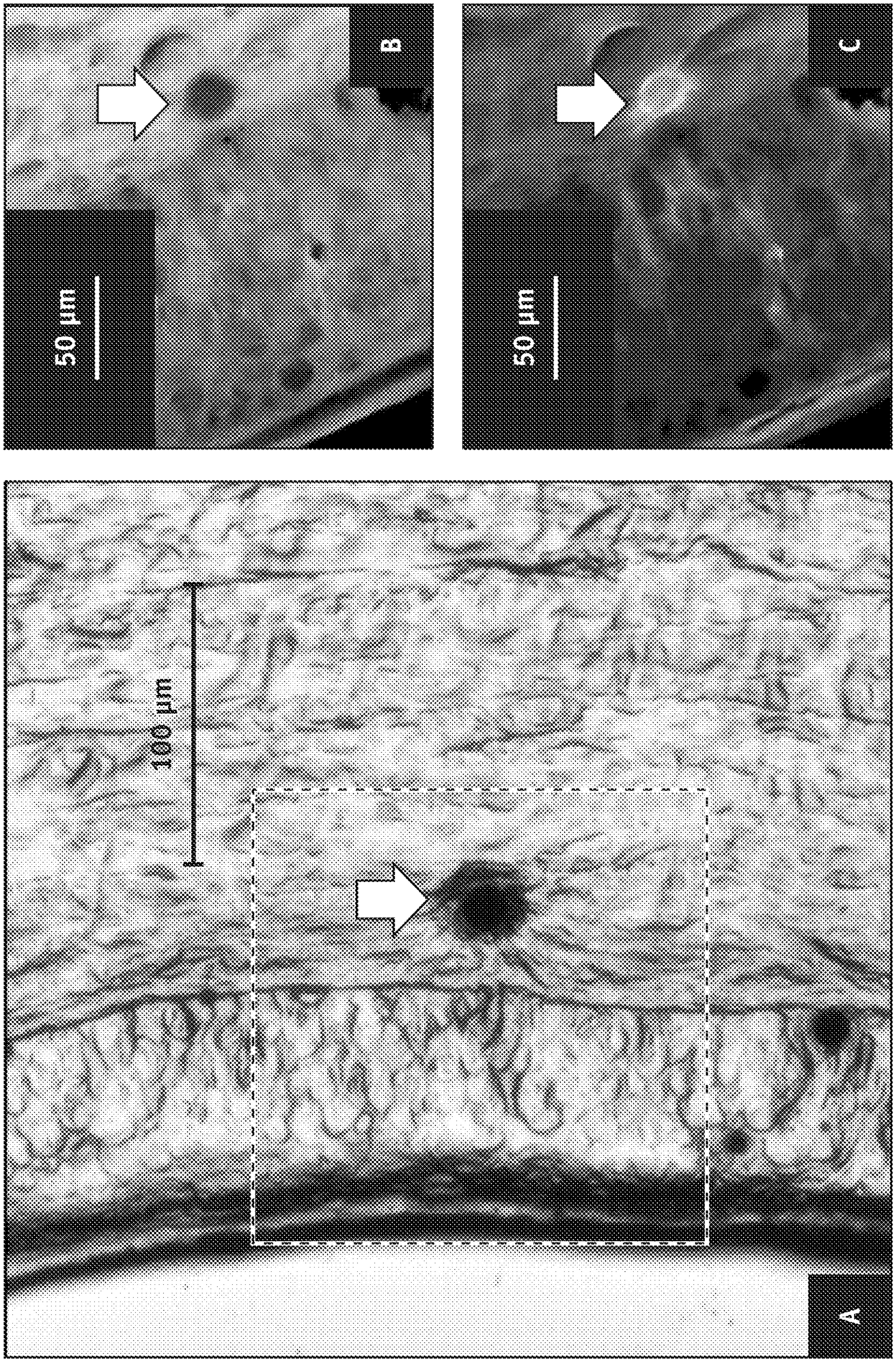
FIG. 34 shows particles create low damage as the embed in tissue, wherein in panel A transmission micrograph of a stainless steel microparticle embedded in the stroma, arrow indicates a single 20 μm particle, in panel B confocal micrograph of picosirius red stained, 30-μm-thick tissue section, arrow indicates same particle as in panel A, image is 20 μm deep in the z-stack, and in panel C confocal micrograph from 10 μm deep in the z-stack.

A transmission micrograph indicating a single particle is shown in FIG. 34 Panel A. Images in FIG. 34 Panels B and C show individual frames from a z-stack measured around the same stainless steel particle in FIG. 34 Panel A.

While embedding was shallow, it is interesting to note that penetration into the epithelium did not leave a visible "track." To the extent observable with optical microscopy, no evidence of tissue damage was seen. When tissue was examined using confocal microscopy, there also was no evidence of noticeable tracks left in tissue. The results show the particle firmly embedded in collagen fibrils in Figure. 34 panel C. There is a local compression of the fibers surrounding the particles and a bright fluorescent signal. The integrity of the epithelium can be seen clearly in FIG. 34 panel B. This frame shows that there are no clear tracks left by the particle in the epithelial layer. This suggests that the ballistic treatment is non-destructive—as particles travel through tissue in the embedding process, the material has the ability to reseal behind the particle. This elastic response is akin to the formation and subsequent collapse of smooth cavities that form when ballistics penetrate homogeneous materials, like ballistic gelatin. This result is promising and indicates that while there may be local compression of tissue, there are no visible channels left behind penetrating particles.

Example 25: Microparticles Penetration in the Cornea Appears to be Density Dependent Observation of the probability density of microparticles shot to the porcine cornea samples prepared according to Example 10.

Penetration of lowest density microparticles (polyethylene; 1.1 g/cc) was superficial in corneal tissue. Accordingly, when target and particle density are equivalent, significant penetration is prevented. A similar result was observed when custom, therapeutic microparticles are delivered to corneal tissue. Despite low penetration depth of projectiles, there was still efficient distribution of therapeutic compound to the cornea. While the epithelium shows most of the staining, there was some staining of the underlying stroma as well. Perhaps having small particles that embed in the apical surface of the cornea that slowly dissolve is a preferable mode of drug-delivery compared to topical administration of drug solution.

In contrast by using tungsten microparticles (density is 19.2 g/cc), there was effective embedment of microparticles in the corneal stroma.

To the best of Applicant's knowledge, this is the first example of ballistic microparticles traversing the epithelium and accessing underlying stromal tissue. However, this result highlights how effective of a momentum sink the corneal stroma is—only with exceptional high density can embedment in the tough fibers of the stroma be achieved. Even with the epithelium completely removed, stainless-steel microparticles still only embed in the stroma to a superficial distance. The stroma does appear to be an effective stopping medium for ballistic microparticles. While the corneal epithelium appears to be able to slow particles down slightly (especially smaller particles), it is likely, considering these experiments, that the primary barrier to microparticle uptake is the stromal interface.

These observations support the conclusion that microparticles with a density lower than 7.8 g/cc embed in the epithelium of a cornea and in particular that density between 2.5 g/cc and 7.8 g/cc will embed in the basal layer of the epithelium. Microparticle with a density higher than 7.8 g/cc and in particular from 7.8 g/cc to 20 g/cc instead are expected to be able to be delivered in corneal tissue layer beyond the epithelium and in particular to Bowman's layer of an eye if present.

The results summarized in Examples 8 to 20 also support the conclusion that the cornea is protected from high velocity microparticles in a different if not better way than gelatine like tissue, and in skin tissue as a stopping medium (Kendal et. al, 2000[31]; Kendal[32]).

Reference is made in this connection the Examples 26 to 33 below which show different models for ballistic delivery in gelatine and skin tissues.

Toughness demonstrated by the cornea is even more surprising, considering the cornea has a higher water constant than skin tissue. The cornea has a reported water content of 76% by mass (Hedbys et al.; 1966[33]), much higher than the exposed surface of the skin's *stratum corneum*, which contains 40% water at the surface and increases to 70% water by the *stratum granulosum* (Warner et al. 1988[34]).

Example 26: Preparation of Ballistic Gelatin Samples

Ballistic gelatin is a material with consistent mechanical properties used in ballistics research. [35, 36] Gels were prepared using the standard protocol (Jusilla et al., 2004 [37]) at three concentrations of 2.5, 5.0 and 10.0% w/w. Gelatin samples were allowed to solidify for 24 hours at room temperature and then for 24 hours at 4° C.

Specification of ballistic gelatin: the term bloom with regard to gelatin may be used in two different contexts.

One refers to the process of softening the gelatin in liquid prior to melting it (e.g., "bloom the gelatin in cold water for 5-10 minutes"). The other use of Bloom refers to the firmness of gelatin. When the rigidity of the gel is measured by the method established by Oscar T. Bloom to the resulting value is called the Bloom Strength. A higher value indicates a stiffer product. Ballistic gels are made using "250 Bloom gelatin", i.e., gelatin that has Bloom Strength of 250.

A procedure for preparing 10% ballistic gelatin is as the following. Using 250 Bloom gelatin (purchased in powder form from a reliable source and stored so that it does not deteriorate), 2 g of gelatin powder was mixed with 4 g of filtered water. Then 14 g of hot water (at 60° C.) was added to the mix. The entire mixture was then stirred at regular intervals of 3 min for 15 s each until the powder was fully dissolved. The mixture was then poured into plastic molds and placed in a refrigerator for 2 h at 5 C. When a sample is removed from the refrigerator, care must be taken so that water does not condense on the gelatin and so that water does not evaporate from the gelatin. The gelatin should be used within 20 minutes after removing it from the refrigerator so that its properties do not degrade.

Example 27: Microparticles Penetration 2.5% to 10.0% w/w Ballistic Gelatin

To show the effect of substrate toughness on particle penetration, microparticles were delivered to gels made with different concentrations. 2.5% and 10% w/w gels were made so that penetration models in Veysset et al. [38] could be used to interpret the data.

Three concentrations of ballistic gelatin were examined (2.5, 5 and 10% w/w) for comparison with prior literature.

The image processing pipeline used processes individual frames, isolates objects with an intensity below a certain threshold, and generates the statistics reported. Each scatterplot shows the result of 300 impacts into the homogeneous material. Data from impacts in 5% w/w gelatin are described in FIG. 35, Statistics were generated based on data from impacts in 5% w/w gelatin, and data in FIG. 36 qualitatively describes penetration in 2.5% w/w and 10.0% w/w ballistic gelatin.

The image processing pipeline measured microparticles that are within the expected size distribution. Some microparticles are larger than the expected range, which is expected since the vendor reports 10% of particles have sizes larger than the reported range. [Q53: Please provide further elaboration as needed]

Figure 37:
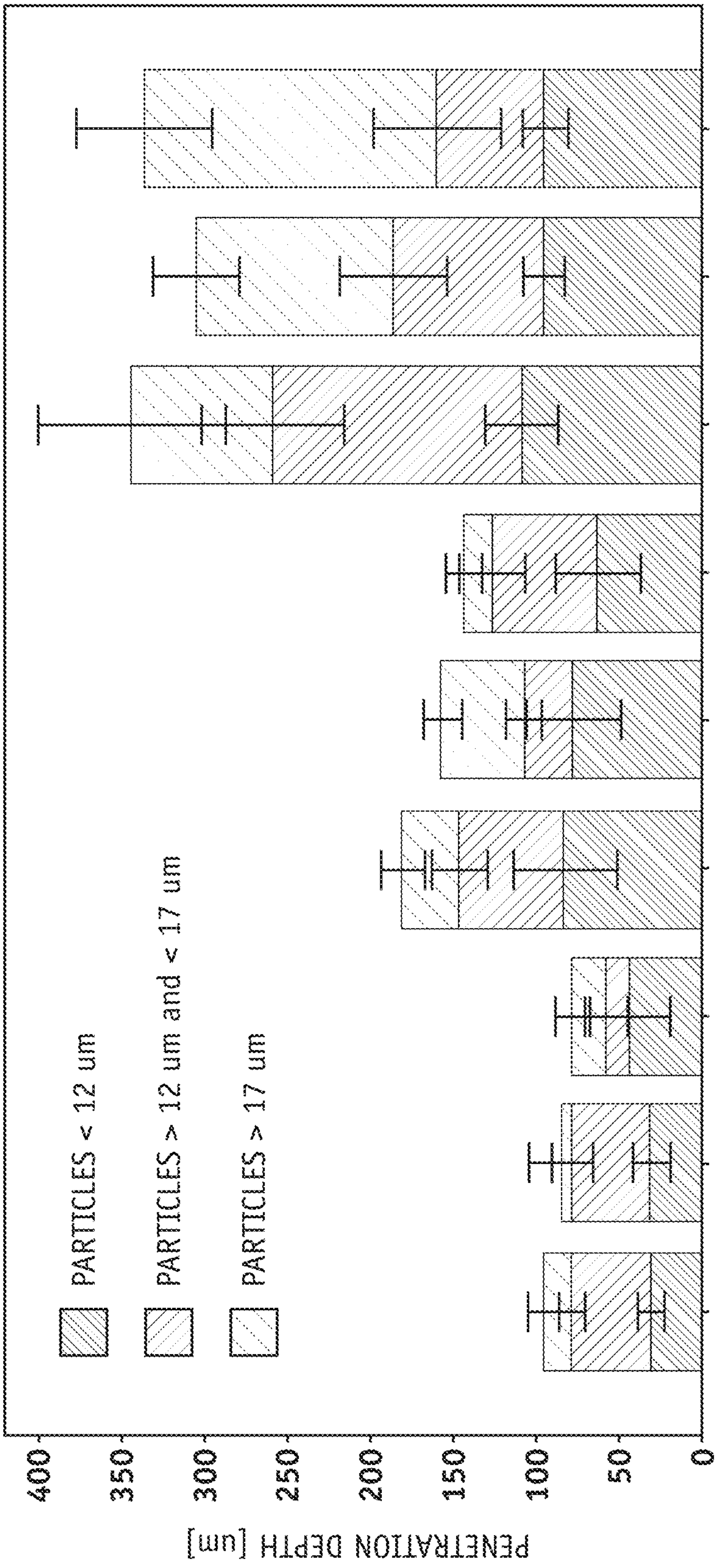
FIG. 37 shows average penetration depth for each of three replicate doses of polydisperse particles delivered into gelatin. The overall bar is the average over relatively large particle diameters; the intermediate bar is the average over particles of intermediate diameter, and the lowest bar is the average over relatively small particles. Error bars show 95% confidence intervals of the penetration depth distribution. SL1=soda-lime glass shot #1, BT2=barium-titanate glass shot #2, and SS3=stainless steel shot #3.

To show the consistency of the ballistic device, mean penetration depths are reported for three different size groupings for soda-lime glass, barium-titanate glass, and stainless steel microparticles. The results of this analysis are shown in FIG. 37.

The mean and standard deviation of penetration computed for each of three replicate experiments shows good reproducibility (FIG. 37): with the exception of the middle-size range for stainless steel, the mean penetration depth for each of three particle diameter groupings are indistinguishable (no statistically significant difference from experiment-to-experiment).

This indicates that particle penetration data is comparable each time the ballistic device is actuated.

Figure 35:
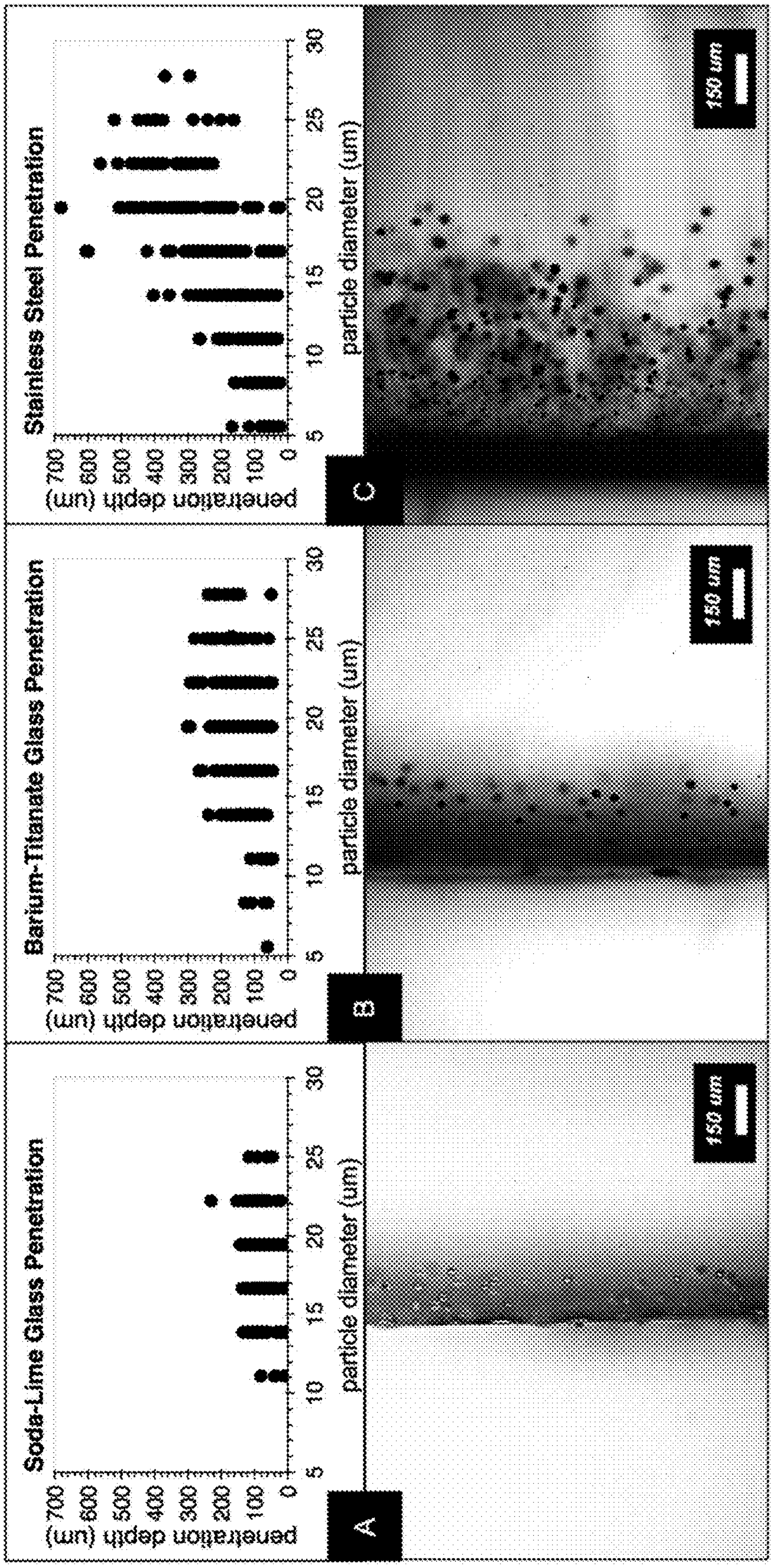
FIG. 35 shows demonstration of particle embedding energies in 5% w/w gelatin. Penetration depth of particles from three shots to gelatin and representative images for soda-lime glass particles in panel A, barium-titanate particles in panel B, and stainless-steel particles in panel C.
Figure 36:
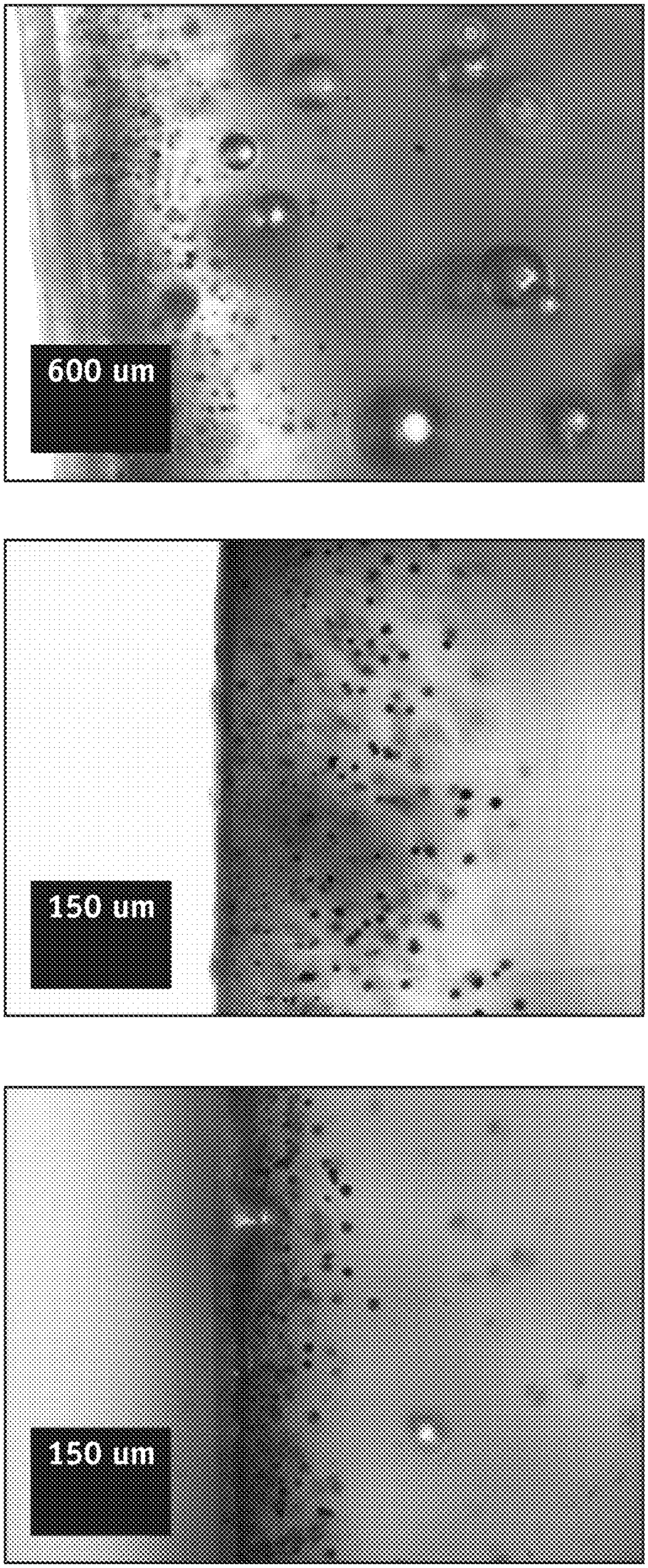
FIG. 36 shows pictures illustrating representative penetration depth of stainless-steel microspheres in 2.5% w/w gelatin (top panel), 5.0% w/w gelatin (middle panel), and 10.0% w/w gelatin (bottom panel).

The statistics generated from data of FIG. 35 and FIG. 36 are presented in FIGS. 38-41. From the image of 2.5% w/w gelatin, it can be seen that some particles penetrate the gel by over a millimeter. The 5% w/w gelatin, penetrates by up to 600 μm. Last, the 10% gelatin penetrates by only 150 to 200 μm. As can be seen, penetration of the steel microparticles was progressively attenuated as the concentration of gelatin was increased.

Figure 38:
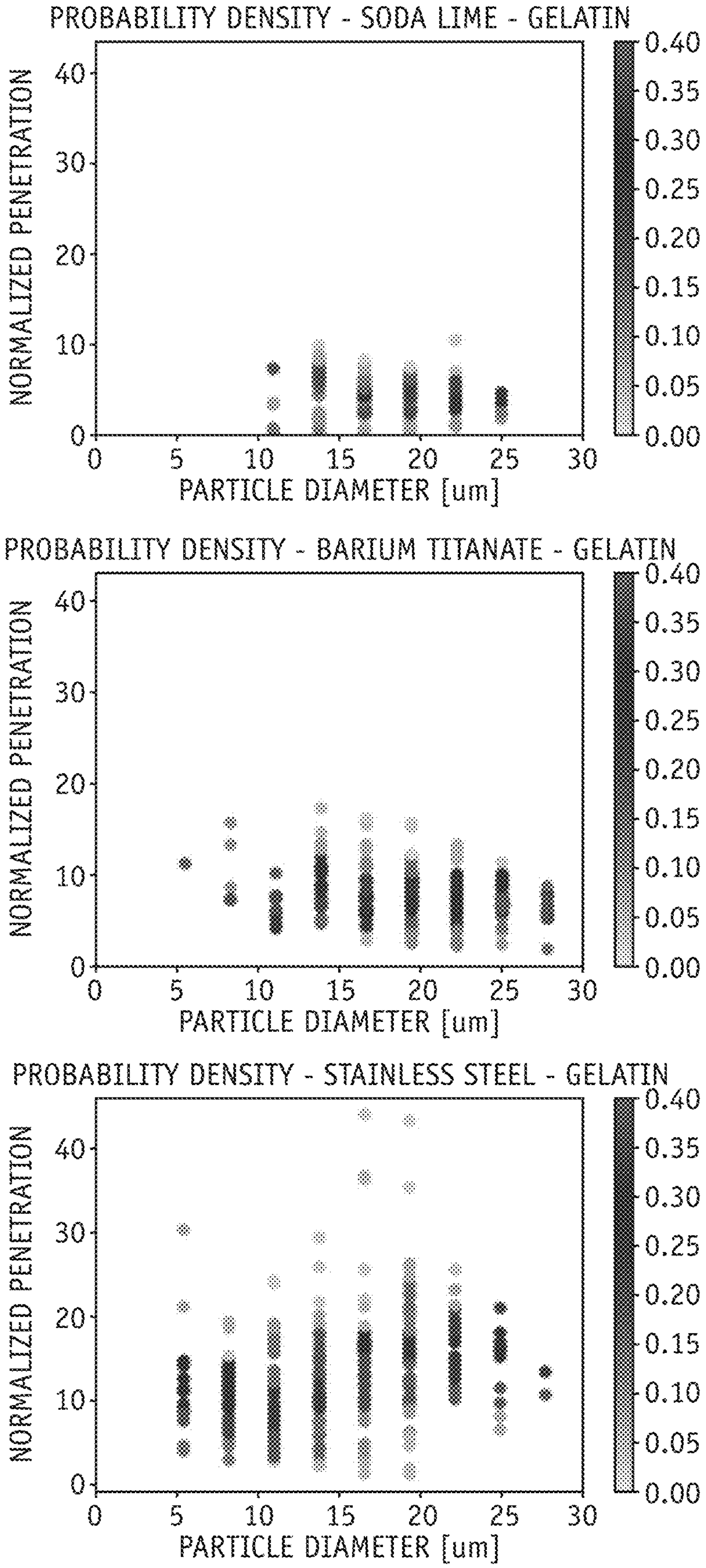
FIG. 38 shows charts illustrating probability densities of soda lime, barium titanate, and stainless steel impacts in 5% w/w ballistic gelatin shown with particle penetration normalized by particle diameter. Probability density for the colormap was calculated by binning data into discreet groups along the x and y axes.
Figure 39:
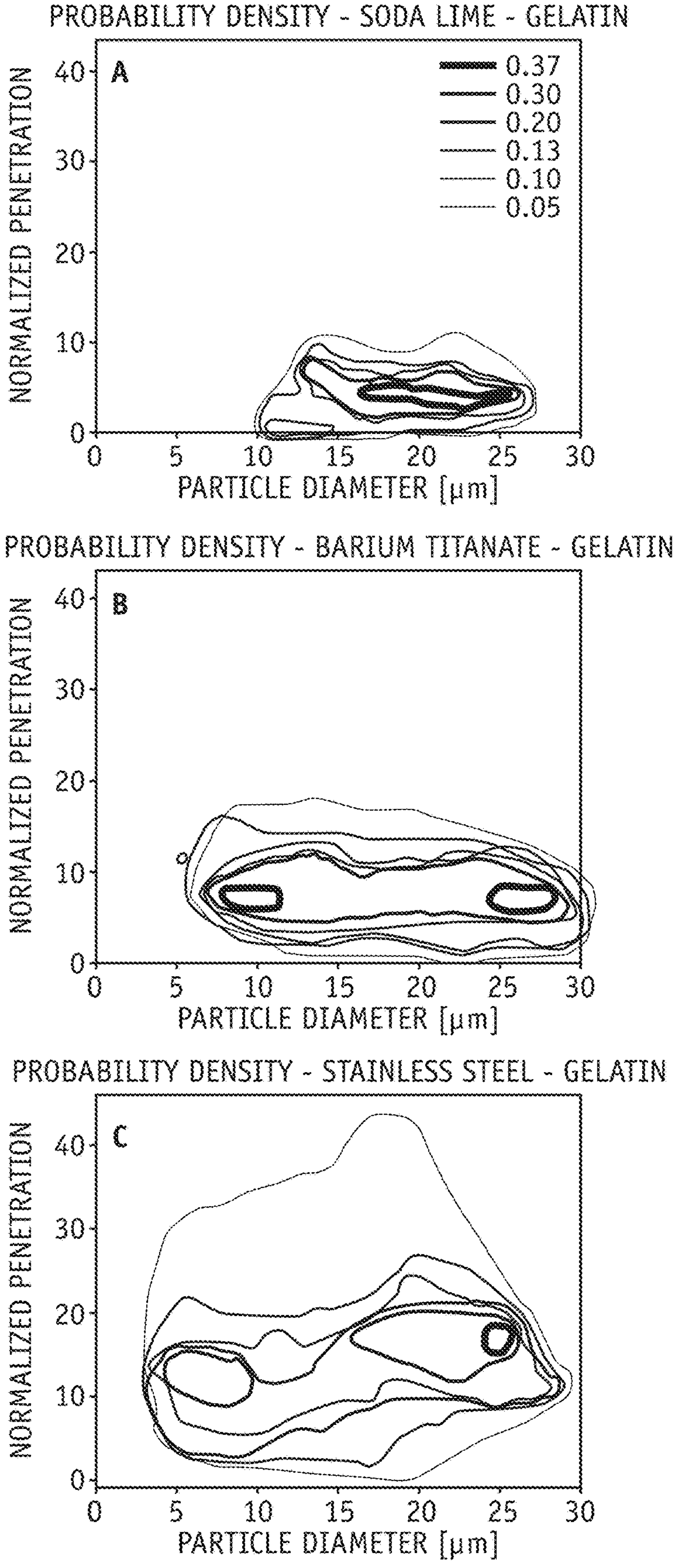
FIG. 39 shows the same data as in FIG. 38 in a contour format.
Figure 40:
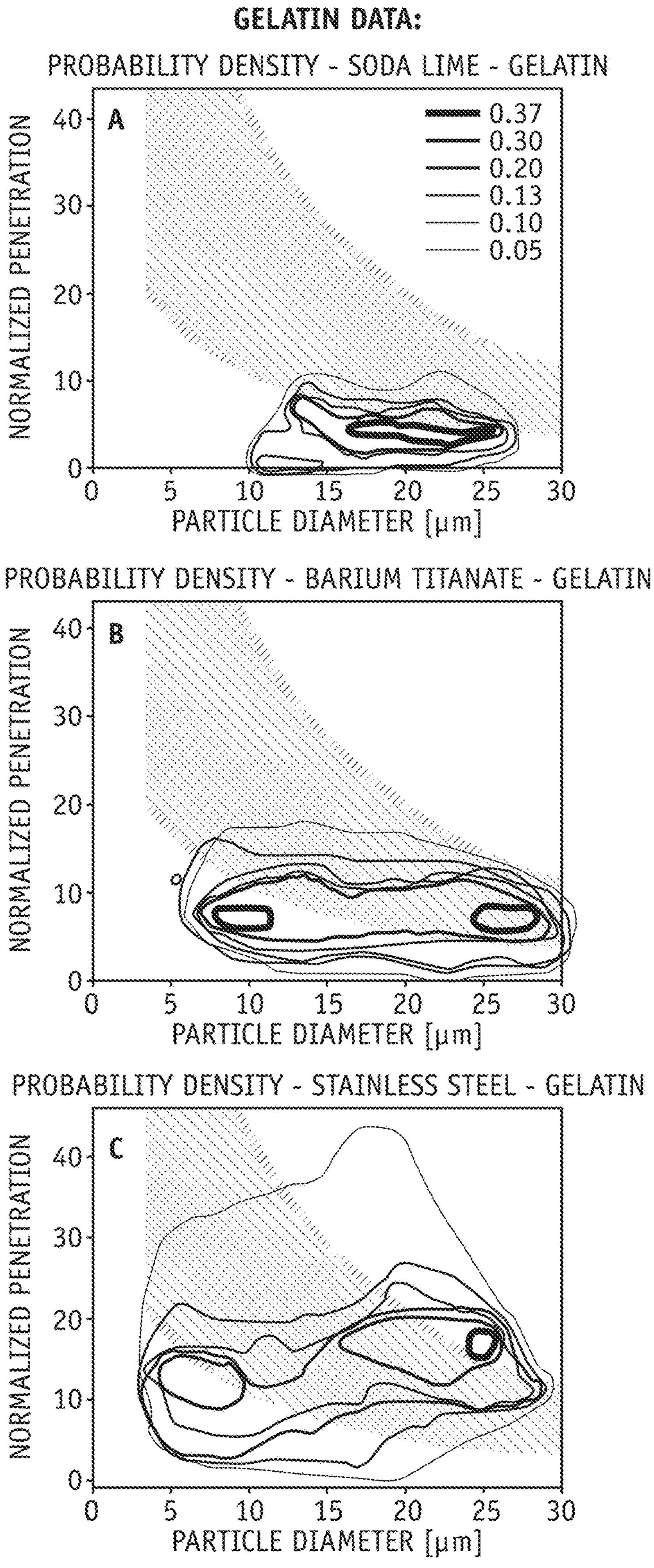
FIG. 40 shows the same data as in FIG. 38 in a contour format with average thickness of the epithelial layer bounded by a standard deviation in the shadowed area.

Using the results of Veysset et al., who show penetration of microparticles into ballistic gelatin conforms to the Poncelet Model (loss of kinetic energy predominantly due to work of fracture) and provide resistance values for the three concentrations examined in this work, we can infer the distribution of impact velocities (FIGS. 38-40). The results indicate the velocity of most microparticles is in the range 150 to 300 m/s, with some particles having impact velocity inferred to be as high as 500 m/s.

Penetration depth $z_\infty$ in the uniform, isotropic gelatin is known to scale with the $$\text{Elastic Froude Number}\frac{z_\infty}{2r_p} \sim \left[\frac{\Delta\rho v^2}{E}\right]^\gamma,$$

where Δρ indicates density difference relative to the target material, v is the impact velocity, E is the shear storage modulus of the substrate, $r_p$ is the particle radius, and γ is an exponent empirically found to be close to one half for projectiles orders of magnitude larger than what is used here (Swain et al.; 2014 [39]).

In Swain et al., this dimensionless group included a difference between the impact velocity and a threshold velocity for embedment, which was proportional to the contact pressure. The estimated impact velocity was used alone in this analysis, due to insufficient knowledge of particle velocity. Direct measurement of particle velocity was not performed, due to the ballistic embedment process being enclosed in a sealed vacuum chamber that made it difficult to film embedment with high-speed imaging. Penetration in this dataset is observed to scale with the Elastic Froude Number to a power of 0.8±0.2 (see Example 5 Table 3 below).

Example 28: Elastic Froude Number Based Scaling Relationship for Penetration in Gel In previous ballistics research, penetration of millimeter-sized projectiles has been shown to scale with the Elastic Froude Number to some power. One can write the following generalized expression for penetration in homogeneous materials:

$$\frac{z_\infty}{D_p} \sim \left[\frac{\Delta\rho u_o^2}{G}\right]^\gamma \tag{6}$$

where $z_\infty$ is the final penetration depth, $D_p$ is the diameter of the particle, and γ is a power which is usually found to be around ½ in gel materials.

In Akers and Belmonte[40], spheres penetrating a viscoelastic, micellar fluid were shown to display maximum penetration depth scaling with $$\frac{z_\infty}{2r_p} \sim \left[\frac{\Delta\rho U^2}{E}\right]^{1/3}.$$

In Swain et al, the penetration of steel spheres in ballistic gelatin was shown to scale with $$\frac{z_\infty}{2r_p} \sim \left[\frac{\Delta\rho U^2}{E}\right]^{1/2}.$$

In Table 3 as described above, the ratio of density differences between target and substrate is compared to the ratio of penetration depths. This was done for small particles (<12 um), medium sized particles (12 μm≤Particles≤17 μm), and large particles (17 μm<Particles). The value of γ in $$\Delta\rho_1^\gamma/\Delta\rho_2^\gamma$$

that fit the data best was 0.79±0.19.

TABLE 3

| Comparing Ratio of Mean Penetration Depths to Ratio of Densities with Exponent γ | | | | | | | | | |
|---|---|---|---|---|---|---|---|---|---|
| | Particles < 12 um | | | 12 um ≤ Particles ≤ 17 um | | | Particles > 17 um | | |
| | $\Delta\rho_{BT}/\Delta\rho_{SL}$ | $\Delta\rho_{SS}/\Delta\rho_{BT}$ | $\Delta\rho_{SS}/\Delta\rho_{SL}$ | $\Delta\rho_{BT}/\Delta\rho_{SL}$ | $\Delta\rho_{SS}/\Delta\rho_{BT}$ | $\Delta\rho_{SS}/\Delta\rho_{SL}$ | $\Delta\rho_{BT}/\Delta\rho_{SL}$ | $\Delta\rho_{SS}/\Delta\rho_{BT}$ | $\Delta\rho_{SS}/\Delta\rho_{SL}$ |
| experimental- $Z_{\infty 1}/Z_{\infty 2}$ | 2.10 | 1.34 | 2.81 | 1.77 | 1.59 | 2.81 | 1.86 | 2.05 | 3.81 |
| theoretical- $\Delta\rho_1^\gamma/\Delta\rho_2^\gamma$ | 2.10 | 1.33 | 2.79 | 1.77 | 1.59 | 2.79 | 1.86 | 2.05 | 3.84 |
| Abs(experimental-theoretical) | 0.00 | 0.00 | 0.01 | 0.00 | 0.00 | 0.02 | 0.01 | 0.00 | 0.02 |
| $\gamma_{min}$ | 0.96 | 0.39 | 0.68 | 0.74 | 0.99 | 0.68 | 0.8 | 0.97 | 0.89 |
| | | | | | | | | $\bar{\gamma}_{min}$ | 0.79 |
| | | | | | | | | Standard deviation | 0.19 |

Example 29: Poncelét Model of Veysset [38]

For a microparticle penetrating tissue, there are three main forces experienced: 1) friction, 2) intertial resistance from acceleration of tissue around a particle, and 3) resistance of the material to cracking/deformation. The Poncelét model assumes that friction is negligible compared to inertial and resistance terms. The resulting kinematic equation is shown below:

$$m_p\frac{dv}{dt} = B_2v^2 + B_o \tag{7}$$

$$B_1 = \frac{1}{2}C_D\rho_S A \text{ and}$$

$$B_2 = AR$$

where A is the area of a particle, $\rho_s$ is the target density, and R is a gel resistance term that is typically correlated to yield stress. Integrating this equation twice, using the impact speed and the relation between distance and velocity, yields the following expression:

$$z(t) = \frac{m_p}{B_1}\left[\ln\ \cos\left(\frac{\sqrt{B_1B_2}}{m_p}(t_f - t)\right) - \ln\ \cos\left(\frac{\sqrt{B_1B_2}}{m_p}t_f\right)\right] \tag{8}$$

Where $t_f$ is the time that it takes for the particle to come to rest, given by:

$$t_f = \frac{m_p}{\sqrt{B_1B_2}}\tan^{-1}\left(v_o\sqrt{\frac{B_1}{B_2}}\right) \tag{9}$$

Finally, the max penetration depth is given by the following expression:

$$z_{max} = \frac{2}{3}\frac{\rho_pD_p}{\rho_sC_D}\ln\left(\frac{\rho_sC_Dv_o^2}{2R} + 1\right) \tag{10}$$

where $z_{max}$ is the maximum penetration depth, $\rho_p$ is the density of the particle, R is the resistance of the material to penetration, and $C_D$ is a drag coefficient. This maximum penetration is not always the final resting depth of a particle. In elastic media like gelatin, research has shown that microparticles can spring backward after forming long cavities. This elastic recoil results in shallower penetration than is ultimately measured in gelatin for a given impact velocity, but this equation is still helpful in estimating a lower bound for impact velocity.

Using our normalized penetration depth data, the penetration observed in ballistic gelatin can be compared with the Poncelet Model to estimate impact velocity. To do this, the mean particle penetration was calculated as well as the maximum penetration depth. By plotting the data in FIGS. 38-41 on curves showing the expected penetration in 5% w/w gelatin (as predicted by the model), a range of impact velocities can be inferred using data from soda lime glass and barium titanate glass penetration. In both figures, the mean penetration of the sample shows up with normalized penetration depth indicating a velocity of a little over 200 m/s. Standard deviation of the penetration depth data set indicates that most particles have velocities from 150 to 300 m/s.

Figure 41:
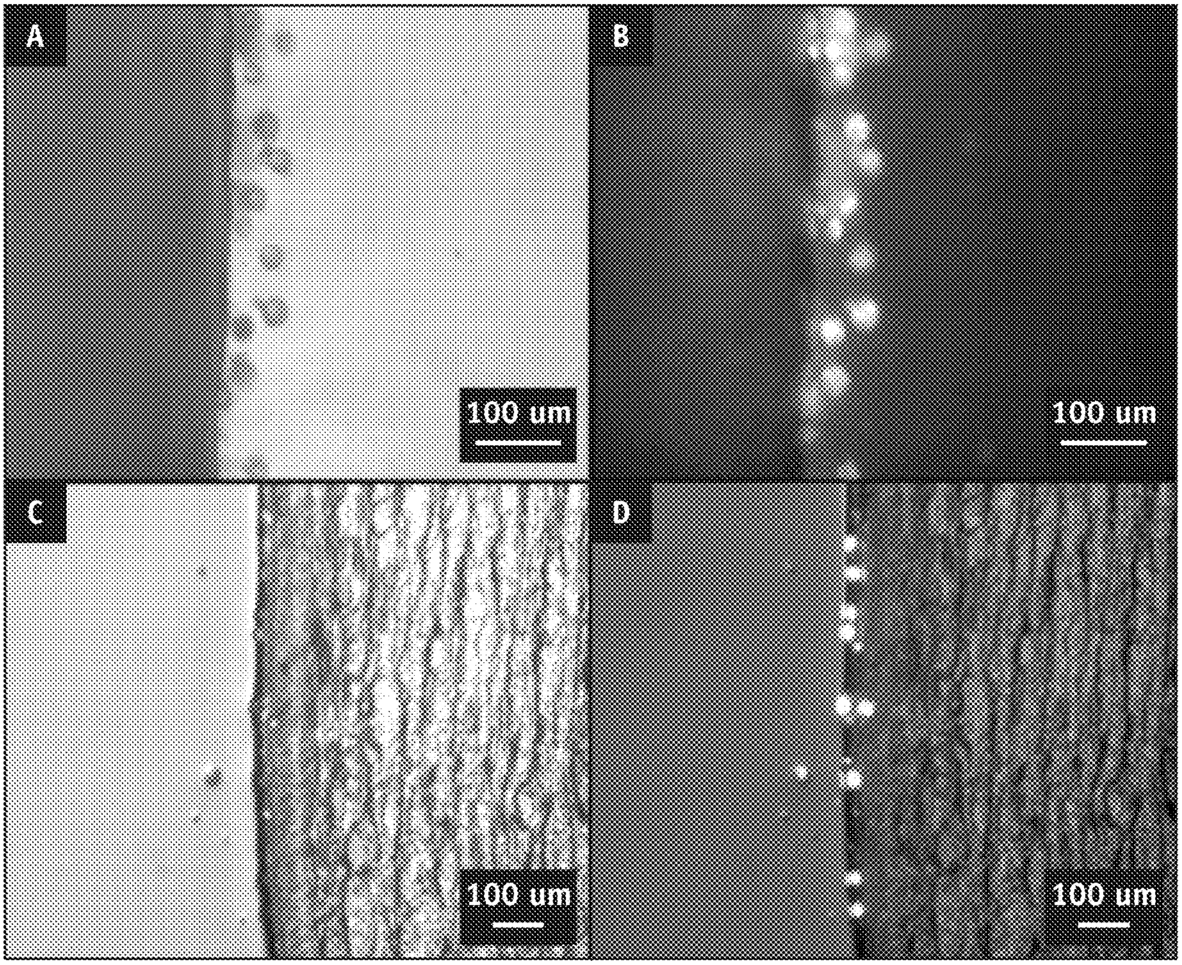
FIG. 41 shows pictures illustrating penetration of 1.1 g/cc polyethylene spheres in gelatin and corneal tissue, wherein in panel A bright-field microscopy of 5% w/w gelatin, in panel B fluorescent micrograph of gelatin, in panel C PE spheres in corneal tissue (brightfield), and in panel D PE spheres in corneal tissue.

The maximum penetration depth in the figures corresponds to an impact velocity around 500 m/s. Data from stainless steel impacts in 5% and 10% w/w ballistic gelatin shown in FIG. 41 indicates slightly different penetration depths. The data from 5% w/w gelatin compared to the Poncelet Model indicates an impact velocity of around 200 m/s, but the data from impacts in 10% w/w gelatin indicates an impact velocity for the mean penetration depth of 300 m/s. The maximum penetration for both datasets indicates a maximum impact velocity of around 500 m/s. The reason that the 10% w/w gelatin compares differently to the Poncelet Model may have to do with using a lower number of penetration statistics to calculate mean values. The actual data used to calculate these values is shown in FIG. 41 and there are only 75 points in the dataset as opposed to 300.

Based on this analysis, a range of microparticle velocities is expected to be between 150 and 500 m/s, with most microparticles having a velocity of 150 to 300 m/s. This range is not only broad, it is likely an underestimation due to the elastic recoil in gel. The fact that the three different sets of penetration data for soda-lime, barium-titanate, and stainless-steel microparticles show similar predicted impact velocities suggests that The Poncelet Model fits the data well. While the prediction of velocity at least indicates that the microparticles tested as described herein had impact velocities on the order of hundreds of meters per second.

Example 30: Probability Density of Microparticle Ballistic Delivery in Gelatine

Figure 42:
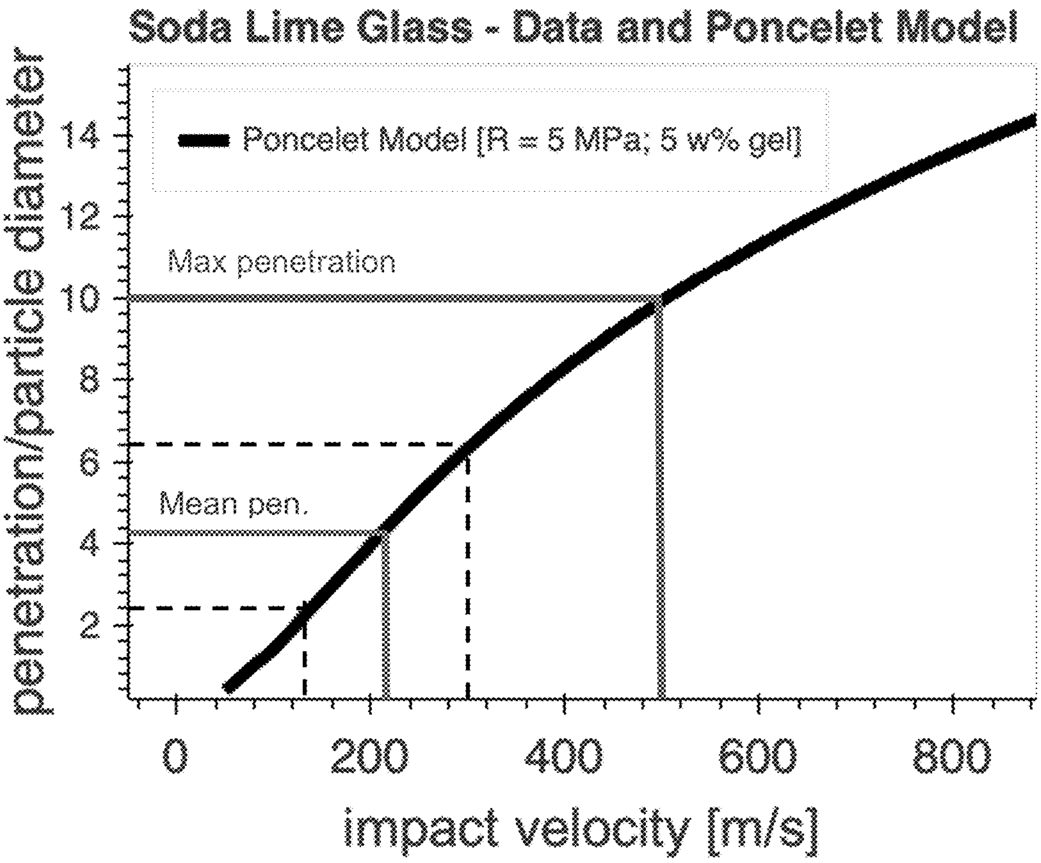
FIG. 42 shows a chart illustrating the Poncelet model for maximum penetration of spheres with density of 2.5 g/cc. Blue intercept line shows average measured penetration depth of soda-lime spheres embedded in 5% w/w gelatin. Dotted lines show one standard deviation above and below the mean. Dash-dot intercept line shows the penetration depth and the corresponding impact velocity of a microparticle embedding at the maximum recorded normalized penetration.
Figure 43:
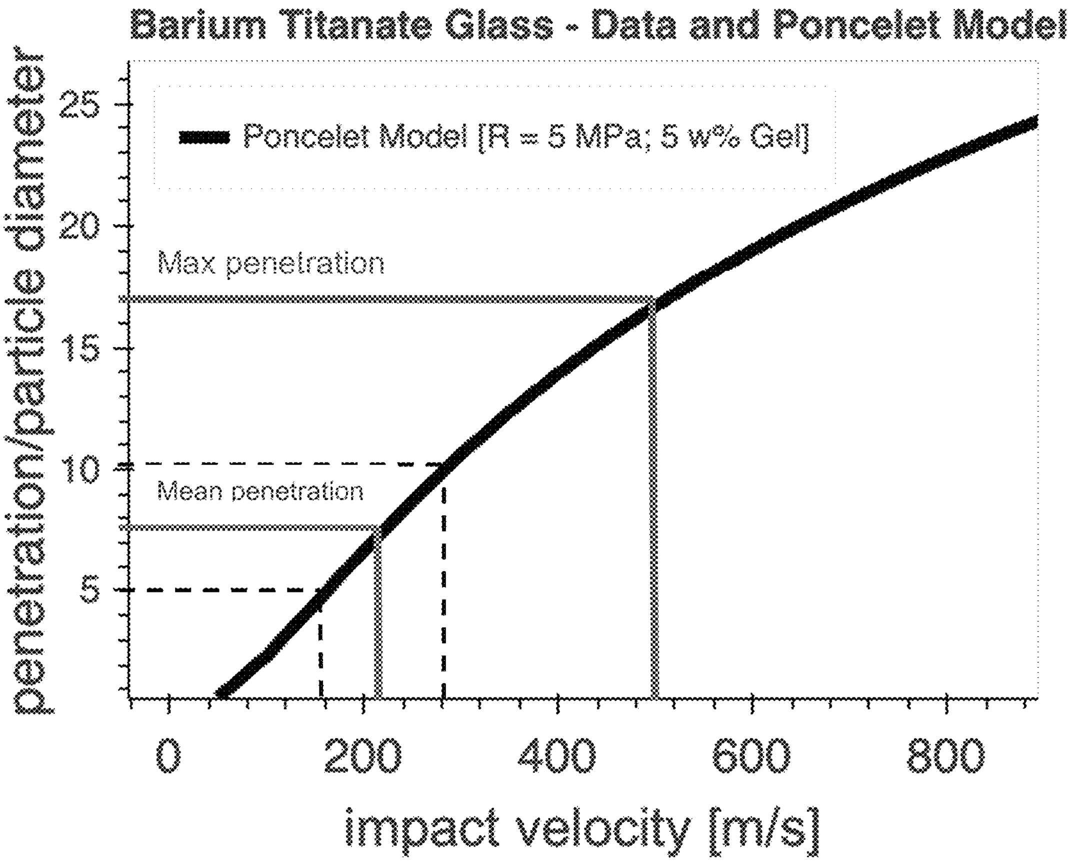
FIG. 43 shows a chart illustrating the Poncelet model for maximum penetration of spheres with density of 4.2 g/cc. Solid intercept line shows average measured penetration depth of barium titanate spheres embedded in 5% w/w gelatin. Dotted lines show one standard deviation above and below the mean. Dash-dot intercept line shows the penetration depth and the corresponding impact velocity of a microparticle embedding at the maximum recorded normalized penetration.
Figure 44:
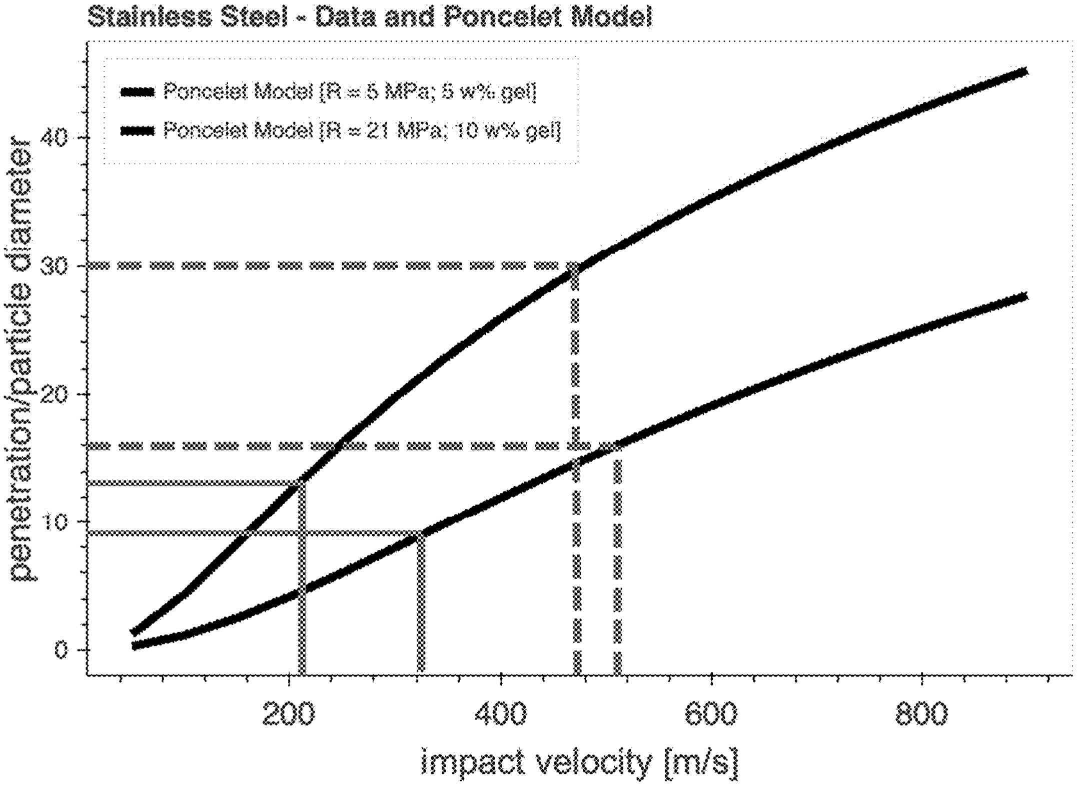
FIG. 44 shows a chart illustrating the Poncelet model for maximum penetration of spheres with density of 7.8 g/cc. Solid intercept lines show average measured penetration depths of barium titanate spheres embedded in 5% w/w and 10% w/w gelatin. Dotted lines show one standard deviation above and below the mean. Dash intercept line shows the penetration depth and the corresponding impact velocity of a microparticle embedding at the maximum recorded normalized penetration.

The results in gelatin lay the foundation for interpreting the particle penetration observed in the cornea, which is dramatically different. Both small and large particles embed to similar depths in the corneal epithelium. Like the images shown in FIG. 41, most particles can be found between 30 and 60 μm deep. The probability density for the normalized penetration depth in ballistic gelatin is insensitive to particle size, as expected (FIGS. 42-44). In gelatin, increasing relative density of the particles relative to the sample conforms with the expected proportional increase in normalized penetration. In contrast, normalized penetration into the cornea is not independent of particle size and does not simply increase proportionally with the particles' relative density (FIG. 20 Panels A-C).

Figure 45:
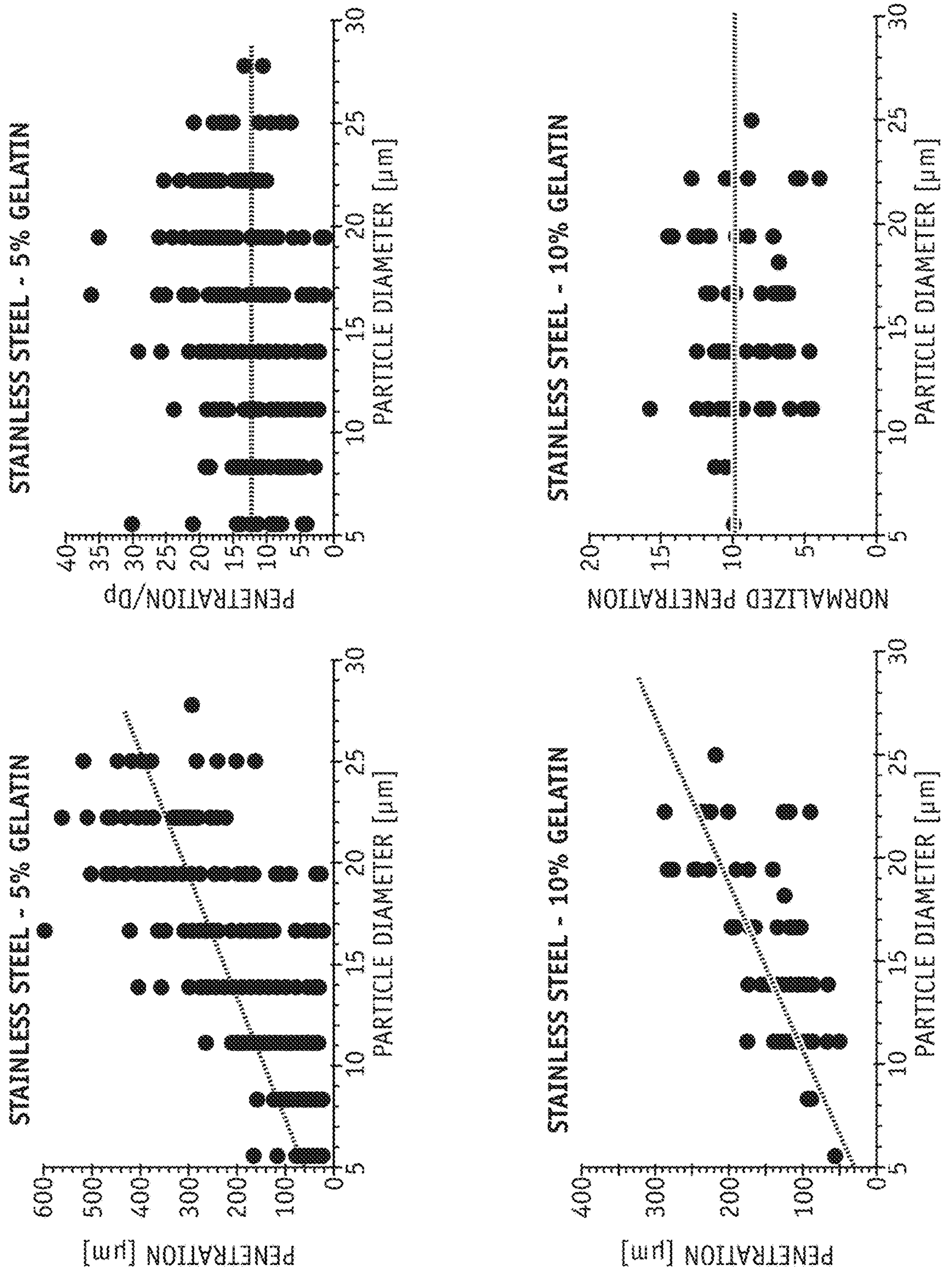
FIG. 45 shows charts illustrating actual penetration in left panels and normalized penetration in right panels of stainless steel particles delivered to 5% w/w ballistic gelatin in top panels and 10% w/w ballistic gelatin in bottom panels, wherein the data for 10% w/w ballistic gelatin are collected from images of 75 particles embedded in gelatin in total.

Example 31: Inference of Impact Velocities from Penetration Depth Data in Ballistic Gelatin The resistance values as referred to in Veysset allows inference of impact velocities from penetration depth data in ballistic gelatin. In FIG. 45, predicted penetration depths are shown for two different particle compositions, using the Poncelet Model. The curves show expected penetration depth in three concentrations of gelatin, 2.5% w/w, 5.0% w/w, and 10.0% w/w. The data is produced by dividing Equation (4) by particle diameter and graphing the results. From experimental data in Veysset et al., resistances of 1.5 MPa, 6.0 MPa, and 21 MPa are used in the penetration equation for the previously mentioned respective concentrations of gelatin, 2.5% w/w, 5.0% w/w, and 10.0% w/w.

The results of this analysis reinforce the importance of projectile density. In FIG. 45, the expected penetration of a polymer particle with density of 1.1 g/cc and a stainless-steel particle are shown. At low density, particles require velocities of several hundred meters per second in order to achieve just a few diameters of penetration. In fact, the model equation predicts the maximum depth reached in gel and does not consider elastic rebounding of particles, which can further attenuate penetration depth. As gelatin concentration increases, it becomes harder and harder for the spheres to embed. When the particle is made of stainless steel, the minimum velocity needed to achieve significant penetration is much lower, and the penetration that is possible for the projectile is considerably higher. These figures show that by changing particle density, a broad range of penetration in gel substrates can be achieved.

Example 32: Penetration of Low-Density Microparticles and Medicinal Microparticles in Gelatine and Cornea (Comparative)

Lowest-density microspheres (1.1 g/cc poly(ethylene)) failed to demonstrate any significant embedding depth in gelatin or in corneal tissue. In FIG. 41 panel A and FIG. 41 panel B, it can be seen that these projectiles only embed in 5% w/w gelatin by one to three diameters. The embedding depth is much shallower than all other materials tested.

Figure 46:
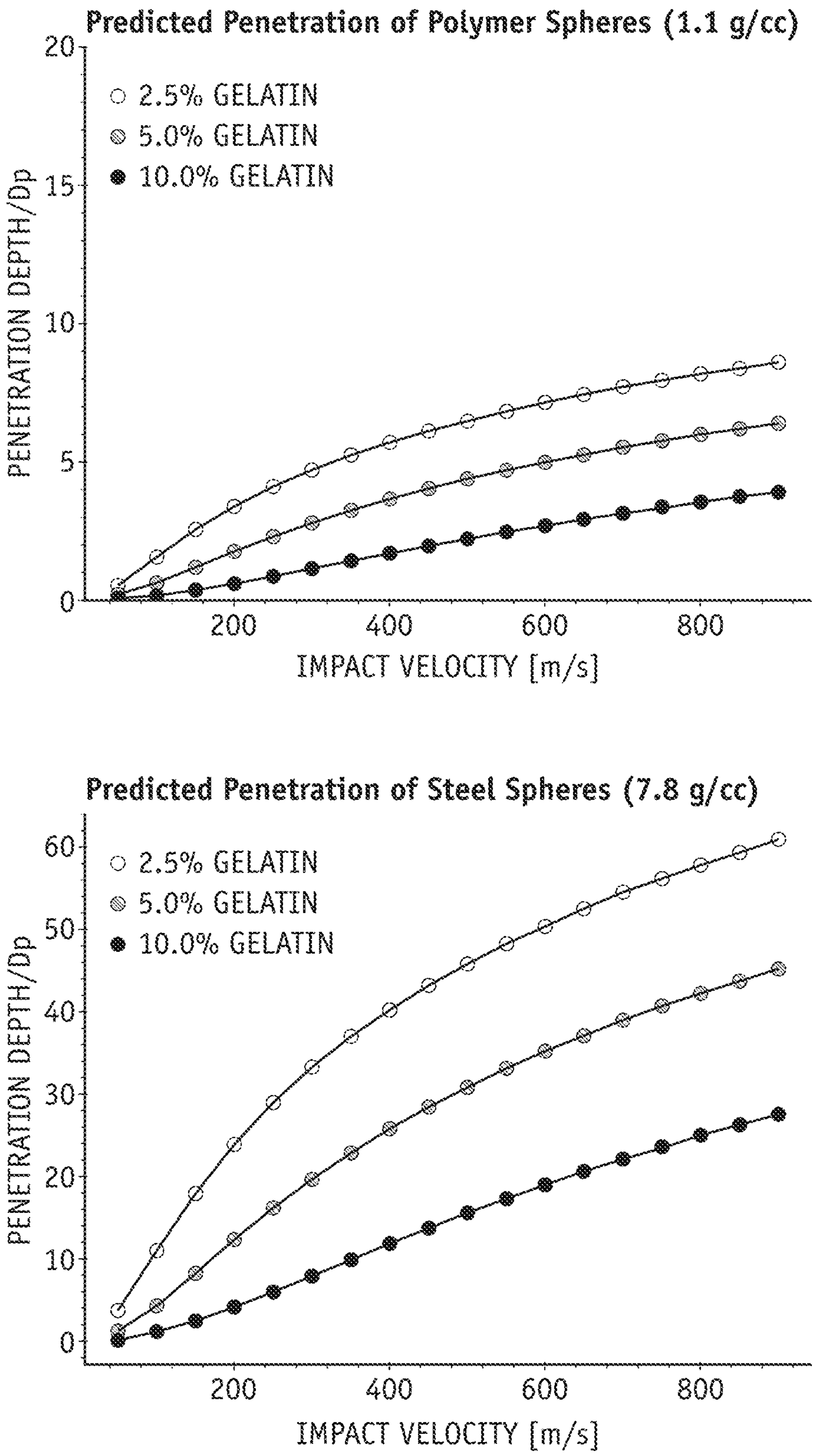
FIG. 46 shows a chart illustrating the penetration depth of two different particle compositions in gelatin predicted by the Poncelet Model. Low density polyethylene in top panel and stainless steel in bottom panel each in 2.5% (upper curve), 5% (middle curve), and 10% (lower curve) w/w ballistic gelatin. Data calculated using resistance parameters and model from Veysset et al.

Not surprisingly, when corneal tissue was tested with these particle payloads, penetration was superficial. FIG. 46 panel C and FIG. 46 panel D show fluorescent microparticles embedded just at the surface of tissue.

This is in line with the description of FIG. 18 panel A and FIG. 18 panel B show PEG microparticles with 1% w/w Eosin Y embedded in the anterior surface of the cornea. These images were taken 10 minutes after ballistic delivery, and it can be seen that microparticles are dissolving into the surrounding tissue.

Following the tissue fixation protocol two days later, FIG. 18 panel C and FIG. 18 panel D show the staining of the epithelium with Eosin Y. Microparticles have fully dissolved, and there is a strong staining of the corneal epithelium with the fluorescent Eosin dye. There is also considerable staining of the stroma below.

Example 33: Model for Shallow Penetration in Tough Materials

For shallow penetration in tough materials (e.g. microparticles embedding in skin), the cavity strength model is used. In this model, the impact pressure is assumed to be equal to the cavity strength during impact, which is about 3 times the yield strength [41]. Therefor, the cavity strength model is written:

$$dE = Fdx \rightarrow dE = 3Y_M A_p dx \quad (11)$$

where E is the energy of the particle, F is the force from impact, $Y_M$ is the material yield strength, and $A_p$ is the area of the projectile. This expression can be integrated and arranged into a predictive equation for penetration depth, which is proportional to $$\rho r u_o^2,$$

a value that is used to plot shallow penetration of ballistics (the kinetic energy per unit cross-section):

$$z_\infty = \frac{\frac{1}{2} m_p u_o^2}{3Y_M A_p} = \frac{\rho_p R_p u_o^2}{6Y_M} \quad (12)$$

where $z_\infty$ is penetration depth, $u_o$ is the impact velocity, $m_p$ is projectile mass, $\rho_p$ is its density, and $R_p$ is its radius. In Kendall-Wright Smith et al. [31], it is shown that penetration in human cadaver skin fits well to a similar model, the fracture toughness model, for different particles sizes, densities, and impact velocities [31]. Skin is a useful tissue to compare the cornea to, because it is a heterogeneous material composed of tissue layers with different mechanical properties, similar to the corneal epithelium and the underlying stroma.

Example 34: Preparation of Microparticles Using PLA as Carrier Material the preparation of poly(lactic acid) microparticles with varying amounts of L and D stereoisomer content. It is thought that by changing the ratio of these monomers, then the rate of particle hydrolysis can be controlled. The particles were prepared using an emulsion-based preparation. Polymer was dissolved in dimethyl sulfoxide and this solution, which is immiscible in water, was mixed in a solution of 1% PVA. Once DMSO evaporates from the immiscible phase, solid, PLA microparticles are left behind. The process of preparing microparticles this way is described in . . . . In addition to using PLA, $CuSO_4$ was dissolved in methanol and quickly mixed with the DMSO solution. $CuSO_4$ was added to the PVA solution as well to try and load the microparticles with $CuSO_4$. The goal is to have microparticles that leech copper ions, which can act as a cofactor for lysyl oxidase, an enzyme that cross-links collagen fibrils. The purpose of this work was to try and enable light-free cross-linking of the cornea facilitated by therapeutic, ballistic microparticles.

Example 35: Biolistic Microparticles to Deliver Applied Ophthalmic Medicines

The results reported in the previous example support the use of high velocity microparticle bombardment as a means of embedding drugs in the cornea's epithelial barrier.

Drug delivery to the cornea is limited by several mechanisms. Natural lacrimation and blinking remove hydrophilic drugs, and the corneal epithelium (a lipophilic tissue layer) has tight junctions between stratified epithelial cells that prevent many drugs from diffusing into the tissue (Ableson et al., 2009) [42]. Enhancing drug uptake into the cornea has the potential to improve treatments for diseases of the eye. For example, Novosorb, a cationic emulsion which binds to the mucin layer on the eye's anterior surface (made by PolyNovo), has had success in delivering latanoprost, a prostaglandin analog which lowers intraocular pressure for patients with glaucoma (Daull et al., 2017) [43].

An exemplary use of the particles and method of the disclosure that illustrates the range of particle size and corresponding number of particles to deliver a relevant dose of drug is delivery of cross-linking therapeutic to treat corneal ectasias.

Corneal cross-linking surgery (CXL), a procedure in which photosensitizing cross-linking agents are used to reinforce the mechanical properties of the cornea (Gordon-Shaag et al., 2015) [44], requires delivery of cross-linking agents (e.g. riboflavin and Eosin Y) to the stroma. Slow transport through the epithelium is usually overcome by removing the epithelium to access the stromal layer. Techniques to improve the flux of cross-linker are under development, like the use of iontophoresis and proteins that disrupt epithelial tight junctions, but in the US epithelium-off CXL remains the standard of care for keratoconus, despite a reduction in post-operative complications (Cifariello et al., 2018 [45]; Jia et al., 2018 [46], Bidwell et al., 2014 [47]). If particles with a large volume fraction of drug were used, a sufficient dose might be provided biolistically to deliver 6,000 particles of 30 μm diameter distributed across 1 $cm^2$ of corneal tissue, potentially in the blink of an eye (Huynh 2011 [48]).

Example 36: Ballistic Devices

In the preceding Examples A BioRad PDS-1000 gene gun (catalog #: 1652257) was used. Additional device can be used to deliver the microparticles of the disclosure to be selected based on the indications herein provided concerning type of particles related dimensions and density, target regions, as will be understood by a skilled person upon reading of the present disclosure.

For Example devices for the delivery of genetic materials to the cornea using metal microparticles such as the one described in Zhang et al. [6] can be used. They observed that particle delivery using an unmodified BioRad Helios device resulted in injury: all of the corneas that received particles from the unmodified BioRad Helios were positive for fluorescein eye drops, indicating that the epithelium was ruptured allowing fluorescein to pass from the tear film into the stroma.

To minimize corneal epithelial defects and to maintain a constant distance between the gene gun and the cornea, a device was developed that can be mounted in front of the Helios gene gun and put firmly on the orbital rim. For application to the present invention, calibration experiments for a specific particle size distribution, and for specific particle shape and density. The calibration can be performed following the procedure described in Example 31. The measured profile of penetration depth as a function of particle size in the specific particle size distribution provide a size-dependent velocity delivered at the constant distance provided by the improvements of Zhang et al. relative to the unmodified Helios. Another example of a delivery device that can be used comprises the particle accelerating device developed by Groisman as illustrated by the procedure in Example 10.

For conditions in which the calculated velocity required to achieve delivery to a selected target region for a selected particle size distribution, shape and density is in excess of Mach 1 (approximately 344 m/s in air at ambient pressure and temperature), a device that can be used comprises the particle delivery device laser-induced particle impact test (LIPIT) platform, in which an intense short laser pulse is used to accelerate microparticles to supersonic velocities [38]. Calibration of the device for use in the present invention is required and follows the literature protocol to observe particle impact events with a high-frame-rate camera and analyze the time sequence of images to determine the velocity that is provided for a specific particle size, shape and density.

Example 37: Microparticle Biolistic Delivery

Polylactide (PLA) is an exemplary carrier for copper minerals as an exemplary biologically active cargo to address the clinical need to provide sustained release of $Cu^{2+}$ in the cornea. Sustained release of $Cu^{2+}$ in the cornea is therapeutically used to enhance lysyl oxidase activity and thereby increase enzymatic crosslinking and halt progressive thinning and bulging of the cornea in keratoconus. The use of $Cu^{2+}$ for treatment of keratoconus has been demonstrated by Dr. Bala Ambati. The clinical results dictate the copper dose and time-course of release. Copper minerals that dissolve over days to weeks. Polylactide (PLA) is a vehicle that can delay release relative to a mineral delivered without a carrier. PLA also has the desirable feature that it tends to lower the pH as it is hydrolytically cleaved to lactic acid, which will mitigate increases in pH as the basic copper minerals dissolve.

Keratoconus (KCN) is a progressive disorder that leads to corneal thinning and bulging with typical onset at approximately 15-16 years of age[49]. Mild KCN can be corrected with glasses or soft contact lenses; as the disease progresses, large, irregular refractive errors become difficult to correct and ultimately 1 in 5 patients require a corneal transplant, [50] with associated risk of intraoperative and post-operative complications (bleeding, scarring, cataract formation, etc.). [51] Over the past decade, a surgical method to slow or halt progression of KCN, Corneal Collagen Crosslinking (CXL), has reached the clinic. In the US, the approved procedure requires epithelial scraping, application of riboflavin drops and prolonged exposure to UV-A to generate singlet oxygen that leads to formation of protein crosslinks that stabilize the cornea.[52] Because the procedure involves stripping the epithelium, it is associated with severe pain, temporary visual loss, stromal haze and infections.[53-57] In addition, the CXL therapy cannot be used in patients with thin corneas due to the risk of permanent damage to the cornea.

Dr. Bala. Ambati developed the concept of treating KCN by enhancing corneal crosslinking without the need for photoactivation. Insufficient physiologic corneal crosslinking plays an important role in KCN, particularly crosslinking mediated by lysyl oxidase (LOX),[58-60] which converts lysine to allysine that spontaneously conjugates to lysine or hydroxylysine, forming lysinonorleucine (LNL) or hydroxy-LNL (HLNL) crosslinks. These adducts render collagen and elastin insoluble, providing a stable extracellular matrix. Ambati performed in vitro and in vivo preclinical experiments which showed that increasing [$Cu^{2+}$ ] can restore LOX activity, increase crosslinking as measured by LNL in rabbit cornea treated topically, and increase biomechanical strength of human cadaver corneas and rabbit corneas ex vivo. In clinical trials, the treatment involves topical application of a copper sulfate solution, IVMED-80 eye drops, morning and evening. IVMED-80 has the potential to become the standard of care as it would be the first purely pharmacologic intervention for KCN. Efficacy relies on patient compliance and transport of $Cu^{2+}$ across the epithelium. Copper has a narrow therapeutic range (100 μM to 1 mM) above which it is toxic, creating a situation in which sustained release could be particularly beneficial. Therefore, a method to provide sustained release of $Cu^{2+}$ in the cornea is needed.

Biolistic delivery will quickly deliver Cu(II) in a sustained release vehicle to maintain a therapeutic [$Cu^{2+}$ ] for weeks, eliminating variability associated with patient compliance and transport across the corneal epithelium. Based on the formulation of IVMED-80 currently in a Phase 1/2a clinical trial, we estimate that the corneal stroma receives $1.6\times10^{-9}$ g of $CuSO_4$ per topically applied eye drop, corresponding to $2\times10^{-11}$ mol Cu(II)/day. This estimate is consistent with observations during the first 4 months of the current clinical trial that patient's eyes have no visible blue color and color vision is not affected (patients received eye drops twice daily for 16 weeks in three groups: vehicle, IVMED-80, and 6 weeks IVMED-80 followed by 10 weeks vehicle). Effective treatment duration is at least 6 weeks. The present invention is used with combinations of selected copper minerals that have shown promise for sustained release and PLA carrier that will delay their exposure to biological fluids.

Based on their release profiles of $Cu^{2+}$ from alginate gels, the copper minerals atacamite ($Cu_2Cl(OH)_3$) and hydroxy cupric phosphate heptahydrate ($Cu_8(PO_3OH)_2(PO_4)_4.7H_2O$), [Bassett et al.] abbreviated CuC and CuP, are selected for sustained release from polylactide (PLA) composite particles. Basset et al. showed that the rate of $Cu^{2+}$ release from alginate hydrogel can be tuned from a half-time less than 1 day to more than 14 days by control of crystal perfection, crystal size, mineral form and dissolution medium (dissolution is relatively rapid in biological media). Prior results suggest that release from 30 μm diameter<1%-D PLA nanocomposite particles can extend release for more than 30 days. Some experimentation is required to finalize the selection of stereoregularity of PLA (i.e., D-content), CuC:CuP ratios, total mineral loading and PLA-composite particle size to provide overlapping release kinetics that combine to approximate linear release profiles for up to 6 weeks in corneal stroma in vitro.

Delivery of a 2-week dose requires $\{2\times10^{-11}$ mol Cu(II)/day$\}$ $\{14$ days$\}=2.8\times10^{-10}$ mol Cu(II) which can be provided using approximately 180 composite particles of 10 μm diameter containing 40 vol % mineral (1:1 CuC:CuP by mass). This particle size is of particular interest because it is not expected to be perceptible by the patient; and the total number of particles is small enough that the particles would occlude less than 0.04% of the area of the cornea. Mineral particles will are synthesized following literature protocols that provide pure atacamite[Pollard 1989] [61] or pure hydroxy cupric phosphate heptahydrate[Chen 2009] [62]. Both of these minerals tend to form platelet-shaped crystals that are 20-40 nm thick and 500-1000 nm across. Rigorously dry particles are dispersed in chloroform using sonication and the suspension of particles is then mixed with a 10% w/w PLA solution in chloroform. The presence of PLA stabilizes the mineral dispersion. Spray drying is used to synthesize substantially spherical particles that have dimension 10 to 20 μm.

The density of the particles is calculated using $vf_{PLA}$=60% vol fraction PLA (dry solid), vf_CuC=20% vol fraction CuC, vf_CuP=20% vol fraction CuP and using the densities $\rho_{PLA}$, $\rho_{CuC}$, and $\rho_{CuP}$. The density of the particles is thus $Vf_{PLA}\ \rho_{PLA}+vf_{CUC}\ \rho_{CuC}+Vf_{CUP}\ \rho_{CuP}$. The resulting density and the desired particle size range 10 to 20 μm is used with the example above that provides experimental results a higher and a lower particle density. Interpolating between the two densities and their corresponding velocity ranges for delivery to the posterior epithelium provides velocities that would be suitable for size 20 to 30 μm. Smaller particles will need to have faster velocity. Based on the example that describes the probability density of penetration depth for individual sizes, the velocity is increased by a factor of 25/15, the middle values of the two size ranges, 20 to 30 μm and 10 to 20 μm. The resulting combination of particle density, particle size range and velocity range will deliver more than 50% of the particles to the posterior half of the epithelium.

The examples set forth above are provided to give those of ordinary skill in the art a complete disclosure and description of how to make and use the embodiments of the compounds, compositions, systems and methods of the disclosure, and are not intended to limit the scope of what the inventors regard as their disclosure. All patents and publications mentioned in the specification are indicative of the levels of skill of those skilled in the art to which the disclosure pertains.

The entire disclosure of each document cited (including webpages patents, patent applications, journal articles, abstracts, laboratory manuals, books, or other disclosures) in the Background, Summary, Detailed Description, and Examples is hereby incorporated herein by reference. All references cited in this disclosure, including references cited in any one of the Appendices, are incorporated by reference to the same extent as if each reference had been incorporated by reference in its entirety individually. However, if any inconsistency arises between a cited reference and the present disclosure, the present disclosure takes precedence.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the disclosure has been specifically disclosed by embodiments, exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible subcombinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified can be employed in the practice of the disclosure without resort to undue experimentation. All art-known functional equivalents, of any such methods, device elements, and materials are intended to be included in this disclosure.

Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein can be excluded from a claim of this disclosure. The disclosure illustratively described herein suitably can be practiced in the absence of any element or elements, limitation or limitations, which is not specifically disclosed herein.

"Optional" or "optionally" means that the subsequently described circumstance may or may not occur, so that the description includes instances where the circumstance occurs and instances where it does not according to the guidance provided in the present disclosure. For example, the phrase "optionally substituted" means that a non-hydrogen substituent may or may not be present on a given atom, and, thus, the description includes structures wherein a non-hydrogen substituent is present and structures wherein a non-hydrogen substituent is not present. It will be appreciated that the phrase "optionally substituted" is used interchangeably with the phrase "substituted or unsubstituted." Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned can be identified in view of the desired features of the compound in view of the present disclosure, and in view of the features that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

A number of embodiments of the disclosure have been described. The specific embodiments provided herein are examples of useful embodiments of the disclosure and it will be apparent to one skilled in the art that the disclosure can be carried out using a large number of variations of the devices, device components, methods steps set forth in the present description. As will be obvious to one of skill in the art, methods and devices useful for the present methods can include a large number of optional composition and processing elements and steps.

In particular, it will be understood that various modifications may be made without departing from the spirit and scope of the present disclosure. Accordingly, other embodiments are within the scope of the following claims.

REFERENCES

1. Ahmed, I., *The noncorneal route in ocular drug delivery, in Ophthalmic drug delivery systems*. 2003, CRC Press. p. 356-385.
2. Ehlers, N. and J. Hjortdal, *The cornea: epithelium and stroma*. Advances in organ biology, 2005. 10: p. 83-111.
3. Lindblad, N. R. and J. Schneider, *Production of uniform-sized liquid droplets*. Journal of Scientific Instruments, 1965. 42(8): p. 635.
4. Jackson, C. M., et al., *Defining and measuring biological activity: applying the principles of metrology*. Accreditation and quality assurance, 2007. 12(6): p. 283-294.
5. Pelikan, E. W., *Glossary of terms and symbols used in pharmacology*. University School of Medicine, Department of Pharmacology and Experimental Therapeutics, Boston, 2004.
6. Wikipedia. *Polymer*. https://web.archive.org/web/20191212045342/https://en.wikipedia.org/wiki/Polymer 2019.
7. Wikipedia. *Porous glass*. https://web.archive.org/web/20200612145638/https://en.wikipedia.org/wiki/Porous_glass 2020.
8. Corporation, M.-S. *Porous Silica*. https://mo-sci.com/products/porous-silica/2021.
9. Zilony, N., et al., *Bombarding cancer: biolistic delivery of therapeutics using porous Si carriers*. Scientific reports, 2013. 3(1): p. 1-6.
10. Ling, Y., et al., *Tungsten carbide hollow microspheres with robust and stable electrocatalytic activity toward hydrogen evolution reaction*. ACS omega, 2019. 4(2): p. 4185-4191.
11. Xiong, C., et al., *Mass, size, and density measurements of microparticles in a quadrupole ion trap*. Analytical chemistry, 2019. 91(21): p. 13508-13513.
12. Webb, P. A., Volume and density determinations for particle technologists. Micromeritics Instrument Corp (https://www.micromeritics.com/Repository/Files/Volume_and_Density_determinations_for_Particle_Technologists.pdf), 2001: p. 1-16.
13. Guo, Q., et al., *Entanglement-based thermoplastic shape memory polymeric particles with photothermal actuation for biomedical applications*. ACS applied materials & *interfaces*, 2018. 10(16): p. 13333-13341.
14. Alemrayat, B., et al., *Preparation and optimization of monodisperse polymeric microparticles using modified vibrating orifice aerosol generator for controlled delivery of letrozole in breast cancer therapy*. Drug development and industrial pharmacy, 2018. 44(12): p. 1953-1965.
15. Ribeiro, M. D. M., D. B. Arellano, and C. R. F. Grosso, *The effect of adding oleic acid in the production of stearic*

*acid lipid microparticles with a hydrophilic core by a spray-cooling process*. Food Research International, 2012. 47(1): p. 38-44.

16. X. Ma Y. Liu W. Fan Z. Cui, *Cryopreservation: Organ Preservation, in Comprehensive Biotechnology* (*Second Edition*). 2011, Academic Press. p. 83-98.
17. Wikipedia. *Tissue* (*biology*). https://web.archive.org/web/20191201005711/https://en.wikipedia.org/wiki/Tissue_(biology) 2019.
18. Wikipedia. *Epithelium*. https://web.archive.org/web/20190325184737/https://en.wikipedia.org/wiki/Epithelium 2019.
19. Blackburn, B. J., et al., *A review of structural and biomechanical changes in the cornea in aging, disease, and photochemical crosslinking*. Frontiers in bioengineering and biotechnology, 2019. 7: p. 1-16.
20. Marchini, M., et al., *Differences in the fibril structure of corneal and tendon collagen. An electron microscopy and X-ray diffraction investigation*. Connective tissue research, 1986. 15(4): p. 269-281.
21. Last, J. A., et al., *Compliance profile of the human cornea as measured by atomic force microscopy*. Micron, 2012. 43(12): p. 1293-1298.
22. Gouveia, S. M. and J. M. Tiffany, *Human tear viscosity: an interactive role for proteins and lipids*. Biochimica et Biophysica Acta (BBA)—Proteins and Proteomics, 2005. 1753(2): p. 155-163.
23. Thomasy, S. M., et al., *Elastic modulus and collagen organization of the rabbit cornea: epithelium to endothelium*. Acta biomaterialia, 2014. 10(2): p. 785-791.
24. Gaudana, R., et al., *Ocular drug delivery*. The AAPS journal, 2010. 12(3): p. 348-360.
25. Berglund, R. N. and B. Y. Liu, *Generation of monodisperse aerosol standards*. Environmental Science & Technology, 1973. 7(2): p. 147-153.
26. Mattson, M., D. Schwartz, and J. Kornfield, *Mechanical measurements of sclera for screening myopia treatments*. Investigative Ophthalmology & Visual Science, 2005. 46(13): p. 1991-1991.
27. Nickerson, C. S. and J. A. Kornfield, *A "cleat" geometry for suppressing wall slip*. Journal of Rheology, 2005. 49(4): p. 865-874.
28. Sharma, A., et al., Strain-*controlled criticality governs the nonlinear mechanics of fibre networks*. Nature Physics, 2016. 12(6): p. 584-587.
29. Shariati, A., et al., *The Effects of Davidson's Fixative Solution in Preserving the Rabbit Eye*. Investigative Ophthalmology & Visual Science, 2008. 49(13): p. 5207-5207.
30. Abhari, S., et al., *Anatomic studies of the miniature swine cornea*. The Anatomical Record, 2018. 301(11): p. 1955-1967.
31. Kendall, M., P. W. Smith, and B. Bellhouse. *Transdermal ballistic delivery of micro-particles: investigation into skin penetration*. in *BS EMBS Int. Conf.* 2000. IEEE.
32. Kendall, M., T. Mitchell, and P. Wrighton-Smith, *Intradermal ballistic delivery of micro-particles into excised human skin for pharmaceutical applications*. Journal of biomechanics, 2004. 37(11): p. 1733-1741.
33. Hedbys, B. O. and S. Mishima, *The thickness-hydration relationship of the cornea*. Experimental eye research, 1966. 5(3): p. 221-228.
34. Warner, R. R., M. C. Myers, and D. A. Taylor, *Electron probe analysis of human skin: determination of the water concentration profile*. Journal of Investigative Dermatology, 1988. 90(2): p. 218-224.
35. Wikipedia. *Ballistic gelatin*, accessed at https.//web.archive.org/web/20181222100214/https://en.wikipedia.org/wiki/Ballistic_gelatin. 2018.
36. Segletes, S. B., *Modeling the penetration behavior of rigid into ballistic gelatin*. 2008, Army Research Lab Aberdeen Proving Ground Md.
37. Jussila, J., *Preparing ballistic gelatine—review and proposal for a standard method*. Forensic science international, 2004. 141(2-3): p. 91-98.
38. Veysset, D., et al., *High-velocity micro particle impact on gelatin and synthetic hydrogel*. Journal of the mechanical behavior of biomedical materials, 2018. 86: p. 71-76.
39. Swain, M., et al., *Projectile penetration into ballistic gelatin*. Journal of the mechanical behavior of biomedical materials, 2014. 29: p. 385-392.
40. Akers, B. and A. Belmonte, *Impact dynamics of a solid sphere falling into a viscoelastic micellar fluid*. Journal of Non-Newtonian Fluid Mechanics, 2006. 135(2-3): p. 97-108.
41. Campbell, L., *Under the hood: The physics of projectile ballistics*. http://panoptesv.com/RPGs/Equipment/Weapons/Projectile_physics.php.
42. Ableson, M. B., Maffei, C. & Howe, A. J., *Why Doesn't the Ocular Drug Work? A look at the various barriers and aids to the efficacy of ocular medications*. Review of Ophthalmology 2009.
43. Daull, P., M. Amrane, and J. Garrigue, *Novasorb® Cationic Nanoemulsion and Latanoprost: The ideal combination for glaucoma management*. J Eye Dis Disord, 2017. 2: p. 1.
44. Gordon-Shaag, A., et al., *The genetic and environmental factors for keratoconus*. BioMed research international, 2015. 2015: p. 24-32
45. Cifariello, F., et al., *Epi-off versus epi-on corneal collagen cross-linking in keratoconus patients: a comparative study through* 2-*year follow-up*. Journal of ophthalmology, 2018. 2018.
46. Jia, H.-Z. and X.-J. Peng, *Efficacy of iontophoresis-assisted epithelium-on corneal cross-linking for keratoconus*. International journal of ophthalmology, 2018. 11(4): p. 687.
47. Bidwell, G., et al., *A corneal penetrating drug delivery system based on elastin-like polypeptide* (1053.4). The FASEB Journal, 2014. 28: p. 1053.4.
48. Huynh, J., *Factors governing photodynamic cross-linking of ocular coat*. 2011: California Institute of Technology.
49. Olivares Jimenez, J. L., et al., *Keratoconus: age of onset and natural history*. Optom Vis Sci, 1997. 74(3): p. 147-51.
50. Kasbekar, S. A., et al., *Corneal transplant surgery for keratoconus and the effect of surgeon experience on deep anterior lamellar keratoplasty outcomes*. Am J Ophthalmol, 2014. 158(6): p. 1239-46.
51. Rebenitsch, R. L., et al., *The lifetime economic burden of keratoconus: a decision analysis using a markov model*. Am J Ophthalmol, 2011. 151(5): p. 768-773 e2.
52. Gore, D. M., A. J. Shortt, and B. D. Allan, *New clinical pathways for keratoconus*. Eye (Lond), 2013. 27(3): p. 329-39.
53. Caporossi, A., et al., *Long-term results of riboflavin ultraviolet a corneal collagen cross-linking for keratoconus in Italy: the Siena eye cross study*. Am J Ophthalmol, 2010. 149(4): p. 585-93.
54. Mazzotta, C., et al., *Stromal haze after combined riboflavin-UVA corneal collagen cross-linking in keratoco-*

*nus: in vivo confocal microscopic evaluation*. Clin Experiment Ophthalmol, 2007. 35(6): p. 580-2.

55. Vinciguerra, P., et al., *Refractive, topographic, tomographic, and aberrometric analysis of keratoconic eyes undergoing corneal cross-linking*. Ophthalmology, 2009. 116(3): p. 369-78.
56. Vinciguerra, R., et al., *Corneal cross-linking as a treatment for keratoconus: four-year morphologic and clinical outcomes with respect to patient age*. Ophthalmology, 2013. 120(5): p. 908-16.
57. Zamora, K. V. and J. J. *Males, Polymicrobial keratitis after a collagen cross-linking procedure with postoperative use of a contact lens: a case report*. Cornea, 2009. 28(4): p. 474-6.
58. Bykhovskaya, Y., et al., *Variation in the lysyl oxidase (LOX) gene is associated with keratoconus in family-based and case-control studies*. Invest Ophthalmol Vis Sci, 2012. 53(7): p. 4152-7.
59. Shetty, R., et al., *Attenuation of lysyl oxidase and collagen gene expression in keratoconus patient corneal epithelium corresponds to disease severity*. Mol Vis, 2015. 21: p. 12-25.
60. Dudakova, L. and K. Jirsova, *The impairment of lysyl oxidase in keratoconus and in keratoconus-associated disorders*. J Neural Transm (Vienna), 2013. 120(6): p. 977-82.
61. Pollard, A., R. Thomas, and P. Williams, *Synthesis and stabilities of the basic copper (II) chlorides atacamite, paratacamite and botallackite*. Mineralogical magazine, 1989. 53(373): p. 557-563.
62. Chen, X. H., et al., *Direct growth of hydroxy cupric phosphate heptahydrate monocrystal with honeycomb-like porous structures on copper surface mimicking lotus leaf*. Crystal Growth and Design, 2009. 9(6): p. 2656-2661.

The invention claimed is:

1. A method for controlled ballistic delivery of a biologically active cargo to the cornea of an individual comprising an epithelium layer and a stroma layer and an interface between the epithelium layer and the stroma layer, the method comprising ballistically delivering to the cornea a convex microparticle comprising the biologically active cargo optionally in combination with a carrier material, the convex microparticle having a diameter from 5 to 30 μm and a density from 1 g/cc up to less than 20 g/cc, the ballistically delivering performed at a velocity equal to or higher than 100 m/s to a set target region of the cornea from the epithelium layer to the stroma layer of the cornea of the individual wherein the ballistic delivery is controlled by selecting the density of the convex microparticle to correspond to the set target region such that:

wherein when the convex microparticle has a density from 1.0 g/cc to 2.5 g/cc the set target region is a target region located within the epithelium of the cornea, wherein when the convex microparticle has a density higher than 2.5 g/cc to 7.8 g/cc the set target region is a target region located in the epithelium layer, in the stroma layer of the cornea and/or within the interface between epithelium layer and stroma layer of the cornea, and wherein when the convex microparticle has a density higher than 7.8 g/cc to less than 20 g/cc the set target region is a target region within the interface between the epithelium layer and the stroma layer of the cornea, or within the stroma layer of the cornea.

2. The method of claim 1, wherein the ballistically delivering is performed at a velocity of from 200 m/s to 500 m/s.

3. The method of claim 1, wherein the convex microparticle comprises a carrier material and the carrier material comprises a polymer, a glass, a metal and/or an alloy.

4. The method of claim 1, wherein the carrier material comprises a polymer of Formula (I):

$$[B_1\text{-co-}(B_2)_{b2} \ldots \text{co-}(B_m)_{bm}][X_1]_{r1} \ldots [X_p]_{rp} \quad \text{(I)}$$

in which $B_1$ to $B_m$ each refers to a block polymer moiety which are copolymerized to form copolymer $B_1$-co-$B_2$ . . . co-$B_m$, wherein m ranges from 1 to 9, b2 to bm each refers to a molar fractional number of block polymer moiety B2 to Bm relative to B1, wherein b2 to bm are each equal to or less than 1 and a sum of b2 to bm is equal to or less than 5, $X_1$ to $X_p$ each refers to a cross-linker moiety, each of which cross-links at least two polymer moieties, r1 to rp each refers a molar fractional number of cross-linker $L_1$ to $L_p$ per block copolymer $[B_1\text{-co-}(B_2)_{b2} \ldots \text{co-}(B_m)_{bm}]$, wherein a sum of r1 to rp is equal to or less than 0.5, and wherein the molecular weight of the carrier particle ranges from 5000 Daltons to 5,000,000 Daltons.

5. The method of claim 4, wherein the polymer of Formula (I) comprises poly-N-2-dimethylamino ethyl-methacrylamide (PDMAEMAm), poly-N-2-dimethylamino ethyl-acrylamide (PDMAEAAm), poly-N-2-dimethylamino ethyl-methacrylate (PDMAEMA), poly-N-2-dimethylamino ethyl-acrylate (PDMAEA), poly methacrylamide (PMAAm), poly N,N-dimethyl methacrylamide (PDMMAAm), polymethyl methacrylate (PMMA), polyacrylamide (PAAm), polyacrylic acid (PAA), poly dimethylaminoethylmethacrylate (PDEAEMA), polyisopropylacrylamide (PNIPAAm), poly(N-isopropyl-3-butenamide) (PNIPBAm), alpha-aminoomega-methyl-poly ethylene glycol (AMPEG), poly(epsilon-caprolactone-co-lactide-polyethylene glycol) copolymer, cross-linked copolymers of polyethyleneglycol and methyacrylic acid, block copolymer poly(methacrylic acid-co-ethylene glycol), block copolymer poly(2-hydroxythyl methacrylate-co-N,N-dimethylaminoethyl methacrylate), poly(hydroxyethyl methacrylamide) (poly-HEMAm), copolymer poly(HEMA-co-DMAEMA) poly (hydroxylethyl methacrylate-co-N,N-dimethylaminoethylmethacrylate), copolymer of gelatin and PVA (polyvinyl alcohol), co-polymer of poly-PNIPA and poly-PNIPA-Co-AA (poly N-isopropyl acrylamide and poly N-isopropyl acrylamide-co-acrylic acid), poly organophosphazene with a-amino omegamethylpolyethylene glycol, polyepsilon caprolactone-co-lactide-polyethylene glycol, poly(NIPAAm-co-AAm) (N-isopropylacryalmide-co-acryalmide), poly(methacrylamide-co-N-vinyl-2-pyrrolidone-co-itaconic acid), poly(2-(N-ethylperfluorooctanesulfonamido) ethylacrylate), a cross-linked polymer thereof or a cross-linked any combination of polymers thereof.

6. The method of claim 1, wherein the carrier material comprises a polymer of Formula (II):

$$—[M]_n— \quad \text{(II)}$$

wherein M is a monomeric moiety, n is the degree of polymerization ranging from 50 to 500,000, M is a monomeric moiety formed by a polymerized monomer.

7. The method of claim 6, wherein the polymer of Formula (II) comprises poly(N-vinylpyrrolidone), poly (acrylic acid), poly(methacrylic acid), poly(2-hydroxyethyl methacrylate), poly(2-hydroxyethyl methacrylic acid), poly (2-hydroxypropyl methacrylate), poly(2-ethyl-2-oxazoline), polymethacrylamide, polyacrylamide, poly(N-iso-propylacrylamide), poly(2-vinylpyridine), poly(2-vinylpyridine N-oxide), poly(4-vinylpyridine), poly(4-vinylpyridine N-oxide), poly(2-vinyl-1-methylpyridinium bromide), poly (ethylene oxide), poly(propylene oxide), poly(styrenesulfonic acid), poly(styrenesulfonate sodium), poly(vinylsulfonic acid), poly(vinylsulfonate sodium), poly(vinyl phosphoric acid), poly(vinyl phosphorate sodium), poly(vinyl alcohol), poly(allyl amine), poly(2-methacryloxyethyltrimethylammonium bromide), poly(N-vinylpyrrolidone), poly(vinyl acetate) or any combinations thereof.

8. The method of claim 1, wherein the carrier material comprises a poly(ethylene glycol) (PEG), poly(D-lactic acid) (PDLA), poly(L-lactic acid) (PLLA), poly(D-lactic acid-co-L-lactic acid) (PDLLA) and poly(ethylene glycol), polyglycolic acid (PGA) or any combination thereof.

9. The method of claim 1, wherein the carrier material is carrier glass comprising any one of soda-lime glass, borosilicate glass, and an aluminosilicate glass.

10. The method of claim 1, wherein the carrier material is carrier metal from Group 3 to Group 12 elements and/or from metal elements in Group 13 to Group 14.

11. The method of claim 10, wherein the carrier material comprises any one of metal titanium, iron, copper, silver, gold, tungsten or a combination thereof.

12. The method of claim 1, wherein the carrier material is porous.

13. The method of claim 1, wherein the carrier material alloy comprising a metal of any one of Group 1 to Group 14.

14. The method of claim 1, wherein the carrier material is a porous carrier glass, a porous carrier metal and/or a porous carrier alloy.

15. The method of claim 1, wherein the cargo comprises a prostaglandin analog, a-adrenoreceptor agonist, B-adrenoreceptor antagonist, carbonic anhydrase inhibitor, and parasympathomimetic agents or any combination thereof.

16. The method of claim 1, wherein the cargo comprises an anti-angiogenic ophthalmic agent, a mydriatics, an anesthetic, an anti-infective agent, an antihistamine and/or decongestant, a glaucoma agent, a steroid or any combination thereof.

17. The method of claim 1, wherein the biologically active cargo comprises a photosensitizing agent capable of corneal cross-linking.

18. The method of claim 1, wherein the convex microparticle is a substantially spherical microparticle.

* * * * *